US007901928B2

(12) United States Patent
Yadav et al.

(10) Patent No.: US 7,901,928 B2
(45) Date of Patent: Mar. 8, 2011

(54) ACYLTRANSFERASES FOR ALTERATION OF POLYUNSATURATED FATTY ACIDS AND OIL CONTENT IN OLEAGINOUS YEASTS

(75) Inventors: Narendra S. Yadav, Wilmington, DE (US); Hongxiang Zhang, Chadds Ford, PA (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 12/401,650

(22) Filed: Mar. 11, 2009

(65) Prior Publication Data
US 2009/0269828 A1 Oct. 29, 2009

Related U.S. Application Data

(62) Division of application No. 11/716,162, filed on Mar. 9, 2007, now Pat. No. 7,521,223, which is a division of application No. 11/592,806, filed on Nov. 3, 2006, now Pat. No. 7,465,565, which is a division of application No. 10/882,760, filed on Jul. 1, 2004, now Pat. No. 7,267,976.

(60) Provisional application No. 60/484,599, filed on Jul. 2, 2003.

(51) Int. Cl.
C12N 9/10 (2006.01)
C12N 1/20 (2006.01)
C12N 1/19 (2006.01)
C12N 1/16 (2006.01)
C12P 15/70 (2006.01)
C12P 7/64 (2006.01)
C07H 21/24 (2006.01)

(52) U.S. Cl. ............. 435/254.21; 435/320.1; 435/252.3; 435/254.11; 435/193; 435/254.3; 435/134; 536/23.1; 536/23.2

(58) Field of Classification Search .................. None
See application file for complete search history.

(56) References Cited

U.S. PATENT DOCUMENTS

| 2001/0046691 A1 | 11/2001 | Bailey et al. |
| 2003/0028923 A1 | 2/2003 | Lardizabal et al. |
| 2003/0115632 A1 | 6/2003 | Lardizabal et al. |
| 2003/0124126 A1 | 7/2003 | Cases et al. |
| 2004/0107459 A1 | 6/2004 | Lardizabal et al. |
| 2005/0136519 A1 | 6/2005 | Picataggio et al. |

FOREIGN PATENT DOCUMENTS

| EP | 0005277 B1 | 1/1982 |
| WO | WO 00/60095 A2 | 10/2000 |
| WO | WO 01/34814 A1 | 5/2001 |

OTHER PUBLICATIONS

Whisstock et al. Quaterly Reviews of Biophysics, 2003, "Prediction of protein function from protein sequence and structure", 36(3): 307-340.*

Dahlqvist et al., Phospholipid:diacylglycerol acyltransferase: An enzyme that catalyzes the acyl-CoA-independent formation of triacylglycerol in yeast and plants, PNAS, 97(12):pp. 6487-6492, 2000.
Sandager et al., An acyl-CoA:Cholesterol acyltransferase (ACAT)-related gene is involved in the accumulation of triacylglycerols in *Saccharomyces cerevisiae*, Biochem. Soc. Trans. 28(6): pp. 700-702, 2000.
Sorger et al., Triacylglycerol biosynthesis in yeast, Appl., Microbiol. Biotechnol. vol. 61: pp. 289-299, 2003.
Sandager et al., Storage Lipid Synthesis is Non-essential in Yeast, J. Biol. Chem. 277(8): pp. 6478-6482, 2002.
Ratledge, C., Microbial Oils and Fats: An Essessment of their commercial Potential, Prog. Ind. Microbiol. vol. 16: 119-206, 1982.
Lardizabal et al., DGA%2 Is a New Diacylglycerol Acyltransferase Gene Family, J. Biol. Chem. 276 (42): pp. 38862-28869, 2001.
GenBank Accession No. NP_014888, *Saccharomyces cerevisiae*, Jul. 12, 2004.
GenBank Accession No. NM_012079, *Homo sapiens*, Jul. 15, 2004.
GenBank Accession No. NM_127503, *Arabidopsis thaliana*, Feb. 19, 2004.
GenBank Accession No. AF051849, *Arabidopsis thaliana*, Jan. 24, 2000.
GenBank Accession No. AJ238008, *Arabidopsis thaliana*, Jun. 18, 1999.
GenBank Accession No. NM_026384, *Mus musculus*, Dec. 22, 2003.
GenBank Accession No. NM_010046, *Mus musculus*, Mar. 21, 2004.
GenBank Accession No. AB057816, *Mus musculus*, Mar. 25, 2003.
GenBank Accession No. AB062762, *Rattus norvegicus*, Dec. 7, 2002.
GenBank Accession No. AF221132, *Caenorhabditis elegans*, May 22, 2002.
GenBank Accession No. AF391089, *Umbelopsis ramanniana*, Oct. 16, 2001.
GenBank Accession No. AF391090, *Umbelopsis ramanniana*, Oct. 16, 2001.
GenBank Accession No. AF129003, *Nicotiana tabacum*, Dec. 22, 1999.
GenBank Accession No. AF251794, *Brassica napus*, Apr. 16, 2000.
GenBank Accession No. AF164434, *Brassica napus*, Nov. 30, 1999.
Bouvier-Nave et al, Expression in yeast of an acyl-CoA: diacylglycerol acyltransferase cDNA from Caenorhabditis elegans, Biochem. Soc. Trans. 28(6):pp. 692-695, 2000.
Oelkers et al., The DGA1 Gene Determines a Second Triglyceride Synthetic Pathway in Yeast, J. Biol. Chem. 277(11): pp. 8877-8881, 2002.
Sorger and Daum, Synthesis of Triacylglycerols by the Acyl-Coenzyme A: Diacyl-glycerol Acyltransferase Dga1p in Lipid Particles of Yeast *Saccharomyces cerevisiae*, J. Bacteriol. 184: pp. 519-524, 2002.

(Continued)

*Primary Examiner* — Robert B Mondesi
*Assistant Examiner* — Iqbal H Chowdhury

(57) ABSTRACT

Two acyltransferases are provided, suitable for use in the manufacture of microbial oils enriched in omega fatty acids in oleaginous yeast (e.g., *Yarrowia lipolytica*). Specifically, the genes encoding phophatidylcholine-diacylglycerol acyltransferase (PDAT) and diacylglycerol acyltransferase (DGAT2) have been isolated from *Y. lipolytica*. These genes encode enzymes that participate in the terminal step in oil biosynthesis in yeast. Each is expected to play a key role in altering the quantity of polyunsaturated fatty acids produced in oils of oleaginous yeasts.

17 Claims, 8 Drawing Sheets

OTHER PUBLICATIONS

Oelkers et al., A Lecithin Cholesterol Acyltransferase-like Gene Mediates Diacylglycerol Esterification in Yeast, J. Biol. Chem. 275: 15609-15612, 2000.

Banas, A. et al., The involvement of phospholipids:diacylglycerol acyltransferases in tricylglycerol production, Biochem. Soc. Trans. 28(6): pp. 703-705, 2000.

GenBank Accession No. P40345, *Saccharomyces cerevisiae*, Jun. 15, 2002.

GenBank Accession No. O94680, *Schizosaccharomyces pombe*, Jun. 15, 2004.

GenBank Accession No. NP_596330, *Schizosaccharomyes pombe*, Jan. 12, 2004.

GenBank Accession No. NP_190069, *Arabidopsis thaliana*, Feb. 14, 2004.

GenBank Accession No. AB006704, *Arabidopsis thaliana*, Feb. 14, 2004.

Dyerberg, J. et al., *Fatty Acid Composition of the plasma lipids in Greenland Eskimos*, Amer. J. Clin Nutr. 28: pp. 958-966, 1975.

Dyerberg, J. et al., *Eicosapentaenoic Acid and Prevention of Thrombosis and Atherosclerosis?*, Lancet 2(8081): pp. 117-119, Jul. 15, 1978.

Shimokawa, H., Beneficial Effects of Eicosapentaenoic Acid on Endothelial Vasodilator Functions in Animals and Humans, World Rev. Nutr. Diet, 88: pp. 100-108, 2001.

Von Schacky et al. *Fatty Acids from Eskimos to Clical Cardiology—What Took Us So Long?* World Rev. Nutr. Diet, 88: pp. 90-99, 2001.

Bernard Dujon et al., Genome Evolution in Yeasts, Nature, vol. 430:35-44, 2004.

* cited by examiner

From Fig. 3B →

| Sc DGAT2 | Mr DGAT2b | Mr DGAT2a | Yl DGAT2 | |
|---|---|---|---|---|
| *** | 32.8 | 32.3 | 31.6 | Sc DGAT2 |
| | *** | 54.2 | 38.4 | Mr DGAT2b |
| | | *** | 37.7 | Mr DGAT2a |
| | | | *** | Yl DGAT2 |

Pair Distances in Percent Similarity of
DGAT.meg ClustalW (Slow/Accurate, Gonnet). DNASTAR

FIG. 4A

| Yl PDAT | Sp PDAT | Sc PDAT | At2 PDAT | At1 PDAT | |
|---|---|---|---|---|---|
| *** | 41.0 | 47.1 | 28.2 | 31.0 | Yl PDAT |
| | *** | 40.1 | 29.7 | 31.3 | Sp PDAT |
| | | *** | 28.9 | 29.3 | Sc PDAT |
| | | | *** | 58.3 | At2 PDAT |
| | | | | *** | At1 PDAT |

Pair Distances in Percent Similarity of
PDAT.meg ClustalW (Slow/Accurate, Gonnet). DNASTAR

A: Saccharomyces cerevisiae (SEQ ID NO:57; GenBank Accession No. CAA24607)
B: Schizosaccharomyces pombe (SEQ ID NO:58; GenBank Accession No. NP_595236)
C: Aspergillus oryzae (SEQ ID NO:59; GenBank Accession No. AAK08065)
D: Paralichthys olivaceus (SEQ ID NO:60; GenBank Accession No. BAA88638)
E: Xenopus laevis (SEQ ID NO:61; GenBank Accession No. P51469)
F: Gallus gallus (SEQ ID NO:62; GenBank Accession No. DECHG3)

SEQUENCE LISTING

```
<160> NUMBER OF SEQ ID NOS: 86

<210> SEQ ID NO 1
<211> LENGTH: 19
<212> TYPE: DNA
<213> ORGANISM: Artificial Sequence
<220> FEATURE:
<223> OTHER INFORMATION: Primer TEF5'
```

```
<400> SEQUENCE: 1
agagaccggg ttggcggcg                                                 19

<210> SEQ ID NO 2
<211> LENGTH: 30
<212> TYPE: DNA
<213> ORGANISM: Artificial Sequence
<220> FEATURE:
<223> OTHER INFORMATION: Primer TEF3'

<400> SEQUENCE: 2 ttggatccett tgaatgattc ttatactcag                                    30

<210> SEQ ID NO 3
<211> LENGTH: 29
<212> TYPE: DNA
<213> ORGANISM: Artificial Sequence
<220> FEATURE:
<223> OTHER INFORMATION: Primer XPR5'

<400> SEQUENCE: 3
tttccgcggc ccgagattcc ggcctcttc                                      29

<210> SEQ ID NO 4
<211> LENGTH: 31
<212> TYPE: DNA
<213> ORGANISM: Artificial Sequence
<220> FEATURE:
<223> OTHER INFORMATION: Primer XPR3'

<400> SEQUENCE: 4
tttccgcgga cacaatatct ggtcaaattt c                                   31

<210> SEQ ID NO 5
<211> LENGTH: 39
<212> TYPE: DNA
<213> ORGANISM: Artificial Sequence
<220> FEATURE:
<223> OTHER INFORMATION: Primer YL5

<400> SEQUENCE: 5 ccccccctcga ggtcgatggt gtcgataagc ttgatatcg                          39

<210> SEQ ID NO 6
<211> LENGTH: 39
<212> TYPE: DNA
<213> ORGANISM: Artificial Sequence
<220> FEATURE:
<223> OTHER INFORMATION: Primer YL6

<400> SEQUENCE: 6
cgatatcaag cttatcgaca ccatcgacct cgagggggg                           39

<210> SEQ ID NO 7
<211> LENGTH: 35
<212> TYPE: DNA
<213> ORGANISM: Artificial Sequence
<220> FEATURE:
<223> OTHER INFORMATION: Primer YL9

<400> SEQUENCE: 7
tggtaaataa atgatgtcga ctcaggcgac gacgg                               35

<210> SEQ ID NO 8
<211> LENGTH: 35
```

```
<212> TYPE: DNA
<213> ORGANISM: Artificial Sequence
<220> FEATURE:
<223> OTHER INFORMATION: Primer YL10

<400> SEQUENCE: 8
ccgtcgtcgc ctgagtcgac atcatttatt tacca                          35

<210> SEQ ID NO 9
<211> LENGTH: 37
<212> TYPE: DNA
<213> ORGANISM: Artificial Sequence
<220> FEATURE:
<223> OTHER INFORMATION: Primer YL7

<400> SEQUENCE: 9
caaccgattt cgacagttaa ttaataattt gaatcga                        37

<210> SEQ ID NO 10
<211> LENGTH: 37
<212> TYPE: DNA
<213> ORGANISM: Artificial Sequence
<220> FEATURE:
<223> OTHER INFORMATION: Primer YL8

<400> SEQUENCE: 10
tcgattcaaa ttattaatta actgtcgaaa tcggttg                        37

<210> SEQ ID NO 11
<211> LENGTH: 36
<212> TYPE: DNA
<213> ORGANISM: Artificial Sequence
<220> FEATURE:
<223> OTHER INFORMATION: Primer YL3

<400> SEQUENCE: 11
gtataagaat cattcaccat ggatccacta gttcta                         36

<210> SEQ ID NO 12
<211> LENGTH: 36
<212> TYPE: DNA
<213> ORGANISM: Artificial Sequence
<220> FEATURE:
<223> OTHER INFORMATION: Primer YL4

<400> SEQUENCE: 12
tagaactagt ggatccatgg tgaatgattc ttatac                         36

<210> SEQ ID NO 13
<211> LENGTH: 30
<212> TYPE: DNA
<213> ORGANISM: Artificial Sequence
<220> FEATURE:
<223> OTHER INFORMATION: Primer YL1

<400> SEQUENCE: 13
cagtgccaaa agccaaggca ctgagctcgt                                30

<210> SEQ ID NO 14
<211> LENGTH: 31
<212> TYPE: DNA
<213> ORGANISM: Artificial Sequence
<220> FEATURE:
<223> OTHER INFORMATION: Primer YL2

<400> SEQUENCE: 14
gacgagctca gtgccttggc ttttggcact g                              31
```

<210> SEQ ID NO 15
<211> LENGTH: 33
<212> TYPE: DNA
<213> ORGANISM: Artificial Sequence
<220> FEATURE:
<223> OTHER INFORMATION: Primer YL61

<400> SEQUENCE: 15
acaattccac acaacgtacg agccggaagc ata					33

<210> SEQ ID NO 16
<211> LENGTH: 33
<212> TYPE: DNA
<213> ORGANISM: Artificial Sequence
<220> FEATURE:
<223> OTHER INFORMATION: Primer YL62

<400> SEQUENCE: 16
tatgcttccg gctcgtacgt tgtgtggaat tgt					33

<210> SEQ ID NO 17
<211> LENGTH: 1026
<212> TYPE: DNA
<213> ORGANISM: Escherichia coli

<400> SEQUENCE: 17

```
atgaaaaagc ctgaactcac cgcgacgtct gtcgagaagt ttctgatcga aaagttcgac      60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat     180
cgttatgttt atcggcactt tgcatcggcc gcgctcccga ttccggaagt gcttgacatt     240
ggggaattca gcgagagcct gacctattgc atctcccgcc gtgcacaggg tgtcacgttg     300
caagacctgc ctgaaaccga actgcccgct gttctgcagc cggtcgcgga ggccatggat     360
gcgatcgctg cggccgatct tagccagacg agcgggttcg gcccattcgg accgcaagga     420
atcggtcaat acactacatg gcgtgatttc atatgcgcga ttgctgatcc ccatgtgtat     480
cactggcaaa ctgtgatgga cgacaccgtc agtgcgtccg tcgcgcaggc tctcgatgag     540
ctgatgcttt gggccgagga ctgccccgaa gtccggcacc tcgtgcacgc ggatttcggc     600
tccaacaatg tcctgacgga caatggccgc ataacagcgg tcattgactg gagcgaggcg     660
atgttcgggg attcccaata cgaggtcgcc aacatcttct tctggaggcc gtggttggct     720
tgtatggagc agcagacgcg ctacttcgag cggaggcatc cggagcttgc aggatcgccg     780
cggctccggg cgtatatgct ccgcattggt cttgaccaac tctatcagag cttggttgac     840
ggcaatttcg atgatgcagc ttgggcgcag gtcgatgcg acgcaatcgt ccgatccgga     900
gccgggactg tcgggcgtac acaaatcgcc cgcagaagcg cggccgtctg gaccgatggc     960
tgtgtagaag tactcgccga tagtggaaac cgacgcccca gcactcgtcc gagggcaaag    1020
gaatag                                                              1026
```

<210> SEQ ID NO 18
<211> LENGTH: 341
<212> TYPE: PRT
<213> ORGANISM: Escherichia coli

<400> SEQUENCE: 18

Met Lys Lys Pro Glu Leu Thr Ala Thr Ser Val Glu Lys Phe Leu Ile
1               5                   10                  15

```
Glu Lys Phe Asp Ser Val Ser Asp Leu Met Gln Leu Ser Glu Gly Glu
             20                  25                  30

Glu Ser Arg Ala Phe Ser Phe Asp Val Gly Gly Arg Gly Tyr Val Leu
         35                  40                  45

Arg Val Asn Ser Cys Ala Asp Gly Phe Tyr Lys Asp Arg Tyr Val Tyr
 50                  55                  60

Arg His Phe Ala Ser Ala Ala Leu Pro Ile Pro Glu Val Leu Asp Ile
 65                  70                  75                  80

Gly Glu Phe Ser Glu Ser Leu Thr Tyr Cys Ile Ser Arg Arg Ala Gln
                 85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 19
<211> LENGTH: 1710
<212> TYPE: DNA
<213> ORGANISM: Yarrowia lipolytica

<400> SEQUENCE: 19
gtcgacgagt atctgtctga ctcgtcattg ccgcctttgg agtacgactc caactatgag     60
tgtgcttgga tcactttgac gatacattct tcgttgaggc tgtgggtct gacagctgcg    120 ttttcggcgc ggttggccga caacaatatc agctgcaacg tcattgctgg ctttcatcat    180
gatcacattt ttgtcggcaa aggcgacgcc cagagagcca ttgacgttct ttctaatttg    240
gaccgatagc cgtatagtcc agtctatcta taagttcaac taactcgtaa ctattaccat    300
```

```
aacatatact tcactgcccc agataaggtt ccgataaaaa gttctgcaga ctaaatttat      360
ttcagtctcc tcttcaccac caaaatgccc tcctacgaag ctcgagctaa cgtccacaag      420
tccgcctttg ccgctcgagt gctcaagctc gtggcagcca agaaaaccaa cctgtgtgct      480
tctctggatg ttaccaccac caaggagctc attgagcttg ccgataaggt cggaccttat      540
gtgtgcatga tcaagaccca tatcgacatc attgacgact tcacctacgc cggcactgtg      600 ctcccctca aggaacttgc tcttaagcac ggtttcttcc tgttcgagga cagaaagttc       660
gcagatattg caacactgt caagcaccag tacaagaacg tgtctaccg aatcgccgag        720 tggtccgata tcaccaacgc ccacggtgta cccggaaccg gaatcattgc tggcctgcga     780
gctggtgccg aggaaactgt ctctgaacag aagaaggagg acgtctctga ctacgagaac     840
tcccagtaca aggagttcct ggtcccctct cccaacgaga gctggccag ggtctgctc       900 atgctggccg agctgtcttg caagggctct ctggccactg gcgagtactc caagcagacc    960
attgagcttg ccccgatccga ccccgagttt gtggttggct tcattgccca gaaccgacct   1020
aagggcgact ctgaggactg gcttattctg accccggggg tgggtcttga cgacaaggga   1080
gacgctctcg gacagcagta ccgaactgtt gaggatgtca tgtctaccgg aacggatatc   1140
ataattgtcg gccgaggtct gtacggccag aaccgagatc ctattgagga ggccaagcga   1200
taccagaagg ctggctggga ggcttaccag aagattaact gttagaggtt agactatgga   1260
tatgtcattt aactgtgtat atagagagcg tgcaagtatg gagcgcttgt tcagcttgta   1320
tgatggtcag acgacctgtc tgatcgagta tgtatgatac tgcacaacct gtgtatccgc   1380
atgatctgtc caatggggca tgttgttgtg tttctcgata cggagatgct gggtacaagt   1440
agctaatacg attgaactac ttatacttat atgaggcttg aagaaagctg acttgtgtat   1500
gacttattct caactacatc cccagtcaca ataccaccac tgcactacca ctacaccaaa   1560
accatgatca aaccacccat ggacttcctg gaggcagaag aacttgttat ggaaaagctc   1620
aagagagaga agccaagata ctatcaagac atgtgtcgca acttcaagga ggaccaagct   1680
ctgtacaccg agaaacaggc ctttgtcgac                                        1710
```

<210> SEQ ID NO 20
<211> LENGTH: 286
<212> TYPE: PRT
<213> ORGANISM: Yarrowia lipolytica

<400> SEQUENCE: 20

```
Met Pro Ser Tyr Glu Ala Arg Ala Asn Val His Lys Ser Ala Phe Ala
1               5                   10                  15

Ala Arg Val Leu Lys Leu Val Ala Ala Lys Lys Thr Asn Leu Cys Ala
            20                  25                  30

Ser Leu Asp Val Thr Thr Thr Lys Glu Leu Ile Glu Leu Ala Asp Lys
        35                  40                  45

Val Gly Pro Tyr Val Cys Met Ile Lys Thr His Ile Asp Ile Ile Asp
    50                  55                  60

Asp Phe Thr Tyr Ala Gly Thr Val Leu Pro Leu Lys Glu Leu Ala Leu
65                  70                  75                  80

Lys His Gly Phe Phe Leu Phe Glu Asp Arg Lys Phe Ala Asp Ile Gly
                85                  90                  95

Asn Thr Val Lys His Gln Tyr Lys Asn Gly Val Tyr Arg Ile Ala Glu
            100                 105                 110

Trp Ser Asp Ile Thr Asn Ala His Gly Val Pro Gly Thr Gly Ile Ile
        115                 120                 125
```

```
Ala Gly Leu Arg Ala Gly Ala Glu Glu Thr Val Ser Glu Gln Lys Lys
        130                 135                 140

Glu Asp Val Ser Asp Tyr Glu Asn Ser Gln Tyr Lys Glu Phe Leu Val
145                 150                 155                 160

Pro Ser Pro Asn Glu Lys Leu Ala Arg Gly Leu Leu Met Leu Ala Glu
                165                 170                 175

Leu Ser Cys Lys Gly Ser Leu Ala Thr Gly Leu Tyr Ser Lys Gln Thr
            180                 185                 190

Ile Glu Leu Ala Arg Ser Asp Pro Glu Phe Val Val Gly Phe Ile Ala
            195                 200                 205

Gln Asn Arg Pro Lys Gly Asp Ser Glu Asp Trp Leu Ile Leu Thr Pro
    210                 215                 220

Gly Val Gly Leu Asp Asp Lys Gly Asp Ala Leu Gly Gln Gln Tyr Arg
225                 230                 235                 240

Thr Val Glu Asp Val Met Ser Thr Gly Thr Asp Ile Ile Ile Val Gly
                245                 250                 255

Arg Gly Leu Tyr Gly Gln Asn Arg Asp Pro Ile Glu Glu Ala Lys Arg
            260                 265                 270

Tyr Gln Lys Ala Gly Trp Glu Ala Tyr Gln Lys Ile Asn Cys
            275                 280                 285

<210> SEQ ID NO 21
<211> LENGTH: 35
<212> TYPE: DNA
<213> ORGANISM: Artificial Sequence
<220> FEATURE:
<223> OTHER INFORMATION: Primer KU5

<400> SEQUENCE: 21
tttgcccggg cgagtatctg tctgactcgt cattg                              35

<210> SEQ ID NO 22
<211> LENGTH: 33
<212> TYPE: DNA
<213> ORGANISM: Artificial Sequence
<220> FEATURE:
<223> OTHER INFORMATION: Primer KU3

<400> SEQUENCE: 22
aaagcccggg caaaggcctg tttctcggtg tac                                33

<210> SEQ ID NO 23
<211> LENGTH: 29
<212> TYPE: DNA
<213> ORGANISM: Artificial Sequence
<220> FEATURE:
<223> OTHER INFORMATION: Primer P7
<220> FEATURE:
<221> NAME/KEY: misc_feature
<222> LOCATION: (24)..(24)
<223> OTHER INFORMATION: n is a, c, g, or t

<400> SEQUENCE: 23
aactacatct tcggctayca yccncaygg                                     29

<210> SEQ ID NO 24
<211> LENGTH: 10
<212> TYPE: PRT
<213> ORGANISM: Artificial Sequence
<220> FEATURE:
<223> OTHER INFORMATION: DGAT2 Consensus Sequence

<400> SEQUENCE: 24
```

-continued

```
Asn Tyr Ile Phe Gly Tyr His Pro His Gly
1               5                   10

<210> SEQ ID NO 25
<211> LENGTH: 29
<212> TYPE: DNA
<213> ORGANISM: Artificial Sequence
<220> FEATURE:
<223> OTHER INFORMATION: Primer P8
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 25
agggactcgg aggcgccgcc ncanacdat                                   29

<210> SEQ ID NO 26
<211> LENGTH: 10
<212> TYPE: PRT
<213> ORGANISM: Artificial Sequence
<220> FEATURE:
<223> OTHER INFORMATION: DGAT2 Consensus Sequence

<400> SEQUENCE: 26

Ile Val Val Gly Gly Ala Ser Glu Ser Leu
1               5                   10

<210> SEQ ID NO 27
<211> LENGTH: 23
<212> TYPE: DNA
<213> ORGANISM: Artificial Sequence
<220> FEATURE:
<223> OTHER INFORMATION: Primer P80

<400> SEQUENCE: 27
gggcatccct gtttctctta tga                                         23

<210> SEQ ID NO 28
<211> LENGTH: 23
<212> TYPE: DNA
<213> ORGANISM: Artificial Sequence
<220> FEATURE:
<223> OTHER INFORMATION: Primer P81

<400> SEQUENCE: 28
aacttccgag tgcctctcta cag                                         23

<210> SEQ ID NO 29
<211> LENGTH: 24
<212> TYPE: DNA
<213> ORGANISM: Artificial Sequence
<220> FEATURE:
<223> OTHER INFORMATION: LinkAmp Primer 1

<400> SEQUENCE: 29
aggcacagtc gaggacttat ccta                                        24

<210> SEQ ID NO 30
<211> LENGTH: 2119
<212> TYPE: DNA
<213> ORGANISM: Yarrowia lipolytica
<220> FEATURE:
<221> NAME/KEY: CDS
```

```
<222> LOCATION: (291)..(1835)
<223> OTHER INFORMATION: DGAT2 opening reading frame, comprising 2
      smaller internal opening reading frames
<220> FEATURE:
<221> NAME/KEY: misc_feature
<222> LOCATION: (291)..(293)
<223> OTHER INFORMATION: initiation codon ('ATG')
<220> FEATURE:
<221> NAME/KEY: misc_feature
<222> LOCATION: (456)..(458)
<223> OTHER INFORMATION: initiation codon ('ATG')
<220> FEATURE:
<221> NAME/KEY: misc_feature
<222> LOCATION: (768)..(770)
<223> OTHER INFORMATION: initiation codon ('ATG')

<400> SEQUENCE: 30
aaacgcaccc actgctcgtc ctccttgctc ctcgaaaccg actcctctac acacgtcaaa      60
tccgaggttg aaatcttccc cacatttggc agccaaacca gcacatccca gcaacctcgc     120
acagcgccga atcgacctg tcgacttggc acaaaaaaaa agcaccggct ctgcaacagt      180
tctcacgacc aattacgtac aagtacgaaa tcgttcgtgg accgtgactg ataagctccc     240 acttttctt ctaacaacag gcaacagaca agtcacacaa acaaaagct atg act         296
                                                      Met Thr
                                                        1 atc gac tca caa tac tac aag tcg cga gac aaa aac gac acg gca ccc       344
Ile Asp Ser Gln Tyr Tyr Lys Ser Arg Asp Lys Asn Asp Thr Ala Pro
      5                   10                  15 aaa atc gcg gga atc cga tat gcc ccg cta tcg aca cca tta ctc aac       392
Lys Ile Ala Gly Ile Arg Tyr Ala Pro Leu Ser Thr Pro Leu Leu Asn
 20                  25                  30 cga tgt gag acc ttc tct ctg gtc tgg cac att ttc agc att ccc act       440
Arg Cys Glu Thr Phe Ser Leu Val Trp His Ile Phe Ser Ile Pro Thr
 35                  40                  45                  50 ttc ctc aca att ttc atg cta tgc tgc gca att cca ctg ctc tgg cca       488
Phe Leu Thr Ile Phe Met Leu Cys Cys Ala Ile Pro Leu Leu Trp Pro
              55                  60                  65 ttt gtg att gcg tat gta gtg tac gct gtt aaa gac gac tcc ccg tcc       536
Phe Val Ile Ala Tyr Val Val Tyr Ala Val Lys Asp Asp Ser Pro Ser
          70                  75                  80 aac gga gga gtg gtc aag cga tac tcg cct att tca aga aac ttc ttc       584
Asn Gly Gly Val Val Lys Arg Tyr Ser Pro Ile Ser Arg Asn Phe Phe
     85                  90                  95 atc tgg aag ctc ttt ggc cgc tac ttc ccc ata act ctg cac aag acg       632
Ile Trp Lys Leu Phe Gly Arg Tyr Phe Pro Ile Thr Leu His Lys Thr
100                 105                 110 gtg gat ctg gag ccc acg cac aca tac tac cct ctg gac gtc cag gag       680
Val Asp Leu Glu Pro Thr His Thr Tyr Tyr Pro Leu Asp Val Gln Glu
115                 120                 125                 130 tat cac ctg att gct gag aga tac tgg ccg cag aac aag tac ctc cga       728
Tyr His Leu Ile Ala Glu Arg Tyr Trp Pro Gln Asn Lys Tyr Leu Arg
             135                 140                 145 gca atc atc tcc acc atc gag tac ttt ctg ccc gcc ttc atg aaa cgg       776
Ala Ile Ile Ser Thr Ile Glu Tyr Phe Leu Pro Ala Phe Met Lys Arg
        150                 155                 160 tct ctt tct atc aac gag cag gag cag cct gcc gag cga gat cct ctc       824
Ser Leu Ser Ile Asn Glu Gln Glu Gln Pro Ala Glu Arg Asp Pro Leu
    165                 170                 175 ctg tct ccc gtt tct ccc agc tct ccg ggt tct caa cct gac aag tgg       872
Leu Ser Pro Val Ser Pro Ser Ser Pro Gly Ser Gln Pro Asp Lys Trp
180                 185                 190 att aac cac gac agc aga tat agc cgt gga gaa tca tct ggc tcc aac       920
Ile Asn His Asp Ser Arg Tyr Ser Arg Gly Glu Ser Ser Gly Ser Asn
```

```
                195                 200                 205                 210
ggc cac gcc tcg ggc tcc gaa ctt aac ggc aac ggc aac aat ggc acc      968
Gly His Ala Ser Gly Ser Glu Leu Asn Gly Asn Gly Asn Asn Gly Thr
                        215                 220                 225 act aac cga cga cct ttg tcg tcc gcc tct gct ggc tcc act gca tct     1016
Thr Asn Arg Arg Pro Leu Ser Ser Ala Ser Ala Gly Ser Thr Ala Ser
            230                 235                 240 gat tcc acg ctt ctt aac ggg tcc ctc aac tcc tac gcc aac cag atc     1064
Asp Ser Thr Leu Leu Asn Gly Ser Leu Asn Ser Tyr Ala Asn Gln Ile
        245                 250                 255 att ggc gaa aac gac cca cag ctg tcg ccc aca aaa ctc aag ccc act     1112
Ile Gly Glu Asn Asp Pro Gln Leu Ser Pro Thr Lys Leu Lys Pro Thr
    260                 265                 270 ggc aga aaa tac atc ttc ggc tac cac ccc cac ggc att atc ggc atg     1160
Gly Arg Lys Tyr Ile Phe Gly Tyr His Pro His Gly Ile Ile Gly Met
275                 280                 285                 290 gga gcc ttt ggt gga att gcc acc gag gga gct gga tgg tcc aag ctc     1208
Gly Ala Phe Gly Gly Ile Ala Thr Glu Gly Ala Gly Trp Ser Lys Leu
                        295                 300                 305 ttt ccg ggc atc cct gtt tct ctt atg act ctc acc aac aac ttc cga     1256
Phe Pro Gly Ile Pro Val Ser Leu Met Thr Leu Thr Asn Asn Phe Arg
            310                 315                 320 gtg cct ctc tac aga gag tac ctc atg agt ctg gga gtc gct tct gtc     1304
Val Pro Leu Tyr Arg Glu Tyr Leu Met Ser Leu Gly Val Ala Ser Val
        325                 330                 335 tcc aag aag tcc tgc aag gcc ctc ctc aag cga aac cag tct atc tgc     1352
Ser Lys Lys Ser Cys Lys Ala Leu Leu Lys Arg Asn Gln Ser Ile Cys
    340                 345                 350 att gtc gtt ggt gga gca cag gaa agt ctt ctg gcc aga ccc ggt gtc     1400
Ile Val Val Gly Gly Ala Gln Glu Ser Leu Leu Ala Arg Pro Gly Val
355                 360                 365                 370 atg gac ctg gtg cta ctc aag cga aag ggt ttt gtt cga ctt ggt atg     1448
Met Asp Leu Val Leu Leu Lys Arg Lys Gly Phe Val Arg Leu Gly Met
                        375                 380                 385 gag gtc gga aat gtc gcc ctt gtt ccc atc atg gcc ttt ggt gag aac     1496
Glu Val Gly Asn Val Ala Leu Val Pro Ile Met Ala Phe Gly Glu Asn
            390                 395                 400 gac ctc tat gac cag gtt agc aac gac aag tcg tcc aag ctg tac cga     1544
Asp Leu Tyr Asp Gln Val Ser Asn Asp Lys Ser Ser Lys Leu Tyr Arg
        405                 410                 415 ttc cag cag ttt gtc aag aac ttc ctt gga ttc acc ctt cct ttg atg     1592
Phe Gln Gln Phe Val Lys Asn Phe Leu Gly Phe Thr Leu Pro Leu Met
    420                 425                 430 cat gcc cga ggc gtc ttc aac tac gat gtc ggt ctt gtc ccc tac agg     1640
His Ala Arg Gly Val Phe Asn Tyr Asp Val Gly Leu Val Pro Tyr Arg
435                 440                 445                 450 cga ccc gtc aac att gtg gtt ggt tcc ccc att gac ttg cct tat ctc     1688
Arg Pro Val Asn Ile Val Val Gly Ser Pro Ile Asp Leu Pro Tyr Leu
                        455                 460                 465 cca cac ccc acc gac gaa gaa gtg tcc gaa tac cac gac cga tac atc     1736
Pro His Pro Thr Asp Glu Glu Val Ser Glu Tyr His Asp Arg Tyr Ile
            470                 475                 480 gcc gag ctg cag cga atc tac aac gag cac aag gat gaa tat ttc atc     1784
Ala Glu Leu Gln Arg Ile Tyr Asn Glu His Lys Asp Glu Tyr Phe Ile
        485                 490                 495 gat tgg acc gag gag ggc aaa gga gcc cca gag ttc cga atg att gag     1832
Asp Trp Thr Glu Glu Gly Lys Gly Ala Pro Glu Phe Arg Met Ile Glu
    500                 505                 510 taa ggaaaactgc ctgggttagg caaatagcta atgagtattt ttttgatggc          1885
```

-continued

```
aaccaaatgt agaaagaaaa aaaaaaaaaa agaaaaaaaa aagagaatat tatatctatg   1945
taattctatt aaaagctctg ttgagtgagc ggaataaata ctgttgaaga ggggattgtg   2005
tagagatctg tttactcaat ggcaaactca tctgggggag atccttccac tgtgggaagc   2065
tcctggatag cctttgcatc ggggttcaag aagaccattg tgaacagccc ttga         2119

<210> SEQ ID NO 31
<211> LENGTH: 514
<212> TYPE: PRT
<213> ORGANISM: Yarrowia lipolytica

<400> SEQUENCE: 31

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
    290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
```

```
                          340                 345                 350
Ile Cys Ile Val Val Gly Gly Ala Gln Glu Ser Leu Leu Ala Arg Pro
            355                 360                 365
Gly Val Met Asp Leu Val Leu Leu Lys Arg Lys Gly Phe Val Arg Leu
370                 375                 380
Gly Met Glu Val Gly Asn Val Ala Leu Val Pro Ile Met Ala Phe Gly
385                 390                 395                 400
Glu Asn Asp Leu Tyr Asp Gln Val Ser Asn Asp Lys Ser Ser Lys Leu
                405                 410                 415
Tyr Arg Phe Gln Gln Phe Val Lys Asn Phe Leu Gly Phe Thr Leu Pro
            420                 425                 430
Leu Met His Ala Arg Gly Val Phe Asn Tyr Asp Val Gly Leu Val Pro
                435                 440                 445
Tyr Arg Arg Pro Val Asn Ile Val Val Gly Ser Pro Ile Asp Leu Pro
            450                 455                 460
Tyr Leu Pro His Pro Thr Asp Glu Glu Val Ser Glu Tyr His Asp Arg
465                 470                 475                 480
Tyr Ile Ala Glu Leu Gln Arg Ile Tyr Asn Glu His Lys Asp Glu Tyr
                485                 490                 495
Phe Ile Asp Trp Thr Glu Glu Gly Lys Gly Ala Pro Glu Phe Arg Met
            500                 505                 510
Ile Glu

<210> SEQ ID NO 32
<211> LENGTH: 29
<212> TYPE: DNA
<213> ORGANISM: Artificial Sequence
<220> FEATURE:
<223> OTHER INFORMATION: Primer P95

<400> SEQUENCE: 32
ggcaagctta ttgtcgttgg tggagcaca                                29

<210> SEQ ID NO 33
<211> LENGTH: 35
<212> TYPE: DNA
<213> ORGANISM: Artificial Sequence
<220> FEATURE:
<223> OTHER INFORMATION: Primer P96

<400> SEQUENCE: 33
aattccacca gatctgtcgt ggtattcgga cactt                         35

<210> SEQ ID NO 34
<211> LENGTH: 39
<212> TYPE: DNA
<213> ORGANISM: Artificial Sequence
<220> FEATURE:
<223> OTHER INFORMATION: Primer P97

<400> SEQUENCE: 34
ataccacgac agatctggtg gaattgccac cgagggagc                     39

<210> SEQ ID NO 35
<211> LENGTH: 30
<212> TYPE: DNA
<213> ORGANISM: Artificial Sequence
<220> FEATURE:
<223> OTHER INFORMATION: Primer P98

<400> SEQUENCE: 35
```

```
gcggaattcg cagatagact ggtttcgctt                                          30
```

<210> SEQ ID NO 36
<211> LENGTH: 22
<212> TYPE: DNA
<213> ORGANISM: Artificial Sequence
<220> FEATURE:
<223> OTHER INFORMATION: Primer P115

<400> SEQUENCE: 36

```
aactacatct tcggctatca cc                                                  22
```

<210> SEQ ID NO 37
<211> LENGTH: 22
<212> TYPE: DNA
<213> ORGANISM: Artificial Sequence
<220> FEATURE:
<223> OTHER INFORMATION: Primer P116

<400> SEQUENCE: 37

```
tgaacaagcg tagattccag ac                                                  22
```

<210> SEQ ID NO 38
<211> LENGTH: 22
<212> TYPE: DNA
<213> ORGANISM: Artificial Sequence
<220> FEATURE:
<223> OTHER INFORMATION: Primer P112

<400> SEQUENCE: 38

```
cacccttgct cggcgatgta tc                                                  22
```

<210> SEQ ID NO 39
<211> LENGTH: 29
<212> TYPE: DNA
<213> ORGANISM: Artificial Sequence
<220> FEATURE:
<223> OTHER INFORMATION: Primer P26
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 39

```
atgctggaca aggagaccgg nctngaycc                                           29
```

<210> SEQ ID NO 40
<211> LENGTH: 10
<212> TYPE: PRT
<213> ORGANISM: Artificial Sequence
<220> FEATURE:
<223> OTHER INFORMATION: PDAT Consensus Sequence

<400> SEQUENCE: 40

```
Met Leu Asp Lys Glu Thr Gly Leu Asp Pro
1               5                   10
```

<210> SEQ ID NO 41
<211> LENGTH: 33
<212> TYPE: DNA
<213> ORGANISM: Artificial Sequence
<220> FEATURE:
<223> OTHER INFORMATION: Primer P27
<220> FEATURE:
<221> NAME/KEY: misc_feature

```
<222> LOCATION: (25)..(25)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 41
ccagatgacg tcgccgccct tgggnarcat nga                                   33

<210> SEQ ID NO 42
<211> LENGTH: 11
<212> TYPE: PRT
<213> ORGANISM: Artificial Sequence
<220> FEATURE:
<223> OTHER INFORMATION: PDAT Consensus Sequence

<400> SEQUENCE: 42

Ser Met Leu Pro Lys Gly Gly Glu Val Ile Trp
1               5                   10

<210> SEQ ID NO 43
<211> LENGTH: 34
<212> TYPE: DNA
<213> ORGANISM: Artificial Sequence
<220> FEATURE:
<223> OTHER INFORMATION: Primer P39

<400> SEQUENCE: 43
ggcggtaccg gatcctcaat cgaagagact aagc                                  34

<210> SEQ ID NO 44
<211> LENGTH: 30
<212> TYPE: DNA
<213> ORGANISM: Artificial Sequence
<220> FEATURE:
<223> OTHER INFORMATION: Primer P42

<400> SEQUENCE: 44
ccggaattca gctttgagct tggagaagta                                       30

<210> SEQ ID NO 45
<211> LENGTH: 2326
<212> TYPE: DNA
<213> ORGANISM: Yarrowia lipolytica
<220> FEATURE:
<221> NAME/KEY: misc_feature
<222> LOCATION: (2271)..(2271)
<223> OTHER INFORMATION: n is a, c, g, or t

<400> SEQUENCE: 45
tattaatatt atgctcttca tgcaccagca aaataaccga aacgcgcata tgatagtggg      60
attctcgatt tgcccggcag acaaacgccg ctaaaatcgc cacagtatcg aatttaatt     120 gaatacgaac gtcaattccg gcttatcctt ctagcagttg tctcccgcag ctcgctccat    180
gactaatcat tcacgcgaca tgtctcagct accccggtct ggctcatgta aaaaaagtgt    240
aatcggcttt tttccggttg atcacaacca tcaatgacac aacctgtgaa tcggaaggcg    300
actgtcgagc gggtcgagcc agcagtggag gtggctgact ccgagtccga ggccaagacc    360
gacgtccacg ttcaccacca tcatcaccac acaagcgaa aatccgtcaa gggcaagatt     420
ctcaacttct tcacccgaag tcgacgtatc accttcgtcc tcggcgccgt ggtcggtgtg    480
atagccgcgg gatactacgc tgcgccaccg gagctcagca ttgatatcga tgctcttctc    540
ggcgacttgc cctcgttcga ctttgacgct ctatctctcg acaacttgtc catggacagt    600
```

```
gtgtcggact tgtacaaga catgaaatcg cggtttccga ccaagattct gcaggaggcg    660
gccaagatcg agaagcacca gaaaagcgaa cagaaggctg ccccttttgc tgtgggcaag    720
gctatgaaga gcgagggact caacgccaag tacccggtgg tgctggtgcc cggcgtcatc    780
tccacgggac tggagagctg gtccctggag ggaaccgagg agtgtcccac cgagtcgcac    840
ttcagaaagc gaatgtgggg ctcctggtac atgatccgag tcatgctgct ggacaagtac    900
tgctggctgc agaacctgat gctggacaca gagaccggtc tagaccctcc ccatttcaag    960
ctgcgagccg cccagggatt tgcctccgcc gacttcttta tggcaggcta ctggctgtgg   1020
aacaagctgc tcgagaacct ggctgttatt ggatacgata cggatacaat gtctgctgcg   1080
gcgtacgact ggagactgtc ctaccctgat ttggagcacc gagacggata cttctccaag   1140
ctcaaagctt caatcgaaga gactaagcgt atgacaggtg agaagacagt tctgacgggc   1200
cattccatgg gctcccaggt catcttctac ttcatgaagt gggctgaggc cgagggatat   1260
ggaggaggag gtcccaactg ggtcaatgac catattgaat cctttgtcga catttccggc   1320
tccatgctgg gtactcccaa gaccctggtt gctcttctgt ctggagaaat gaaggatacc   1380
gtgcagctga acgcgatggc tgtgtatgga ctggagcagt tcttctctcg acgagagcga   1440
gccgatctgc tgcgaacatg gggaggaatt gcttccatga ttcccaaggg tggtaaggct   1500
atctggggtg atcattctgg agcccctgat gacgagcccg ccagaatgt cacctttggc   1560
aacttcatca agttcaagga gtccttgacc gagtactctg ctaagaacct caccatggat   1620
gaaaccgttg acttcctgta ttctcagtct cccgagtggt tgtgaaccg aaccgagggt   1680
gcttactcct ttggaattgc caagactcga aagcaggttg agcagaatga aagcgacct    1740
tctacctgga gcaaccctct ggaagctgct ctccccaatg ccccgatct caagatctac    1800
tgcttctatg gagtcggtaa ggataccgag cgagcctact actaccagga tgagcccaat    1860
cccgagcaga ccaacttgaa cgtcagtatc gctggaaacg accctgatgg tgtgcttatg    1920
ggtcagggcg atggaaccgt ctcccttgtg acccatacca tgtgtcaccg atggaaggac    1980
gagaattcca agttcaaccc tggtaacgcc caggtcaagg ttgtggagat gttgcaccag    2040
cctgatcgac ttgatattcg aggcggtgct cagactgccg agcatgtgga cattctgggg    2100
cgttctgagt tgaacgagat ggttctgaag gtggctagtg aaagggaaa tgagattgaa     2160
gagagagtca tctccaacat tgatgagtgg gtgtggaaga ttgatctcgg cagcaattag    2220
agagtccgtt ttgtagagta atatgttttg tatatcacac tgatggagaa nggcgttcga    2280
tttctcatga ttccatgtgg ttgtttaatg agcacgtaga acgacg                  2326
```

<210> SEQ ID NO 46
<211> LENGTH: 648
<212> TYPE: PRT
<213> ORGANISM: Yarrowia lipolytica

<400> SEQUENCE: 46

Met Thr Gln Pro Val Asn Arg Lys Ala Thr Val Glu Arg Val Glu Pro
1               5                   10                  15

Ala Val Glu Val Ala Asp Ser Glu Ser Glu Ala Lys Thr Asp Val His
            20                  25                  30

Val His His His His His His Lys Arg Lys Ser Val Lys Gly Lys
        35                  40                  45

Ile Leu Asn Phe Phe Thr Arg Ser Arg Arg Ile Thr Phe Val Leu Gly
    50                  55                  60

Ala Val Val Gly Val Ile Ala Ala Gly Tyr Tyr Ala Ala Pro Pro Glu
65                  70                  75                  80

```
Leu Ser Ile Asp Ile Asp Ala Leu Leu Gly Asp Leu Pro Ser Phe Asp
                85                  90                  95

Phe Asp Ala Leu Ser Leu Asp Asn Leu Ser Met Asp Ser Val Ser Asp
            100                 105                 110

Phe Val Gln Asp Met Lys Ser Arg Phe Pro Thr Lys Ile Leu Gln Glu
            115                 120                 125

Ala Ala Lys Ile Glu Lys His Gln Lys Ser Glu Gln Lys Ala Ala Pro
        130                 135                 140

Phe Ala Val Gly Lys Ala Met Lys Ser Glu Gly Leu Asn Ala Lys Tyr
145                 150                 155                 160

Pro Val Val Leu Val Pro Gly Val Ile Ser Thr Gly Leu Glu Ser Trp
                165                 170                 175

Ser Leu Glu Gly Thr Glu Glu Cys Pro Thr Glu Ser His Phe Arg Lys
            180                 185                 190

Arg Met Trp Gly Ser Trp Tyr Met Ile Arg Val Met Leu Leu Asp Lys
            195                 200                 205

Tyr Cys Trp Leu Gln Asn Leu Met Leu Asp Thr Glu Thr Gly Leu Asp
        210                 215                 220

Pro Pro His Phe Lys Leu Arg Ala Ala Gln Gly Phe Ala Ser Ala Asp
225                 230                 235                 240

Phe Phe Met Ala Gly Tyr Trp Leu Trp Asn Lys Leu Leu Glu Asn Leu
                245                 250                 255

Ala Val Ile Gly Tyr Asp Thr Asp Thr Met Ser Ala Ala Ala Tyr Asp
            260                 265                 270

Trp Arg Leu Ser Tyr Pro Asp Leu Glu His Arg Asp Gly Tyr Phe Ser
            275                 280                 285

Lys Leu Lys Ala Ser Ile Glu Glu Thr Lys Arg Met Thr Gly Glu Lys
        290                 295                 300

Thr Val Leu Thr Gly His Ser Met Gly Ser Gln Val Ile Phe Tyr Phe
305                 310                 315                 320

Met Lys Trp Ala Glu Ala Glu Gly Tyr Gly Gly Gly Pro Asn Trp
                325                 330                 335

Val Asn Asp His Ile Glu Ser Phe Val Asp Ile Ser Gly Ser Met Leu
            340                 345                 350

Gly Thr Pro Lys Thr Leu Val Ala Leu Leu Ser Gly Glu Met Lys Asp
            355                 360                 365

Thr Val Gln Leu Asn Ala Met Ala Val Tyr Gly Leu Glu Gln Phe Phe
        370                 375                 380

Ser Arg Arg Glu Arg Ala Asp Leu Leu Arg Thr Trp Gly Gly Ile Ala
385                 390                 395                 400

Ser Met Ile Pro Lys Gly Gly Lys Ala Ile Trp Gly Asp His Ser Gly
                405                 410                 415

Ala Pro Asp Asp Glu Pro Gly Gln Asn Val Thr Phe Gly Asn Phe Ile
            420                 425                 430

Lys Phe Lys Glu Ser Leu Thr Glu Tyr Ser Ala Lys Asn Leu Thr Met
        435                 440                 445

Asp Glu Thr Val Asp Phe Leu Tyr Ser Gln Ser Pro Glu Trp Phe Val
        450                 455                 460

Asn Arg Thr Glu Gly Ala Tyr Ser Phe Gly Ile Ala Lys Thr Arg Lys
465                 470                 475                 480

Gln Val Glu Gln Asn Glu Lys Arg Pro Ser Thr Trp Ser Asn Pro Leu
                485                 490                 495

Glu Ala Ala Leu Pro Asn Ala Pro Asp Leu Lys Ile Tyr Cys Phe Tyr
```

```
                     500             505             510
Gly Val Gly Lys Asp Thr Glu Arg Ala Tyr Tyr Gln Asp Glu Pro
        515                 520             525

Asn Pro Glu Gln Thr Asn Leu Asn Val Ser Ile Ala Gly Asn Asp Pro
    530                 535             540

Asp Gly Val Leu Met Gly Gln Gly Asp Gly Thr Val Ser Leu Val Thr
545                 550             555                 560

His Thr Met Cys His Arg Trp Lys Asp Glu Asn Ser Lys Phe Asn Pro
                565             570             575

Gly Asn Ala Gln Val Lys Val Val Glu Met Leu His Gln Pro Asp Arg
            580             585             590

Leu Asp Ile Arg Gly Gly Ala Gln Thr Ala Glu His Val Asp Ile Leu
        595             600             605

Gly Arg Ser Glu Leu Asn Glu Met Val Leu Lys Val Ala Ser Gly Lys
            610             615             620

Gly Asn Glu Ile Glu Arg Val Ile Ser Asn Ile Asp Glu Trp Val
625             630             635             640

Trp Lys Ile Asp Leu Gly Ser Asn
                645

<210> SEQ ID NO 47
<211> LENGTH: 41
<212> TYPE: DNA
<213> ORGANISM: Artificial Sequence
<220> FEATURE:
<223> OTHER INFORMATION: Primer P41

<400> SEQUENCE: 47
cttctgtatt ctagatctca agatcgagaa gcaccagaaa a                    41

<210> SEQ ID NO 48
<211> LENGTH: 48
<212> TYPE: DNA
<213> ORGANISM: Artificial Sequence
<220> FEATURE:
<223> OTHER INFORMATION: Primer P40

<400> SEQUENCE: 48
gcttctcgat cttgagatct agaatacaga agtcaacggt tcatccat             48

<210> SEQ ID NO 49
<211> LENGTH: 22
<212> TYPE: DNA
<213> ORGANISM: Artificial Sequence
<220> FEATURE:
<223> OTHER INFORMATION: Primer P51

<400> SEQUENCE: 49
tagatagact ggactatacg gc                                         22

<210> SEQ ID NO 50
<211> LENGTH: 20
<212> TYPE: DNA
<213> ORGANISM: Artificial Sequence
<220> FEATURE:
<223> OTHER INFORMATION: Primer P52

<400> SEQUENCE: 50
gactgtccta ccctgatttg                                            20

<210> SEQ ID NO 51
<211> LENGTH: 33
```

```
<212> TYPE: DNA
<213> ORGANISM: Artificial Sequence
<220> FEATURE:
<223> OTHER INFORMATION: Primer P37

<400> SEQUENCE: 51
ccaggtacca agatcgagaa gcaccagaaa agc                                    33

<210> SEQ ID NO 52
<211> LENGTH: 36
<212> TYPE: DNA
<213> ORGANISM: Artificial Sequence
<220> FEATURE:
<223> OTHER INFORMATION: Primer P38

<400> SEQUENCE: 52
ctcgaattca gaatacagaa gtcaacggtt catcca                                 36

<210> SEQ ID NO 53
<211> LENGTH: 23
<212> TYPE: DNA
<213> ORGANISM: Artificial Sequence
<220> FEATURE:
<223> OTHER INFORMATION: Primer P79

<400> SEQUENCE: 53
tctctgtaga gaggcactcg gaa                                               23

<210> SEQ ID NO 54
<211> LENGTH: 23
<212> TYPE: DNA
<213> ORGANISM: Artificial Sequence
<220> FEATURE:
<223> OTHER INFORMATION: Primer P84

<400> SEQUENCE: 54
tgacgccggg caccagcacc acc                                               23

<210> SEQ ID NO 55
<211> LENGTH: 24
<212> TYPE: DNA
<213> ORGANISM: Artificial Sequence
<220> FEATURE:
<223> OTHER INFORMATION: Primer P85

<400> SEQUENCE: 55
gtcacctttg gcaacttcat caag                                              24

<210> SEQ ID NO 56
<211> LENGTH: 971
<212> TYPE: DNA
<213> ORGANISM: Yarrowia lipolytica

<400> SEQUENCE: 56
gacgcagtag gatgtcctgc acgggtcttt ttgtggggtg tggagaaagg ggtgcttgga        60
gatggaagcc ggtagaaccg ggctgcttgt gcttggagat ggaagccggt agaaccgggc       120
tgcttggggg gatttggggc cgctgggctc caaagagggg taggcatttc gttggggtta       180
cgtaattgcg gcatttgggt cctgcgcgca tgtcccattg gtcagaatta gtccggatag       240
gagacttatc agccaatcac agcgccgat ccacctgtag gttgggttgg gtgggagcac       300 cctccacag agtagagtca aacagcagca gcaacatgat agttgggggt gtgcgtgtta       360
aaggaaaaaa aagaagcttg ggttatattc ccgctctatt tagaggttgc gggatagacg      420
ccgacggagg gcaatggcgc catggaacct tgcggatatc gatacgccgc ggcggactgc      480
```

-continued

```
gtccgaacca gctccagcag cgttttttcc gggccattga gccgactgcg accccgccaa    540
cgtgtcttgg cccacgcact catgtcatgt tggtgttggg aggccacttt ttaagtagca    600
caaggcacct agctcgcagc aaggtgtccg aaccaaagaa gcggctgcag tggtgcaaac    660
ggggcggaaa cggcgggaaa aagccacggg ggcacgaatt gaggcacgcc ctcgaatttg    720
agacgagtca cggccccatt cgcccgcgca atggctcgcc aacgcccggt cttttgcacc    780
acatcaggtt accccaagcc aaaccttgt gttaaaaagc ttaacatatt ataccgaacg     840
taggtttggg cgggcttgct ccgtctgtcc aaggcaacat ttatataagg gtctgcatcg    900
ccggctcaat tgaatctttt ttcttcttct cttctctata ttcattcttg aattaaacac    960
acatcaacat g                                                         971
```

```
<210> SEQ ID NO 57
<211> LENGTH: 332
<212> TYPE: PRT
<213> ORGANISM: Sacchromyces cerevisiae
<220> FEATURE:
<221> NAME/KEY: MISC_FEATURE
<222> LOCATION: (1)..(332)
<223> OTHER INFORMATION: GenBank Accession No. CAA24607

<400> SEQUENCE: 57

Met Val Arg Val Ala Ile Asn Gly Phe Gly Arg Ile Gly Arg Leu Val
1               5                   10                  15

Met Arg Ile Ala Leu Ser Arg Pro Asn Val Glu Val Val Ala Leu Asn
            20                  25                  30

Asp Pro Phe Ile Thr Asn Asp Tyr Ala Ala Tyr Met Phe Lys Tyr Asp
        35                  40                  45

Ser Thr His Gly Arg Tyr Ala Gly Glu Val Ser His Asp Asp Lys His
    50                  55                  60

Ile Ile Val Asp Gly Lys Lys Ile Ala Thr Tyr Gln Glu Arg Asp Pro
65                  70                  75                  80

Ala Asn Leu Pro Trp Gly Ser Ser Asn Val Asp Ile Ala Ile Asp Ser
                85                  90                  95

Thr Gly Val Phe Lys Glu Leu Asp Thr Ala Gln Lys His Ile Asp Ala
            100                 105                 110

Gly Ala Lys Lys Val Val Ile Thr Ala Pro Ser Ser Thr Ala Pro Met
        115                 120                 125

Phe Val Met Gly Val Asn Glu Val Lys Tyr Thr Ser Asp Leu Lys Ile
    130                 135                 140

Val Ser Asn Ala Ser Cys Thr Thr Asn Cys Leu Ala Pro Leu Ala Lys
145                 150                 155                 160

Val Ile Asn Asp Ala Phe Gly Ile Glu Glu Gly Leu Met Thr Thr Val
                165                 170                 175

His Ser Leu Thr Ala Thr Gln Lys Thr Val Asp Gly Pro Ser His Lys
            180                 185                 190

Asp Trp Arg Gly Gly Arg Thr Ala Ser Gly Asn Ile Ile Pro Ser Ser
        195                 200                 205

Thr Gly Ala Ala Lys Ala Val Gly Lys Val Leu Pro Glu Leu Gln Gly
    210                 215                 220

Lys Leu Thr Gly Met Ala Phe Arg Val Pro Thr Val Asp Val Ser Val
225                 230                 235                 240

Val Asp Leu Thr Val Lys Leu Asp Lys Glu Thr Thr Tyr Asp Glu Ile
                245                 250                 255

Lys Lys Val Val Lys Ala Ala Ala Glu Gly Lys Leu Lys Gly Val Leu
```

```
                          260                 265                 270
Gly Tyr Thr Glu Asp Ala Val Val Ser Ser Asp Phe Leu Gly Asp Ser
            275                 280                 285

His Ser Ser Ile Phe Asp Ala Ser Ala Gly Ile Gln Leu Ser Pro Lys
            290                 295                 300

Phe Val Lys Leu Val Ser Trp Tyr Asp Asn Glu Tyr Gly Tyr Ser Thr
305                 310                 315                 320

Arg Val Val Asp Leu Val Glu His Ile Ala Lys Ala
                325                 330

<210> SEQ ID NO 58
<211> LENGTH: 335
<212> TYPE: PRT
<213> ORGANISM: Schizosaccharomyces pombe
<220> FEATURE:
<221> NAME/KEY: MISC_FEATURE
<222> LOCATION: (1)..(335)
<223> OTHER INFORMATION: GenBank Accession No. NP_595236

<400> SEQUENCE: 58

Met Ala Ile Pro Lys Val Gly Ile Asn Gly Phe Gly Arg Ile Gly Arg
1               5                   10                  15

Ile Val Leu Arg Asn Ala Ile Leu Thr Gly Lys Ile Gln Val Val Ala
                20                  25                  30

Val Asn Asp Pro Phe Ile Asp Leu Asp Tyr Met Ala Tyr Met Phe Lys
            35                  40                  45

Tyr Asp Ser Thr His Gly Arg Phe Glu Gly Ser Val Glu Thr Lys Gly
        50                  55                  60

Gly Lys Leu Val Ile Asp Gly His Ser Ile Asp Val His Asn Glu Arg
65                  70                  75                  80

Asp Pro Ala Asn Ile Lys Trp Ser Ala Ser Gly Ala Glu Tyr Val Ile
                85                  90                  95

Glu Ser Thr Gly Val Phe Thr Thr Lys Glu Thr Ala Ser Ala His Leu
            100                 105                 110

Lys Gly Gly Ala Lys Arg Val Ile Ile Ser Ala Pro Ser Lys Asp Ala
        115                 120                 125

Pro Met Phe Val Val Gly Val Asn Leu Glu Lys Phe Asn Pro Ser Glu
    130                 135                 140

Lys Val Ile Ser Asn Ala Ser Cys Thr Thr Asn Cys Leu Ala Pro Leu
145                 150                 155                 160

Ala Lys Val Ile Asn Asp Thr Phe Gly Ile Glu Glu Gly Leu Met Thr
                165                 170                 175

Thr Val His Ala Thr Thr Ala Thr Gln Lys Thr Val Asp Gly Pro Ser
            180                 185                 190

Lys Lys Asp Trp Arg Gly Gly Arg Gly Ala Ser Ala Asn Ile Ile Pro
        195                 200                 205

Ser Ser Thr Gly Ala Ala Lys Ala Val Gly Lys Val Ile Pro Ala Leu
    210                 215                 220

Asn Gly Lys Leu Thr Gly Met Ala Phe Arg Val Pro Thr Pro Asp Val
225                 230                 235                 240

Ser Val Val Asp Leu Thr Val Lys Leu Ala Lys Pro Thr Asn Tyr Glu
                245                 250                 255

Asp Ile Lys Ala Ala Ile Lys Ala Ala Ser Glu Gly Pro Met Lys Gly
            260                 265                 270

Val Leu Gly Tyr Thr Glu Asp Ser Val Val Ser Thr Asp Phe Cys Gly
        275                 280                 285
```

```
Asp Asn His Ser Ser Ile Phe Asp Ala Ser Ala Gly Ile Gln Leu Ser
        290                 295                 300

Pro Gln Phe Val Lys Leu Val Ser Trp Tyr Asp Asn Glu Trp Gly Tyr
305                 310                 315                 320

Ser His Arg Val Val Asp Leu Val Ala Tyr Thr Ala Ser Lys Asp
                325                 330                 335

<210> SEQ ID NO 59
<211> LENGTH: 338
<212> TYPE: PRT
<213> ORGANISM: Aspergillus oryzae
<220> FEATURE:
<221> NAME/KEY: MISC_FEATURE
<222> LOCATION: (1)..(338)
<223> OTHER INFORMATION: GenBank Accession No. AAK08065

<400> SEQUENCE: 59

Met Ala Thr Pro Lys Val Gly Ile Asn Gly Phe Gly Arg Ile Gly Arg
1               5                   10                  15

Ile Val Phe Arg Asn Ala Ile Ala Ser Gly Asp Val Asp Val Val Ala
                20                  25                  30

Val Asn Asp Pro Phe Ile Glu Thr His Tyr Ala Ala Tyr Met Leu Lys
            35                  40                  45

Tyr Asp Ser Thr His Gly Arg Phe Gln Gly Thr Ile Glu Thr Tyr Asp
    50                  55                  60

Glu Gly Leu Ile Val Asn Gly Lys Lys Ile Arg Phe Phe Ala Glu Arg
65                  70                  75                  80

Asp Pro Ala Ala Ile Pro Trp Gly Ser Ala Gly Ala Ala Tyr Ile Val
                85                  90                  95

Glu Ser Thr Gly Val Phe Thr Thr Thr Glu Lys Ala Ser Ala His Leu
            100                 105                 110

Lys Gly Gly Ala Lys Lys Val Ile Ile Ser Ala Pro Ser Ala Asp Ala
        115                 120                 125

Pro Met Phe Val Met Gly Val Asn Asn Lys Glu Tyr Lys Thr Asp Ile
    130                 135                 140

Asn Val Leu Ser Asn Ala Ser Cys Thr Thr Asn Cys Leu Ala Pro Leu
145                 150                 155                 160

Ala Lys Val Ile Asn Asp Asn Phe Gly Leu Val Glu Gly Leu Met Thr
                165                 170                 175

Thr Val His Ser Tyr Thr Ala Thr Gln Lys Thr Val Asp Ala Pro Ser
            180                 185                 190

Ala Lys Asp Trp Arg Gly Gly Arg Thr Ala Ala Gln Asn Ile Ile Pro
        195                 200                 205

Ser Ser Thr Gly Ala Ala Lys Ala Val Gly Lys Val Ile Pro Ser Leu
    210                 215                 220

Asn Gly Lys Leu Thr Gly Met Ser Met Arg Val Pro Thr Ala Asn Val
225                 230                 235                 240

Ser Val Val Asp Leu Thr Cys Arg Thr Glu Lys Ala Val Thr Tyr Glu
                245                 250                 255

Asp Ile Lys Lys Thr Ile Lys Ala Ala Ser Glu Glu Gly Glu Leu Lys
            260                 265                 270

Gly Ile Leu Gly Tyr Thr Glu Asp Asp Ile Val Ser Thr Asp Leu Ile
        275                 280                 285

Gly Asp Ala His Ser Ser Ile Phe Asp Ala Lys Ala Gly Ile Ala Leu
    290                 295                 300

Asn Glu His Phe Ile Lys Leu Val Ser Trp Tyr Asp Asn Glu Trp Gly
305                 310                 315                 320
```

```
Tyr Ser Arg Arg Val Val Asp Leu Ile Ala Tyr Ile Ser Lys Val Asp
            325                 330                 335

Gly Gln

<210> SEQ ID NO 60
<211> LENGTH: 333
<212> TYPE: PRT
<213> ORGANISM: Paralichthys olivaceus
<220> FEATURE:
<221> NAME/KEY: MISC_FEATURE
<222> LOCATION: (1)..(333)
<223> OTHER INFORMATION: GenBank Accession No. BAA88638

<400> SEQUENCE: 60

Met Val Lys Val Gly Ile Asn Gly Phe Gly Arg Ile Gly Arg Leu Val
1               5                   10                  15

Thr Arg Ala Ala Phe Thr Ser Lys Lys Val Glu Ile Val Ala Ile Asn
            20                  25                  30

Asp Pro Phe Ile Asp Leu Glu Tyr Met Val Tyr Met Phe Lys Tyr Asp
        35                  40                  45

Ser Thr His Gly Arg Phe Lys Gly Glu Val Lys Ile Glu Gly Asp Lys
    50                  55                  60

Leu Val Ile Asp Gly His Lys Ile Thr Val Phe His Glu Arg Asp Pro
65                  70                  75                  80

Thr Asn Ile Lys Trp Gly Asp Ala Gly Ala His Tyr Val Val Glu Ser
                85                  90                  95

Thr Gly Val Phe Thr Thr Ile Glu Lys Ala Ser Ala His Leu Lys Gly
            100                 105                 110

Gly Ala Lys Lys Val Ile Ile Ser Ala Pro Ser Ala Asp Ala Pro Met
        115                 120                 125

Phe Val Met Gly Val Asn His Glu Lys Tyr Asp Lys Ser Leu Gln Val
    130                 135                 140

Val Ser Asn Ala Ser Cys Thr Thr Asn Cys Leu Ala Pro Leu Ala Lys
145                 150                 155                 160

Val Ile Asn Asp Asn Phe Gly Ile Ile Glu Gly Leu Met Ser Thr Val
                165                 170                 175

His Ala Ile Thr Ala Thr Gln Lys Thr Val Asp Gly Pro Ser Gly Lys
            180                 185                 190

Leu Trp Arg Asp Gly Arg Gly Ala Ser Gln Asn Ile Ile Pro Ala Ser
        195                 200                 205

Thr Gly Ala Ala Lys Ala Val Gly Lys Val Ile Pro Glu Leu Asn Gly
    210                 215                 220

Lys Leu Thr Gly Met Ala Phe Arg Val Pro Thr Pro Asn Val Ser Val
225                 230                 235                 240

Val Asp Leu Thr Val Arg Leu Glu Lys Pro Ala Ser Tyr Glu Asn Ile
                245                 250                 255

Lys Lys Val Val Lys Ala Ala Ala Glu Gly Pro Met Lys Gly Tyr Leu
            260                 265                 270

Ala Tyr Thr Glu His Gln Val Val Ser Thr Asp Phe Asn Gly Asp Thr
        275                 280                 285

His Ser Ser Ile Phe Asp Ala Gly Ala Gly Ile Ala Leu Asn Asp His
    290                 295                 300

Phe Val Lys Leu Val Ser Trp Tyr Asp Asn Glu Phe Gly Tyr Ser Asn
305                 310                 315                 320

Arg Val Cys Asp Leu Met Ala His Met Ala Ser Lys Glu
                325                 330
```

```
<210> SEQ ID NO 61
<211> LENGTH: 333
<212> TYPE: PRT
<213> ORGANISM: Xenopus laevis
<220> FEATURE:
<221> NAME/KEY: MISC_FEATURE
<222> LOCATION: (1)..(333)
<223> OTHER INFORMATION: GenBank Accession No. P51469

<400> SEQUENCE: 61

Met Val Lys Val Gly Ile Asn Gly Phe Gly Cys Ile Gly Arg Leu Val
1               5                   10                  15

Thr Arg Ala Ala Phe Asp Ser Gly Lys Val Gln Val Val Ala Ile Asn
            20                  25                  30

Asp Pro Phe Ile Asp Leu Asp Tyr Met Val Tyr Met Phe Lys Tyr Asp
        35                  40                  45

Ser Thr His Gly Arg Phe Lys Gly Thr Val Lys Ala Glu Asn Gly Lys
    50                  55                  60

Leu Ile Ile Asn Asp Gln Val Ile Thr Val Phe Gln Glu Arg Asp Pro
65                  70                  75                  80

Ser Ser Ile Lys Trp Gly Asp Ala Gly Ala Val Tyr Val Val Glu Ser
                85                  90                  95

Thr Gly Val Phe Thr Thr Thr Glu Lys Ala Ser Leu His Leu Lys Gly
            100                 105                 110

Gly Ala Lys Arg Val Val Ile Ser Ala Pro Ser Ala Asp Ala Pro Met
        115                 120                 125

Phe Val Val Gly Val Asn His Glu Lys Tyr Glu Asn Ser Leu Lys Val
    130                 135                 140

Val Ser Asn Ala Ser Cys Thr Thr Asn Cys Leu Ala Pro Leu Ala Lys
145                 150                 155                 160

Val Ile Asn Asp Asn Phe Gly Ile Val Glu Gly Leu Met Thr Thr Val
                165                 170                 175

His Ala Phe Thr Ala Thr Gln Lys Thr Val Asp Gly Pro Ser Gly Lys
            180                 185                 190

Leu Trp Arg Asp Gly Arg Gly Ala Gly Gln Asn Ile Ile Pro Ala Ser
        195                 200                 205

Thr Gly Ala Ala Lys Ala Val Gly Lys Val Ile Pro Glu Leu Asn Gly
    210                 215                 220

Lys Ile Thr Gly Met Ala Phe Arg Val Pro Thr Pro Asn Val Ser Val
225                 230                 235                 240

Val Asp Leu Thr Cys Arg Leu Gln Lys Pro Ala Lys Tyr Asp Asp Ile
                245                 250                 255

Lys Ala Ala Ile Lys Thr Ala Ser Glu Gly Pro Met Lys Gly Ile Leu
            260                 265                 270

Gly Tyr Thr Gln Asp Gln Val Val Ser Thr Asp Phe Asn Gly Asp Thr
        275                 280                 285

His Ser Ser Ile Phe Asp Ala Asp Ala Gly Ile Ala Leu Asn Glu Asn
    290                 295                 300

Phe Val Lys Leu Val Ser Trp Tyr Asp Asn Glu Cys Gly Tyr Ser Asn
305                 310                 315                 320

Arg Val Val Asp Leu Val Cys His Met Ala Ser Lys Glu
                325                 330

<210> SEQ ID NO 62
<211> LENGTH: 333
<212> TYPE: PRT
```

<213> ORGANISM: Gallus gallus
<220> FEATURE:
<221> NAME/KEY: MISC_FEATURE
<222> LOCATION: (1)..(333)
<223> OTHER INFORMATION: GenBank Accession No. DECHG3

<400> SEQUENCE: 62

```
Met Val Lys Val Gly Val Asn Gly Phe Gly Arg Ile Gly Arg Leu Val
1               5                   10                  15

Thr Arg Ala Ala Val Leu Ser Gly Lys Val Gln Val Val Ala Ile Asn
            20                  25                  30

Asp Pro Phe Ile Asp Leu Asn Tyr Met Val Tyr Met Phe Lys Tyr Asp
        35                  40                  45

Ser Thr His Gly His Phe Lys Gly Thr Val Leu Ala Glu Asn Gly Lys
    50                  55                  60

Leu Val Ile Asn Gly His Ala Ile Thr Ile Phe Gln Glu Arg Asp Pro
65                  70                  75                  80

Ser Asn Ile Lys Trp Ala Asp Ala Gly Ala Glu Tyr Val Val Glu Ser
                85                  90                  95

Thr Gly Val Phe Thr Thr Met Glu Lys Ala Gly Ala His Leu Lys Gly
            100                 105                 110

Gly Ala Lys Arg Val Ile Ile Ser Ala Pro Ser Ala Asp Ala Pro Met
        115                 120                 125

Phe Val Met Gly Val Asn His Glu Lys Tyr Asp Lys Ser Leu Lys Ile
    130                 135                 140

Val Ser Asn Ala Ser Cys Thr Thr Asn Cys Leu Ala Pro Leu Ala Lys
145                 150                 155                 160

Val Ile His Asp Asn Phe Gly Ile Val Glu Gly Leu Met Thr Thr Val
                165                 170                 175

His Ala Ile Thr Ala Thr Gln Lys Thr Val Asp Gly Pro Ser Gly Lys
            180                 185                 190

Leu Trp Arg Asp Gly Arg Gly Ala Ala Gln Asn Ile Ile Pro Ala Ser
        195                 200                 205

Thr Gly Ala Ala Lys Ala Val Gly Lys Val Ile Pro Glu Leu Asn Gly
    210                 215                 220

Lys Leu Thr Gly Met Ala Phe Arg Val Pro Thr Pro Asn Val Ser Val
225                 230                 235                 240

Val Asp Leu Thr Cys Arg Leu Glu Lys Pro Ala Lys Tyr Asp Asp Ile
                245                 250                 255

Lys Arg Val Val Lys Ala Ala Ala Asp Gly Pro Leu Lys Gly Ile Leu
            260                 265                 270

Gly Tyr Thr Glu Asp Gln Val Val Ser Cys Asp Phe Asn Gly Asp Ser
        275                 280                 285

His Ser Ser Thr Phe Asp Ala Gly Ala Gly Ile Ala Leu Asn Asp His
    290                 295                 300

Phe Val Lys Leu Val Ser Trp Tyr Asp Asn Glu Phe Gly Tyr Ser Asn
305                 310                 315                 320

Arg Val Val Asp Leu Met Val His Met Ala Ser Lys Glu
                325                 330
```

<210> SEQ ID NO 63
<211> LENGTH: 7
<212> TYPE: PRT
<213> ORGANISM: Artificial Sequence
<220> FEATURE:
<223> OTHER INFORMATION: Consensus GPD sequence

<400> SEQUENCE: 63

```
Lys Tyr Asp Ser Thr His Gly
1               5
```

```
<210> SEQ ID NO 64
<211> LENGTH: 7
<212> TYPE: PRT
<213> ORGANISM: Artificial Sequence
<220> FEATURE:
<223> OTHER INFORMATION: Consensus GPD sequence

<400> SEQUENCE: 64
```

```
Thr Gly Ala Ala Lys Ala Val
1               5
```

```
<210> SEQ ID NO 65
<211> LENGTH: 20
<212> TYPE: DNA
<213> ORGANISM: Artificial Sequence
<220> FEATURE:
<223> OTHER INFORMATION: Primer YL193

<400> SEQUENCE: 65
```
aagtacgayt cbacycaygg                                                  20

```
<210> SEQ ID NO 66
<211> LENGTH: 20
<212> TYPE: DNA
<213> ORGANISM: Artificial Sequence
<220> FEATURE:
<223> OTHER INFORMATION: Primer YL194

<400> SEQUENCE: 66
```
acrgccttrg crgcdccrgt                                                  20

```
<210> SEQ ID NO 67
<211> LENGTH: 507
<212> TYPE: DNA
<213> ORGANISM: Yarrowia lipolytica

<400> SEQUENCE: 67
```
aagtacgact ccacccacgg ccgattcaag ggcaaggtcg aggccaagga cggcggtctg      60
atcatcgacg gcaagcacat ccaggtcttc ggtgagcgag acccctccaa catccctgg      120 ggtaaggccg gtgccgacta cgttgtcgag tccaccggtg tcttcaccgg caaggaggct    180
gcctccgccc acctcaaggg tggtgccaag aaggtcatca tctccgcccc ctccggtgac    240
gcccccatgt tcgttgtcgg tgtcaacctc gacgcctaca gcccgacat gaccgtcatc     300 tccaacgctt cttgtaccac caactgtctg gctcccttg ccaaggttgt caacgacaag    360
tacggaatca ttgagggtct catgaccacc gtccactcca tcaccgccac ccagaagacc    420
gttgacggtc cttcccacaa ggactggcga ggtggccgaa ccgcctctgg taacatcatc    480
ccctcttcca ccggagccgc caaggct                                        507

```
<210> SEQ ID NO 68
<211> LENGTH: 169
<212> TYPE: PRT
<213> ORGANISM: Yarrowia lipolytica

<400> SEQUENCE: 68
```

```
Lys Tyr Asp Ser Thr His Gly Arg Phe Lys Gly Lys Val Glu Ala Lys
1               5                   10                  15

Asp Gly Gly Leu Ile Ile Asp Gly Lys His Ile Gln Val Phe Gly Glu
            20                  25                  30
```

```
Arg Asp Pro Ser Asn Ile Pro Trp Gly Lys Ala Gly Ala Asp Tyr Val
            35                  40                  45
Val Glu Ser Thr Gly Val Phe Thr Gly Lys Glu Ala Ala Ser Ala His
 50                  55                  60
Leu Lys Gly Gly Ala Lys Lys Val Ile Ile Ser Ala Pro Ser Gly Asp
 65                  70                  75                  80
Ala Pro Met Phe Val Gly Val Asn Leu Asp Ala Tyr Lys Pro Asp
                 85                  90                  95
Met Thr Val Ile Ser Asn Ala Ser Cys Thr Thr Asn Cys Leu Ala Pro
            100                 105                 110
Leu Ala Lys Val Val Asn Asp Lys Tyr Gly Ile Ile Glu Gly Leu Met
            115                 120                 125
Thr Thr Val His Ser Ile Thr Ala Thr Gln Lys Thr Val Asp Gly Pro
            130                 135                 140
Ser His Lys Asp Trp Arg Gly Gly Arg Thr Ala Ser Gly Asn Ile Ile
145                 150                 155                 160
Pro Ser Ser Thr Gly Ala Ala Lys Ala
                165
```

<210> SEQ ID NO 69
<211> LENGTH: 26
<212> TYPE: DNA
<213> ORGANISM: Artificial Sequence
<220> FEATURE:
<223> OTHER INFORMATION: Primer YL206

<400> SEQUENCE: 69
ccttgccggt gaagacaccg gtggac                                          26

<210> SEQ ID NO 70
<211> LENGTH: 28
<212> TYPE: DNA
<213> ORGANISM: Artificial Sequence
<220> FEATURE:
<223> OTHER INFORMATION: Primer YL207

<400> SEQUENCE: 70
gaagacctgg atgtgcttgc cgtcgatg                                        28

<210> SEQ ID NO 71
<211> LENGTH: 24
<212> TYPE: DNA
<213> ORGANISM: Artificial Sequence
<220> FEATURE:
<223> OTHER INFORMATION: Primer YL208

<400> SEQUENCE: 71
gaccttgccc ttgaatcggc cgtg                                            24

<210> SEQ ID NO 72
<211> LENGTH: 1848
<212> TYPE: DNA
<213> ORGANISM: Yarrowia lipolytica

<400> SEQUENCE: 72
gtgattgcct ctgaatactt tcaacaagtt acacccttcg cggcgacgat ctacagcccg      60
atcacatgaa cttttggccga gggatgatgt aatcgagtat cgtggtagtt caatacgtac    120
atgtacgatg ggtgcctcaa ttgtgcgata ctactacaag tgcagcacgc tcgtgcccgt    180 acccttactttt gtcggacgtc cctgctccct cgttcaacat ctcaagctca acaatcagtg   240

-continued

```
ttggacactg caacgctagc agccggtacg tggctttagc cccatgctcc atgctccatg    300
ctccatgctc tgggcctatg agctagccgt ttggcgcaca tagcatagtg acatgtcgat    360
caagtcaaag tcgaggtgtg gaaaacgggc tgcgggtcgc caggggcctc acaagcgcct    420
ccaccgcaga cgcccacctc gttagcgtcc attgcgatcg tctcggtaca tttggttaca    480
ttttgcgaca ggttgaaatg aatcggccga cgctcggtag tcggaaagag ccgggaccgg    540
ccggcgagca taaaccggac gcagtaggat gtcctgcacg ggtcttttg tggggtgtgg     600 agaaagggt gcttggagat ggaagccggt agaaccgggc tgcttgtgct tggagatgga     660
agccggtaga accgggctgc ttgggggat ttggggccgc tgggctccaa agaggggtag     720
gcatttcgtt ggggttacgt aattgcggca tttgggtcct gcgcgcatgt cccattggtc    780
agaattagtc cggataggag acttatcagc caatcacagc gccggatcca cctgtaggtt    840
gggttgggtg ggagcacccc tccacagagt agagtcaaac agcagcagca acatgatagt    900
tgggggtgtg cgtgttaaag gaaaaaaaag aagcttgggt tatattcccg ctctatttag    960
aggttgcggg atagacgccg acggagggca atggcgccat ggaaccttgc ggatatcgat   1020
acgccgcggc ggactgcgtc cgaaccagct ccagcagcgt ttttccgggg ccattgagcc    1080
gactgcgacc ccgccaacgt gtcttggccc acgcactcat gtcatgttgg tgttgggagg   1140
ccacttttta agtagcacaa ggcacctagc tcgcagcaag gtgtccgaac caaagaagcg   1200
gctgcagtgg tgcaaacggg gcggaaacgg cgggaaaaag ccacgggggc acgaattgag   1260
gcacgccctc gaatttgaga cgagtcacgg ccccattcgc ccgcgcaatg gctcgccaac   1320
gcccggtctt ttgcaccaca tcaggttacc ccaagccaaa cctttgtgtt aaaaagctta   1380
acatattata ccgaacgtag gtttgggcgg gcttgctccg tctgtccaag gcaacattta   1440
tataagggtc tgcatcgccg gctcaattga atcttttttc ttcttctctt ctctatattc   1500
attcttgaat taaacacaca tcaacatggc catcaaagtc ggtattaacg gattcgggcg   1560
aatcggacga attgtgagta ccatagaagg tgatggaaac atgacccaac agaaacagat   1620
gacaagtgtc atcgacccac cagagcccaa ttgagctcat actaacagtc gacaacctgt   1680
cgaaccaatt gatgactccc cgacaatgta ctaacacagg tcctgcgaaa cgctctcaag   1740
aaccctgagg tcgaggtcgt cgctgtgaac gaccccttca tcgacaccga gtacgctgct   1800
tacatgttca agtacgactc cacccacggc cgattcaagg gcaaggtc                 1848
```

<210> SEQ ID NO 73
<211> LENGTH: 24
<212> TYPE: DNA
<213> ORGANISM: Artificial Sequence
<220> FEATURE:
<223> OTHER INFORMATION: Primer P145

<400> SEQUENCE: 73
agactccatg gaacggtctc tttc                        24

<210> SEQ ID NO 74
<211> LENGTH: 26
<212> TYPE: DNA
<213> ORGANISM: Artificial Sequence
<220> FEATURE:
<223> OTHER INFORMATION: Primer P146

<400> SEQUENCE: 74
cttagcggcc gcttactcaa tcattc                      26

<210> SEQ ID NO 75

```
<211> LENGTH: 35
<212> TYPE: DNA
<213> ORGANISM: Artificial Sequence
<220> FEATURE:
<223> OTHER INFORMATION: Primer YPDAT5

<400> SEQUENCE: 75
atgcgcggcc gcacaatgac acaacctgtg aatcg                               35

<210> SEQ ID NO 76
<211> LENGTH: 34
<212> TYPE: DNA
<213> ORGANISM: Artificial Sequence
<220> FEATURE:
<223> OTHER INFORMATION: Primer YPDAT3

<400> SEQUENCE: 76
gatcgcggcc gcctaattgc tgccgagatc aatc                                34

<210> SEQ ID NO 77
<211> LENGTH: 25
<212> TYPE: DNA
<213> ORGANISM: Artificial Sequence
<220> FEATURE:
<223> OTHER INFORMATION: LinkAmp Primer 2

<400> SEQUENCE: 77
gcctctgaat actttcaaca agtta                                          25

<210> SEQ ID NO 78
<211> LENGTH: 459
<212> TYPE: PRT
<213> ORGANISM: Yarrowia lipolytica

<400> SEQUENCE: 78
```

Met Leu Cys Cys Ala Ile Pro Leu Leu Trp Pro Phe Val Ile Ala Tyr
1               5                   10                  15

Val Val Tyr Ala Val Lys Asp Asp Ser Pro Ser Asn Gly Gly Val Val
                20                  25                  30

Lys Arg Tyr Ser Pro Ile Ser Arg Asn Phe Phe Ile Trp Lys Leu Phe
            35                  40                  45

Gly Arg Tyr Phe Pro Ile Thr Leu His Lys Thr Val Asp Leu Glu Pro
        50                  55                  60

Thr His Thr Tyr Tyr Pro Leu Asp Val Gln Glu Tyr His Leu Ile Ala
65                  70                  75                  80

Glu Arg Tyr Trp Pro Gln Asn Lys Tyr Leu Arg Ala Ile Ile Ser Thr
                85                  90                  95

Ile Glu Tyr Phe Leu Pro Ala Phe Met Lys Arg Ser Leu Ser Ile Asn
            100                 105                 110

Glu Gln Glu Gln Pro Ala Glu Arg Asp Pro Leu Leu Ser Pro Val Ser
        115                 120                 125

Pro Ser Ser Pro Gly Ser Gln Pro Asp Lys Trp Ile Asn His Asp Ser
130                 135                 140

Arg Tyr Ser Arg Gly Glu Ser Ser Gly Ser Asn Gly His Ala Ser Gly
145                 150                 155                 160

Ser Glu Leu Asn Gly Asn Gly Asn Asn Gly Thr Thr Asn Arg Arg Pro
                165                 170                 175

Leu Ser Ser Ala Ser Ala Gly Ser Thr Ala Ser Asp Ser Thr Leu Leu
            180                 185                 190

Asn Gly Ser Leu Asn Ser Tyr Ala Asn Gln Ile Ile Gly Glu Asn Asp
        195                 200                 205

-continued

```
Pro Gln Leu Ser Pro Thr Lys Leu Lys Pro Thr Gly Arg Lys Tyr Ile
    210                 215                 220

Phe Gly Tyr His Pro His Gly Ile Ile Gly Met Gly Ala Phe Gly Gly
225                 230                 235                 240

Ile Ala Thr Glu Gly Ala Gly Trp Ser Lys Leu Phe Pro Gly Ile Pro
                245                 250                 255

Val Ser Leu Met Thr Leu Thr Asn Asn Phe Arg Val Pro Leu Tyr Arg
            260                 265                 270

Glu Tyr Leu Met Ser Leu Gly Val Ala Ser Val Ser Lys Lys Ser Cys
        275                 280                 285

Lys Ala Leu Leu Lys Arg Asn Gln Ser Ile Cys Ile Val Val Gly Gly
    290                 295                 300

Ala Gln Glu Ser Leu Leu Ala Arg Pro Gly Val Met Asp Leu Val Leu
305                 310                 315                 320

Leu Lys Arg Lys Gly Phe Val Arg Leu Gly Met Glu Val Gly Asn Val
                325                 330                 335

Ala Leu Val Pro Ile Met Ala Phe Gly Glu Asn Asp Leu Tyr Asp Gln
            340                 345                 350

Val Ser Asn Asp Lys Ser Ser Lys Leu Tyr Arg Phe Gln Gln Phe Val
        355                 360                 365

Lys Asn Phe Leu Gly Phe Thr Leu Pro Leu Met His Ala Arg Gly Val
    370                 375                 380

Phe Asn Tyr Asp Val Gly Leu Val Pro Tyr Arg Arg Pro Val Asn Ile
385                 390                 395                 400

Val Val Gly Ser Pro Ile Asp Leu Pro Tyr Leu Pro His Pro Thr Asp
                405                 410                 415

Glu Glu Val Ser Glu Tyr His Asp Arg Tyr Ile Ala Glu Leu Gln Arg
            420                 425                 430

Ile Tyr Asn Glu His Lys Asp Glu Tyr Phe Ile Asp Trp Thr Glu Glu
        435                 440                 445

Gly Lys Gly Ala Pro Glu Phe Arg Met Ile Glu
    450                 455

<210> SEQ ID NO 79
<211> LENGTH: 355
<212> TYPE: PRT
<213> ORGANISM: Yarrowia lipolytica

<400> SEQUENCE: 79

Met Lys Arg Ser Leu Ser Ile Asn Glu Gln Glu Gln Pro Ala Glu Arg
1               5                   10                  15

Asp Pro Leu Leu Ser Pro Val Ser Pro Ser Pro Gly Ser Gln Pro
            20                  25                  30

Asp Lys Trp Ile Asn His Asp Ser Arg Tyr Ser Arg Gly Glu Ser Ser
            35                  40                  45

Gly Ser Asn Gly His Ala Ser Gly Ser Glu Leu Asn Gly Asn Gly Asn
        50                  55                  60

Asn Gly Thr Thr Asn Arg Arg Pro Leu Ser Ser Ala Ser Ala Gly Ser
65                  70                  75                  80

Thr Ala Ser Asp Ser Thr Leu Leu Asn Gly Ser Leu Asn Ser Tyr Ala
                85                  90                  95

Asn Gln Ile Ile Gly Glu Asn Asp Pro Gln Leu Ser Pro Thr Lys Leu
            100                 105                 110

Lys Pro Thr Gly Arg Lys Tyr Ile Phe Gly Tyr His Pro His Gly Ile
        115                 120                 125
```

```
Ile Gly Met Gly Ala Phe Gly Gly Ile Ala Thr Glu Gly Ala Gly Trp
    130                 135                 140

Ser Lys Leu Phe Pro Gly Ile Pro Val Ser Leu Met Thr Leu Thr Asn
145                 150                 155                 160

Asn Phe Arg Val Pro Leu Tyr Arg Glu Tyr Leu Met Ser Leu Gly Val
                165                 170                 175

Ala Ser Val Ser Lys Lys Ser Cys Lys Ala Leu Leu Lys Arg Asn Gln
                180                 185                 190

Ser Ile Cys Ile Val Val Gly Ala Gln Glu Ser Leu Leu Ala Arg
        195                 200                 205

Pro Gly Val Met Asp Leu Val Leu Leu Lys Arg Lys Gly Phe Val Arg
210                 215                 220

Leu Gly Met Glu Val Gly Asn Val Ala Leu Val Pro Ile Met Ala Phe
225                 230                 235                 240

Gly Glu Asn Asp Leu Tyr Asp Gln Val Ser Asn Asp Lys Ser Ser Lys
                245                 250                 255

Leu Tyr Arg Phe Gln Gln Phe Val Lys Asn Phe Leu Gly Phe Thr Leu
                260                 265                 270

Pro Leu Met His Ala Arg Gly Val Phe Asn Tyr Asp Val Gly Leu Val
                275                 280                 285

Pro Tyr Arg Arg Pro Val Asn Ile Val Val Gly Ser Pro Ile Asp Leu
        290                 295                 300

Pro Tyr Leu Pro His Pro Thr Asp Glu Glu Val Ser Glu Tyr His Asp
305                 310                 315                 320

Arg Tyr Ile Ala Glu Leu Gln Arg Ile Tyr Asn Glu His Lys Asp Glu
                325                 330                 335

Tyr Phe Ile Asp Trp Thr Glu Glu Gly Lys Gly Ala Pro Glu Phe Arg
                340                 345                 350

Met Ile Glu
        355

<210> SEQ ID NO 80
<211> LENGTH: 27
<212> TYPE: DNA
<213> ORGANISM: Artificial Sequence
<220> FEATURE:
<223> OTHER INFORMATION: Primer GPD-1

<400> SEQUENCE: 80
tcgagtttat cattatcaat actcgcc                                      27

<210> SEQ ID NO 81
<211> LENGTH: 29
<212> TYPE: DNA
<213> ORGANISM: Artificial Sequence
<220> FEATURE:
<223> OTHER INFORMATION: Primer GPD-2

<400> SEQUENCE: 81
tcgaaactaa gttcttggtg ttttaaaac                                    29

<210> SEQ ID NO 82
<211> LENGTH: 31
<212> TYPE: DNA
```

<213> ORGANISM: Artificial Sequence
<220> FEATURE:
<223> OTHER INFORMATION: Primer ADHT-1

<400> SEQUENCE: 82
gatcctcgag taagcgaatt tcttatgatt t                                31

<210> SEQ ID NO 83
<211> LENGTH: 31
<212> TYPE: DNA
<213> ORGANISM: Artificial Sequence
<220> FEATURE:
<223> OTHER INFORMATION: Primer ADHT-2

<400> SEQUENCE: 83
gatcggtacc acaggtgttg tcctctgagg a                                31

<210> SEQ ID NO 84
<211> LENGTH: 81
<212> TYPE: DNA
<213> ORGANISM: Artificial Sequence
<220> FEATURE:
<223> OTHER INFORMATION: Primer UP 161

<400> SEQUENCE: 84
aaaggttctc taccaacgaa ttcggcgaca atcgagtaaa aaatggaaca cacaggggcg    60
ctatcgcaca gaatcaaatt c                                            81

<210> SEQ ID NO 85
<211> LENGTH: 81
<212> TYPE: DNA
<213> ORGANISM: Artificial Sequence
<220> FEATURE:
<223> OTHER INFORMATION: Primer LP 162

<400> SEQUENCE: 85
ttgaaataat acacggatgg atagtgagtc aatgtcggtc atttatgaag aggaggtcga    60
ctacgtcgtt aaggccgttt c                                            81

<210> SEQ ID NO 86
<211> LENGTH: 1068
<212> TYPE: DNA
<213> ORGANISM: Yarrowia lipolytica

<400> SEQUENCE: 86
atgaaacggt ctctttctat caacgagcag gagcagcctg ccgagcgaga tcctctcctg    60
tctcccgttt ctcccagctc tccgggttct caacctgaca agtggattaa ccacgacagc   120
agatatagcc gtggagaatc atctggctcc aacggccacg cctcgggctc cgaacttaac   180
ggcaacggca acaatggcac cactaaccga cgacctttgt cgtccgcctc tgctggctcc   240
actgcatctg attccacgct tcttaacggg tccctcaact cctacgccaa ccagatcatt   300
ggcgaaaacg acccacagct gtcgcccaca aaactcaagc ccactggcag aaaatacatc   360
ttcggctacc accccacgg cattatcggc atgggagcct tggtggaat tgccaccgag   420 ggagctggat ggtccaagct cttttccggc atccctgttt ctcttatgac tctcaccaac   480
aacttccgag tgcctctcta cagagagtac ctcatgagtc tgggagtcgc ttctgtctcc   540
aagaagtcct gcaaggccct cctcaagcga aaccagtcta tctgcattgt cgttggtgga   600
gcacaggaaa gtcttctggc cagacccggt gtcatggacc tggtgctact caagcgaaag   660
ggttttgttc gacttggtat ggaggtcgga aatgtcgccc ttgttccat catggccttt   720

-continued

```
ggtgagaacg acctctatga ccaggttagc aacgacaagt cgtccaagct gtaccgattc    780
cagcagtttg tcaagaactt ccttggattc acccttcctt tgatgcatgc ccgaggcgtc    840
ttcaactacg atgtcggtct tgtcccctac aggcgacccg tcaacattgt ggttggttcc    900
cccattgact tgccttatct cccacacccc accgacgaag aagtgtccga ataccacgac    960
cgatacatcg ccgagctgca gcgaatctac aacgagcaca aggatgaata tttcatcgat   1020
tggaccgagg agggcaaagg agccccagag ttccgaatga ttgagtaa               1068
```

ACYLTRANSFERASES FOR ALTERATION OF POLYUNSATURATED FATTY ACIDS AND OIL CONTENT IN OLEAGINOUS YEASTS

CROSS REFERENCE TO RELATED APPLICATIONS

This application is a divisional of U.S. patent application Ser. No. 11/716,162, filed on 9 Mar. 2007 now U.S. Pat. No. 7,521,223, which is a divisional of U.S. patent application Ser. No. 11/592,806, filed on 3 Nov. 2006, now U.S. Pat. No. 7,465,565, which is a divisional of U.S. patent application Ser. No. 10/882,760, filed on 1 Jul. 2004, now U.S. Pat. No. 7,267,976, which claims benefit of U.S. Prov. App. No. 60/484,599, filed 2 Jul. 2003, and now expired.

FIELD OF THE INVENTION

This invention is in the field of biotechnology. More specifically, this invention pertains to the identification of nucleic acid fragments encoding phospholipid:diacylglycerol acyltransferase and diacylglycerol acyltransferase. These enzymes are useful for altering the quantity of oil in oleaginous microorganisms, such as oleaginous yeasts.

BACKGROUND OF THE INVENTION

The present invention is directed toward the development of an oleaginous yeast that accumulates oils enriched in long-chain $\omega$-3 and/or $\omega$-6 polyunsaturated fatty acids ("PUFAs"; e.g., 18:3, 18:4, 20:3, 20:4, 20:5, 22:6 fatty acids). Thus, in addition to developing techniques to introduce the appropriate fatty acid desaturases and elongases into these particular host organisms (where naturally produced PUFAs are usually limited to production of 18:2 fatty acids [and less commonly, 18:3 fatty acids]), it is also necessary to increase the transfer of PUFAs into storage lipid pools following their synthesis.

Most free fatty acids become esterified to coenzyme A (CoA), to yield acyl-CoAs. These molecules are then substrates for glycerolipid synthesis in the endoplasmic reticulum of the cell, where phosphatidic acid and diacylglycerol (DAG) are produced. Either of these metabolic intermediates may be directed to membrane phospholipids (e.g., phosphatidylglycerol, phosphatidylethanolamine, phosphatidylcholine) or DAG may be directed to form triacylglycerols (TAGs), the primary storage reserve of lipids in eukaryotic cells.

In the yeast *Saccharomyces cerevisiae*, three pathways have been described for the synthesis of TAGs. First, TAGs are mainly synthesized from DAG and acyl-CoAs by the activity of diacylglycerol acyltransferases. More recently, however, a phospholipid:diacylglycerol acyltransferase has also been identified that is responsible for conversion of phospholipid and DAG to lysophospholipid and TAG, respectively, thus producing TAG via an acyl-CoA-independent mechanism (Dahlqvist et al., *PNAS*. 97(12):6487-6492 (2000)). Finally, two acyl-CoA:sterol-acyltransferases are known that utilize acyl-CoAs and sterols to produce sterol esters (and TAGs in low quantities; see Sandager et al., *Biochem. Soc. Trans.* 28(6):700-702 (2000)).

A comprehensive mini-review on TAG biosynthesis in yeast, including details concerning the genes involved and the metabolic intermediates that lead to TAG synthesis, is that of D. Sorger and G. Daum (*Appl. Microbiol. Biotechnol.* 61:289-299 (2003)). However, the authors acknowledge that most work performed thus far has focused on *Saccharomyces cerevisiae* and numerous questions regarding TAG formation and regulation remain. In this organism it has been conclusively demonstrated that only four genes are involved in storage lipid synthesis: ARE1 and ARE2 (encoding acyl-CoA: sterol-acyltransferases), LRO1 (encoding a phospholipid: diacylglycerol acyltransferase, or PDAT enzyme) and DGA1 (encoding a diacylglycerol acyltransferase, or DGAT2 enzyme) (Sandager, L. et al., *J. Biol. Chem.* 277(8):6478-6482 (2002)). Homologs of these genes have been identified in various other organisms and disclosed in the public literature, but none of these genes have been isolated from oleaginous yeast. Furthermore, techniques for modifying the transfer of fatty acids to the TAG pool in oleaginous yeast have not been developed. Thus, there is a need for the identification and isolation of genes encoding acyltransferases that will be suitable for use in the production and accumulation of PUFAs in the storage lipid pools (i.e., TAG fraction) of oleaginous yeast.

Genera typically identified as oleaginous yeast include, but are not limited to: *Yarrowia, Candida, Rhodotorula, Rhodosporidium, Cryptococcus, Trichosporon* and *Lipomyces*. More specifically, illustrative oleaginous yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*). These organisms can accumulate oil up to 80% of their dry cell weight; and, the technology for growing oleaginous yeast with high oil content is well developed (for example, see EP 0 005 277B1; Ratledge, C., *Prog. Ind. Microbiol.* 16:119-206 (1982)). Most recently, the natural abilities of oleaginous yeast (mostly limited to 18:2 fatty acid production) have been enhanced by advances in genetic engineering, leading to the production of 20:4 (arachidonic acid), 20:5 (eicosapentaenoic acid) and 22:6 (docosahexaenoic acid) PUFAs in transformant *Yarrowia lipolytica*. These $\omega$-3 and $\omega$-6 fatty acids were produced by introducing and expressing heterologous genes encoding the $\omega$-3/$\omega$-6 biosynthetic pathway in the oleaginous host (see co-pending U.S. application Ser. No. 10/840,579).

The importance of PUFAs are undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA) or $\alpha$-linolenic acid (ALA); constituents of plasma membranes of cells, where they may be found in such forms as phospholipids or TAGs; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain $\omega$-3 PUFAs produces cardiovascular protective effects (Dyerberg, J. et al., *Amer. J. Clin Nutr.* 28:958-966 (1975); Dyerberg, J. et al., *Lancet* 2(8081):117-119 (Jul. 15, 1978); Shimokawa, H., *World Rev Nutr Diet*, 88:100-108 (2001); von Schacky, C., and Dyerberg, J., *World Rev Nutr Diet*, 88:90-99 (2001)). And, numerous other studies document wide-ranging health benefits conferred by administration of $\omega$-3 and/or $\omega$-6 fatty acids against a variety of symptoms and diseases (e.g., asthma, psoriasis, eczema, diabetes, cancer).

PUFAs are generally divided into two major classes (consisting of the $\omega$-6 and the $\omega$-3 fatty acids) that are derived by desaturation and elongation of the essential fatty acids, LA and ALA, respectively. Despite a variety of commercial sources of PUFAs from natural sources [e.g., seeds of evening primrose, borage and black currants; filamentous fungi (*Mortierella*), *Porphyridium* (red alga), fish oils and marine plankton (*Cyclotella, Nitzschia, Crypthecodinium*)], there are several disadvantages associated with these methods of production (e.g., highly heterogeneous oil compositions, accumulation of environmental pollutants, uncontrollable fluctuations in availability due to weather/disease, expense at the commercial scale). As a result of these limitations, extensive work has been conducted toward: 1.) the development of recombinant sources of PUFAs that are easy to produce commercially; and 2.) modification of fatty acid biosynthetic pathways, to enable production of desired PUFAs. Advances in the isolation, cloning and manipulation of fatty acid desaturase and elongase genes from various organisms have been made over the last several years. Knowledge of these gene sequences offers the prospect of producing a desired fatty acid and/or fatty acid composition in novel host organisms that do not naturally produce PUFAs.

As described in Picataggio et al. (co-pending U.S. patent application Ser. No. 10/840,579), oleaginous yeast have been identified as an appropriate microbial system in which to express PUFA desaturase and elongase genes to enable economical production of commercial quantities of one or more PUFAs in these particular hosts. To further advance the work described therein towards the development of an oleaginous yeast that accumulates oils enriched in ω-3 and/or ω-6 fatty acids, however, it is necessary to increase the transfer of these PUFAs into storage TAGs (oil), once they are synthesized by fatty acid desaturases and elongases. Thus, there is a need for the identification and isolation of genes encoding acyltransferases that will be suitable for use in the production and accumulation of PUFAs in TAGs. Techniques for modifying the transfer of fatty acids to the TAG pool in oleaginous yeasts must also be developed.

Applicants have solved the stated problem by isolating the genes encoding PDAT and DGAT2 from the oleaginous yeast, *Yarrowia lipolytica*. These genes will be useful to enable one to modify the transfer of free fatty acids (e.g., ω-3 and/or ω-6 fatty acids) to the TAG pool in oleaginous yeast.

SUMMARY OF THE INVENTION

The invention relates to the discover of two genes, one encoding a phospholipid:diacylglycerol acyltransferase enzyme and the other encoding a diacylglycerol acyltransferase enzyme, from *Yarrowia*. The genes and encoded enzymes are useful in manipulating the production of commercially useful oils in microorganisms, and particularly in oleaginous yeasts. Accordingly the invention provides an isolated nucleic acid molecule encoding an diacylglycerol acyltransferase enzyme, selected from the group consisting of:
 (a) an isolated nucleic acid molecule encoding the amino acid sequence selected from the group consisting of SEQ ID NOs:31, 78 and 79;
 (b) an isolated nucleic acid molecule that hybridizes with
  (a) under the following hybridization conditions: 0.1× SSC, 0.1% SDS, 65° C. and washed with 2×SSC, 0.1% SDS followed by 0.1×SSC, 0.1% SDS; or
 (c) an isolated nucleic acid molecule that is completely complementary to (a) or (b).

In another embodiment the invention provides an isolated nucleic acid molecule encoding an phospholipid:diacylglycerol acyltransferase enzyme, selected from the group consisting of:
 (a) an isolated nucleic acid molecule encoding the amino acid sequence as set forth in SEQ ID NO:46;
 (b) an isolated nucleic acid molecule that hybridizes with
  (a) under the following hybridization conditions: 0.1× SSC, 0.1% SDS, 65° C. and washed with 2×SSC, 0.1% SDS followed by 0.1×SSC, 0.1% SDS; or
 (c) an isolated nucleic acid molecule that is completely complementary to (a) or (b).

Similarly the invention provides polypeptides having diacylglycerol acyltransferase and phospholipid:diacylglycerol acyltransferase activity encoded by the isolated nucleic acid molecules of the invention as well as genetic chimera of these molecules and host cells comprising the same.

In one preferred embodiment the invention provides a method of increasing triacylglycerol content in a transformed host cell comprising:
 (a) providing a transformed host cell comprising:
  (i) at least one gene encoding an acyltransferase enzyme having the amino acid sequence selected from the group consisting of SEQ ID NOs:31, 78, 79 and 46 under the control of suitable regulatory sequences; and
  (ii) a source of fatty acids;
 (b) growing the cell of step (a) under conditions whereby the at least one gene encoding an acyltransferase enzyme is expressed, resulting in the transfer of the fatty acids to triacylglycerol; and
 (c) optionally recovering the triacylglycerol of step (b).

In an additional preferred embodiment the invention provides a method of increasing the ω-3 or ω-6 fatty acid content of triacylglycerols in a transformed host cell comprising:
 (a) providing a transformed host cell comprising:
  (i) at least one gene encoding at least one enzyme of the ω-3/ω-6 fatty acid biosynthetic pathway;
  (ii) at least one gene encoding an acyltransferase enzyme having the amino acid sequence selected from the group consisting of SEQ ID NOs:31, 78, 79 and 46 under the control of suitable regulatory sequences;
 (b) growing the cell of step (a) under conditions whereby the genes of (i) and (ii) are expressed, resulting in the production of at least one ω-3 or ω-6 fatty acid and its transfer to triacylglycerol; and
 (c) optionally recovering the triacylglycerol of step (b).

BRIEF DESCRIPTION OF THE DRAWINGS AND SEQUENCE DESCRIPTIONS

FIG. 4A shows a pairwise comparison between various yeast and fungal DGAT2 enzymes using a ClustalW analysis. In contrast, FIG. 4B shows a pairwise comparison between various yeast and fungal PDAT enzymes.

Figure 5A:
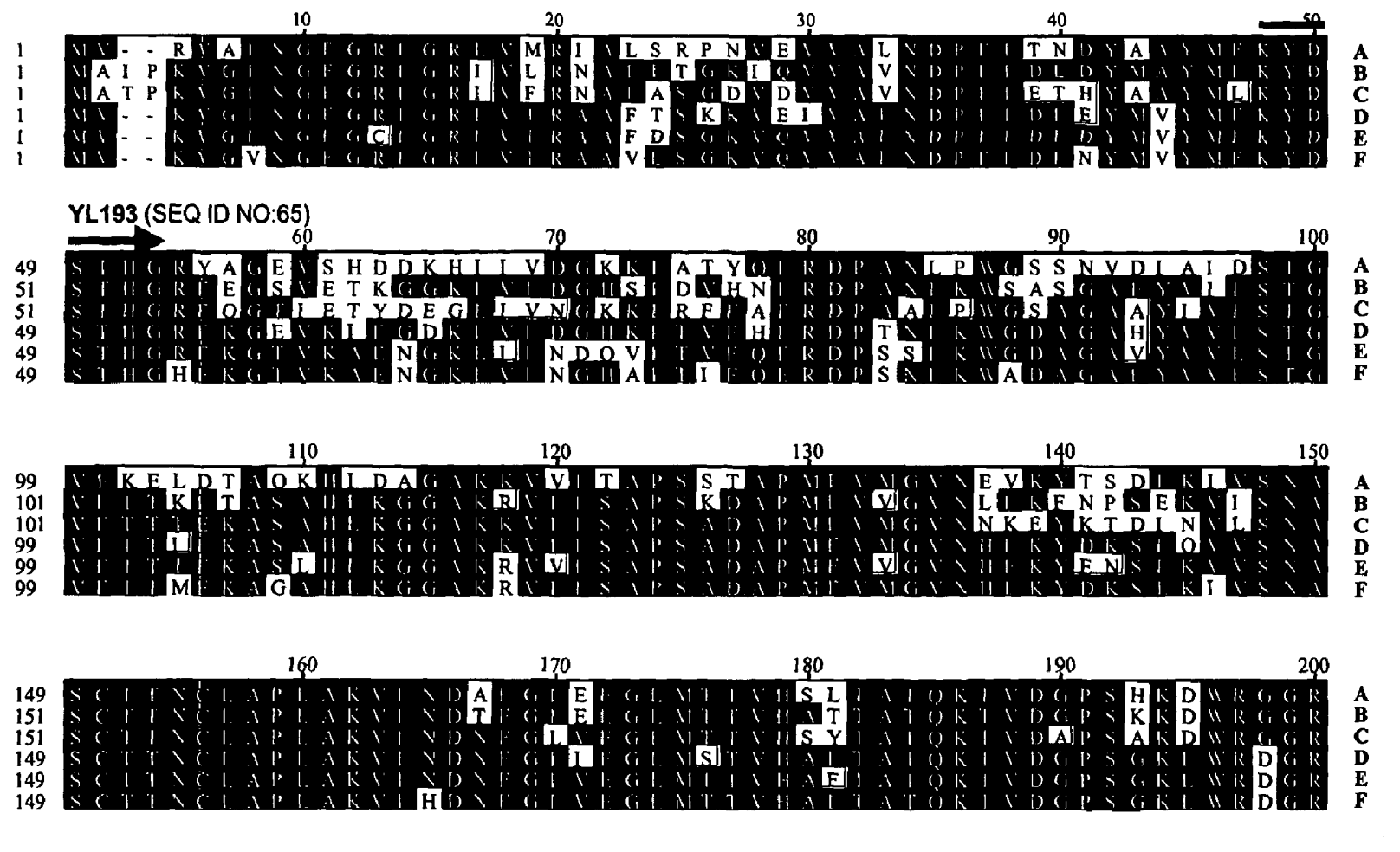
Figure 1:
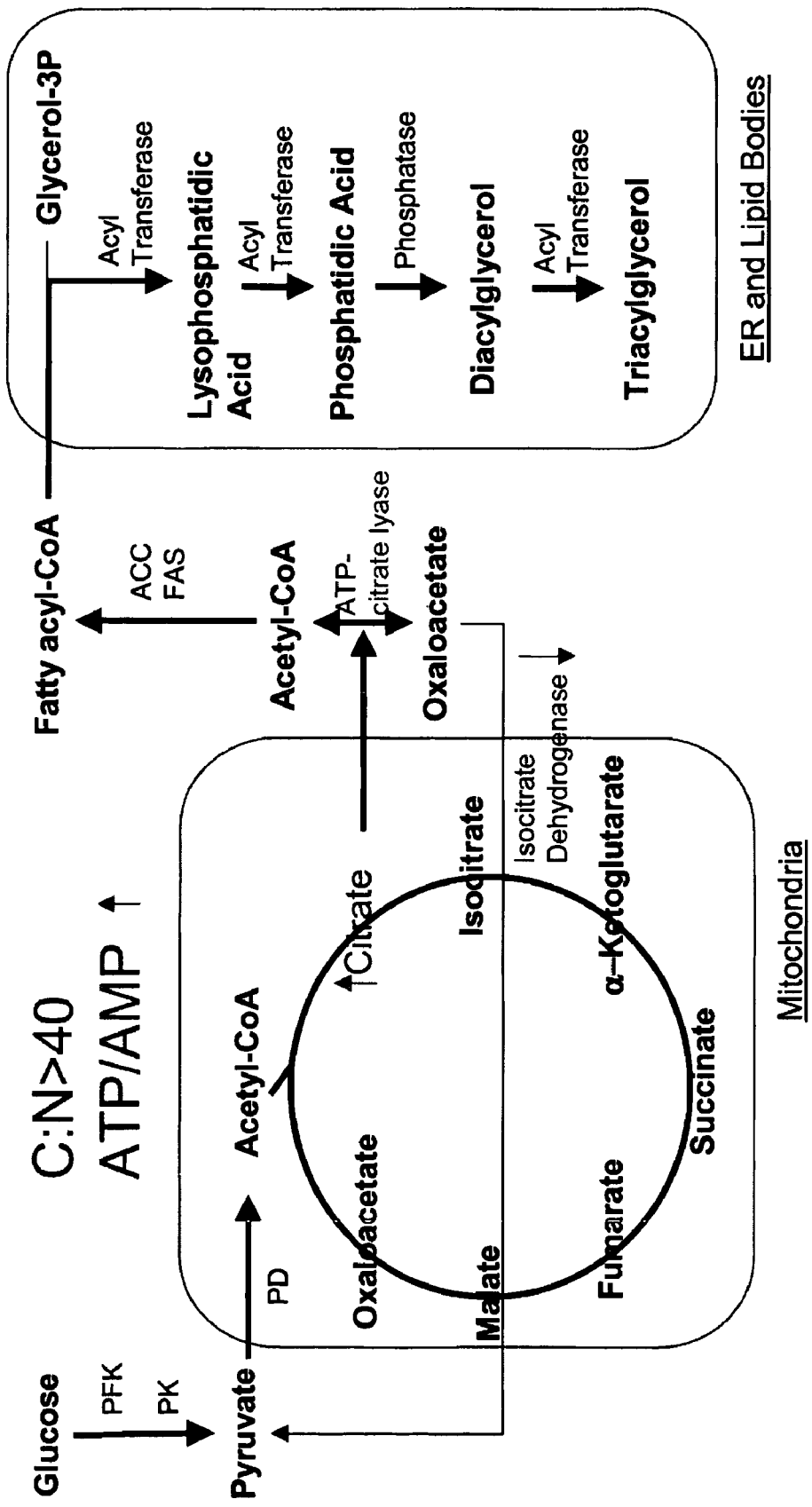
FIG. 1 shows a schematic illustration of the biochemical mechanism for lipid accumulation in oleaginous yeast.

FIGS. 5A and 5B show an alignment of known glyceraldehyde-3-phosphate dehydrogenase (GPD) proteins from *Saccharomyces cerevisiae* (GenBank Accession No. CAA24607), *Schizosaccharomyces pombe* (GenBank Accession No. NP_595236), *Aspergillus oryzae* (GenBank Accession No. AAK08065), *Paralichthys olivaceus* (GenBank Accession No. BAA88638), *Xenopus laevis* (GenBank Accession No. P51469) and *Gallus gallus* (GenBank Accession No. DECHG3), used to identify two conserved regions within the sequence alignment.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NOs:1 and 2 correspond to primers TEF5' and TEF3', respectively, used to isolate the TEF promoter.

SEQ ID NOs:3 and 4 correspond to primers XPR5' and XPR3', respectively, used to isolate the XPR2 transcriptional terminator.

SEQ ID NOs:5-16 correspond to primers YL5, YL6, YL9, YL10, YL7, YL8, YL3, YL4, YL1, YL2, YL61 and YL62, respectively, used for plasmid construction.

SEQ ID NO:17 corresponds to a 1 kB DNA fragment (amino acid sequence provided as SEQ ID NO:18) containing the *E. coli* hygromycin resistance gene.

SEQ ID NO:19 corresponds to a 1.7 kB DNA fragment containing the *Yarrowia* Ura3 gene (amino acid sequence provided as SEQ ID NO:20), which was amplified with primers KU5 and KU3 (SEQ ID NOs:21 and 22, respectively).

SEQ ID NOs:23 and 25 are the degenerate primers identified as P7 and P8, respectively, used for the isolation of a *Yarrowia lipolytica* DGAT2.

SEQ ID NOs:24 and 26 are the amino acid consensus sequences that correspond to the degenerate primers P7 and P8, respectively.

SEQ ID NOs:27-29 correspond to primers P80, P81 and LinkAmp Primer1, respectively, used for chromosome walking.

SEQ ID NO:30 shows a 2119 bp DNA sequence comprising an ORF that encodes the *Y. lipolytica* DGAT2. SEQ ID NO:31 is 514 amino acid residues in length and corresponds to nucleotides +291 to +1835 of SEQ ID NO:30; SEQ ID NO:78 is 459 amino acid residues in length and corresponds to nucleotides +456 to +1835 of SEQ ID NO:30; and, SEQ ID NO:79 is 355 amino acid residues in length and corresponds to nucleotides +768 to +1835 of SEQ ID NO:30, as set forth in SEQ ID NO:86.

SEQ ID NOs:32-35 correspond to primers P95, P96, P97 and P98, respectively, used for targeted disruption of the *Y. lipolytica* DGAT2 gene.

SEQ ID NOs:36-38 correspond to primers P115, P116 and P112, respectively, used to screen for targeted integration of the disrupted *Y. lipolytica* DGAT2 gene.

SEQ ID NOs:39 and 41 are the degenerate primers identified as P26 and P27, respectively, used for the isolation of the *Y. lipolytica* PDAT.

SEQ ID NOs:40 and 42 are the amino acid consensus sequences that correspond to degenerate primers P26 and P27, respectively.

SEQ ID NOs:43 and 44 correspond to primers P39 and P42, respectively, used to amplify a 1008 bp portion of the *Y. lipolytica* PDAT gene.

SEQ ID NO:45 shows a DNA sequence that encodes the *Y. lipolytica* PDAT (ORF=nucleotides +274 to +2217), while SEQ ID NO:46 shows the corresponding amino acid sequence of PDAT.

SEQ ID NOs:47 and 48 correspond to primers P41 and P40, respectively, used for targeted disruption of the *Y. lipolytica* PDAT gene.

SEQ ID NOs:49-52 correspond to primers P51, P52, P37 and P38, respectively, used to screen for targeted integration of the disrupted *Y. lipolytica* PDAT gene.

SEQ ID NO:53 corresponds to primer P79, used to amplify the full-length *Y. lipolytica* DGAT2 gene from rescued plasmids.

SEQ ID NOs:54 and 55 correspond to primers P84 and P85, respectively, used to amplify the full-length *Y. lipolytica* PDAT gene from rescued plasmids.

SEQ ID NO:56 corresponds to a 971 bp fragment designated as "GPDPro", and identified as the putative glyceraldehyde-3-phosphate dehydrogenase (GPD) promoter in *Y. lipolytica*.

SEQ ID NOs:57-62 correspond to the GPD amino acid sequences of *Saccharomyces cerevisiae* (GenBank Accession No. CAA24607), *Schizosaccharomyces pombe* (GenBank Accession No. NP_595236), *Aspergillus oryzae* (GenBank Accession No. AAK08065), *Paralichthys olivaceus* (GenBank Accession No. BAA88638), *Xenopus laevis* (GenBank Accession No. P51469) and *Gallus gallus* (GenBank Accession No. DECHG3), respectively.

SEQ ID NOs:63 and 64 correspond to conserved amino acid regions of the GPD protein.

SEQ ID NOs:65 and 66 correspond to the degenerate primers YL193 and YL194, respectively, used for isolating an internal portion of the *Y. lipolytica* GPD gene.

SEQ ID NO:67 encodes a 507 bp internal portion of the *Y. lipolytica* GPD gene, while SEQ ID NO:68 is the corresponding amino acid sequence.

SEQ ID NOs:69-71 correspond to primers YL206, YL207 and YL208, respectively, used for chromosome walking.

SEQ ID NO:72 corresponds to a 1848 bp fragment designated as "GPDP", comprising 1525 bp upstream of the GPD gene and an additional 323 bp representing a 5' portion of the GPD gene in *Y. lipolytica*.

SEQ ID NOs:73 and 74 correspond to primers P145 and P146, respectively, used to amplify the full-length *Y. lipolytica* DGAT2 gene.

SEQ ID NOs:75 and 76 correspond to primers YPDAT5 and YPDAT3, respectively, used to amplify the full-length *Y. lipolytica* PDAT gene.

SEQ ID NO:77 corresponds to primer LinkAmp primer 2, used for chromosome walking.

SEQ ID NOs:80 and 81 correspond to primers GPD-1 and GPD-2, respectively, used to amplify the *S. cerevisiae* glyceraldehyde-3-phosphate dehydrogenase (GPD) promoter.

SEQ ID NOs:82 and 83 correspond to primers ADHT-1 and ADHT-2, respectively, used to amplify the *S. cerevisiae* alcohol dehydrogenase (ADH1) terminator.

SEQ ID NOs:84 and 85 correspond to primers UP 161 and LP 162, respectively, used to create a *S. cerevisiae* LRO 1 targeting cassette.

DETAILED DESCRIPTION OF THE INVENTION

In accordance with the subject invention, Applicants have isolated and confirmed the identity of *Yarrowia lipolytica* genes encoding phospholipid:diacylglycerol acyltransferase (PDAT) and diacylglycerol acyltransferase (DGAT2) enzymes useful for transferring fatty acids into storage triacylglycerols (TAGs). This may be useful to alter the quantity of long chain polyunsaturated fatty acids (PUFAs) produced in oleaginous yeasts.

The subject invention finds many applications. PUFAs, or derivatives thereof, accumulated by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with arachidonic (ARA) can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

DEFINITIONS

In this disclosure, a number of terms and abbreviations are used. The following definitions are provided.

"Open reading frame" is abbreviated ORF.
"Polymerase chain reaction" is abbreviated PCR.
"American Type Culture Collection" is abbreviated ATCC.
"Polyunsaturated fatty acid(s)" is abbreviated PUFA(s).
"Phospholipid:diacylglycerol acyltransferase" is abbreviated PDAT.
"Diacylglycerol acyltransferase" is abbreviated DGAT.
"Diacylglycerol" is abbreviated DAG.
"Triacylglycerols" are abbreviated TAGs.
"Co-enzyme A" is abbreviated CoA.

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "omega-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "omega-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 1, in the column titled "Shorthand Notation". The remainder of the Table summarizes the common names of ω-3 and ω-6 fatty acids, the abbreviations that will be used throughout the specification and each compounds' chemical name.

TABLE 1

Nomenclature Of Polyunsaturated Fatty Acids

| Common Name | Abbreviation | Chemical Name | Shorthand Notation |
| --- | --- | --- | --- |
| Linoleic | LA | cis-9,12-octadecadienoic | 18:2 ω-6 |
| γ-Linoleic | GLA | cis-6,9,12-octadecatrienoic | 18:3 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

"Microbial oils" or "single cell oils" are those oils naturally produced by microorganisms (e.g., algae, oleaginous yeasts and filamentous fungi) during their lifespan. The term "oil" refers to a lipid substance that is liquid at 25° C. and usually polyunsaturated. In contrast, the term "fat" refers to a lipid substance that is solid at 25° C. and usually saturated.

"Lipid bodies" refer to lipid droplets that usually are bounded by specific proteins and a monolayer of phospholipid. These organelles are sites where most organisms transport/store neutral lipids. Lipid bodies are thought to arise from microdomains of the endoplasmic reticulum that contain TAG-biosynthesis enzymes; and, their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or TAG, respectively (or collectively, acylglycerols). A hydrolysis reaction must occur to release free fatty acids from acylglycerols.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

The term "DAG AT" refers to a diacylglycerol acyltransferase (also known as an acyl-CoA-diacylglycerol acyltransferase or a diacylglycerol O-acyltransferase) (EC 2.3.1.20). This enzyme is responsible for the conversion of acyl-CoA and 1,2-diacylglycerol to TAG and CoA (thereby involved in the terminal step of TAG biosynthesis). Two families of DAG AT enzymes exist: DGAT1 and DGAT2. The former family shares homology with the acyl-CoA:cholesterol acyltransferase (ACAT) gene family, while the latter family is unrelated (Lardizabal et al., *J. Biol. Chem.* 276(42):38862-28869 (2001)). A representative DGAT2 enzyme is encoded by the DGA1 gene of *Saccharomyces cerevisiae* (locus NP_014888 of Genbank Accession No. NC_001147; Oelkers et. al. *J. Biol. Chem.* 277:8877 (2002)); a gene encoding DGAT2 isolated from *Yarrowia lipolytica* is provided as SEQ ID NO:30.

The term "PDAT" refers to a phospholipid:diacylglycerol acyltransferase enzyme (EC 2.3.1.158). This enzyme is responsible for the transfer of an acyl group from the sn-2 position of a phospholipid to the sn-3 position of 1,2-diacylglycerol, thus resulting in lysophospholipid and TAG (thereby involved in the terminal step of TAG biosynthesis). This enzyme differs from DGAT (EC 2.3.1.20) by synthesizing TAG via an acyl-CoA-independent mechanism. A representative PDAT enzyme is encoded by the LRO1 gene in *Saccharomyces cerevisiae* (Dahlqvist et al., *Proc. Natl. Acad. Sci. USA* 97:6487 (2000)); a gene encoding PDAT isolated from *Yarrowia lipolytica* is provided as SEQ ID NO:45.

The term "PUFA biosynthetic pathway enzyme" refers to any of the following enzymes (and genes which encode said enzymes) associated with the biosynthesis of a PUFA including: a Δ4 desaturase, a Δ5 desaturase, a Δ6 desaturase, a Δ12 desaturase, a Δ15 desaturase, a Δ17 desaturase, a Δ9 desaturase, and/or a Δ8 desaturase and/or an elongase.

Figure 2:
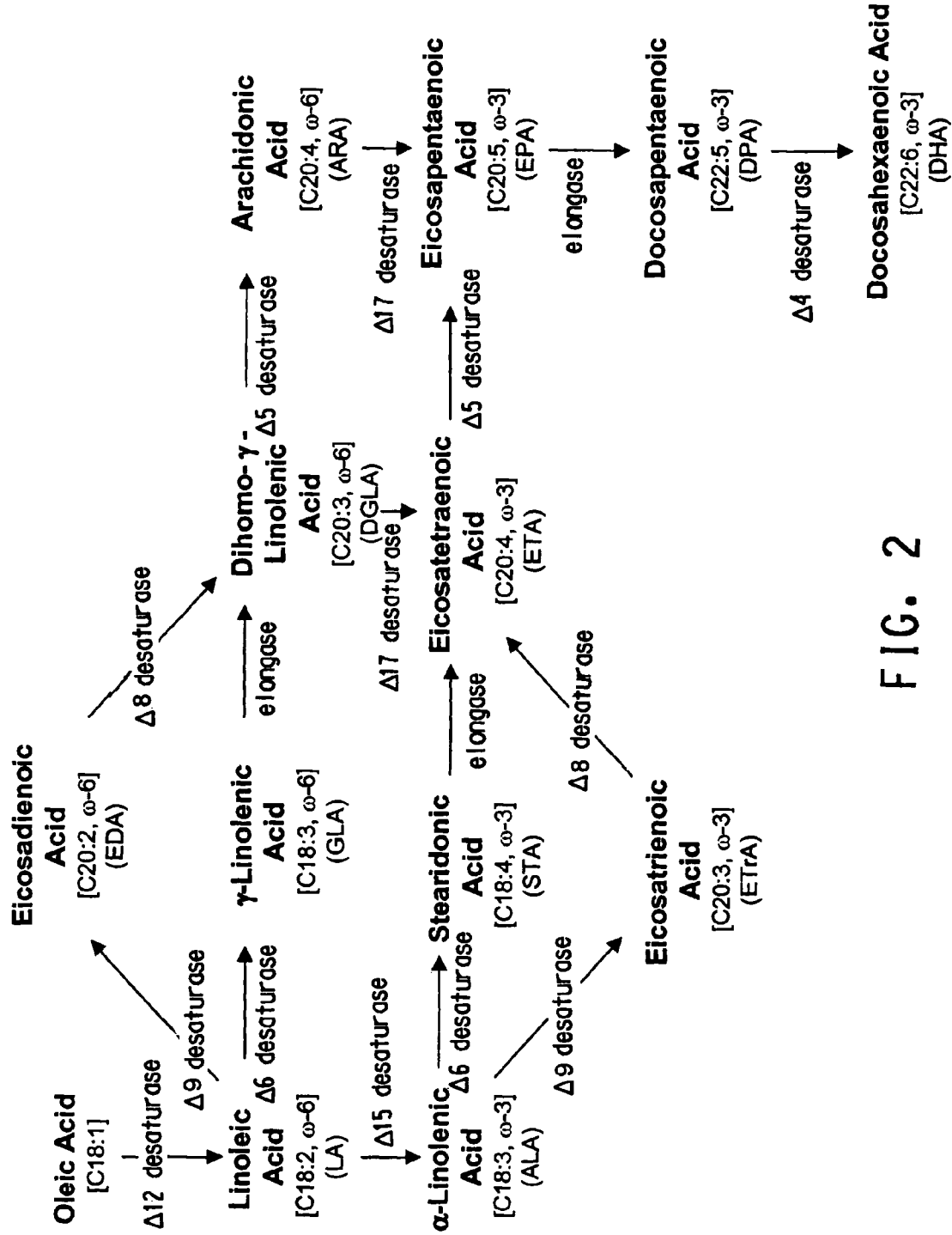
FIG. 2 illustrates the ω-3 and ω-6 fatty acid biosynthetic pathways.
Figure 3A:
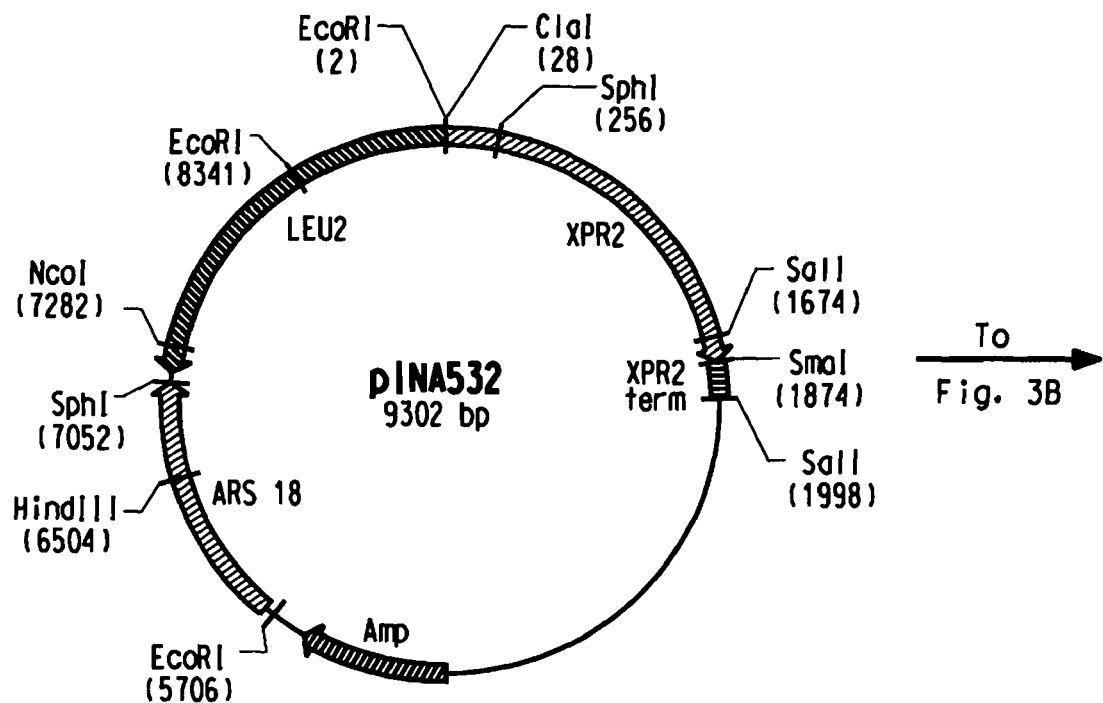
FIG. 3 illustrates the construction of the plasmid vectors pY5 and pY5-13 for gene expression in *Yarrowia lipolytica*.
Figure 3A:
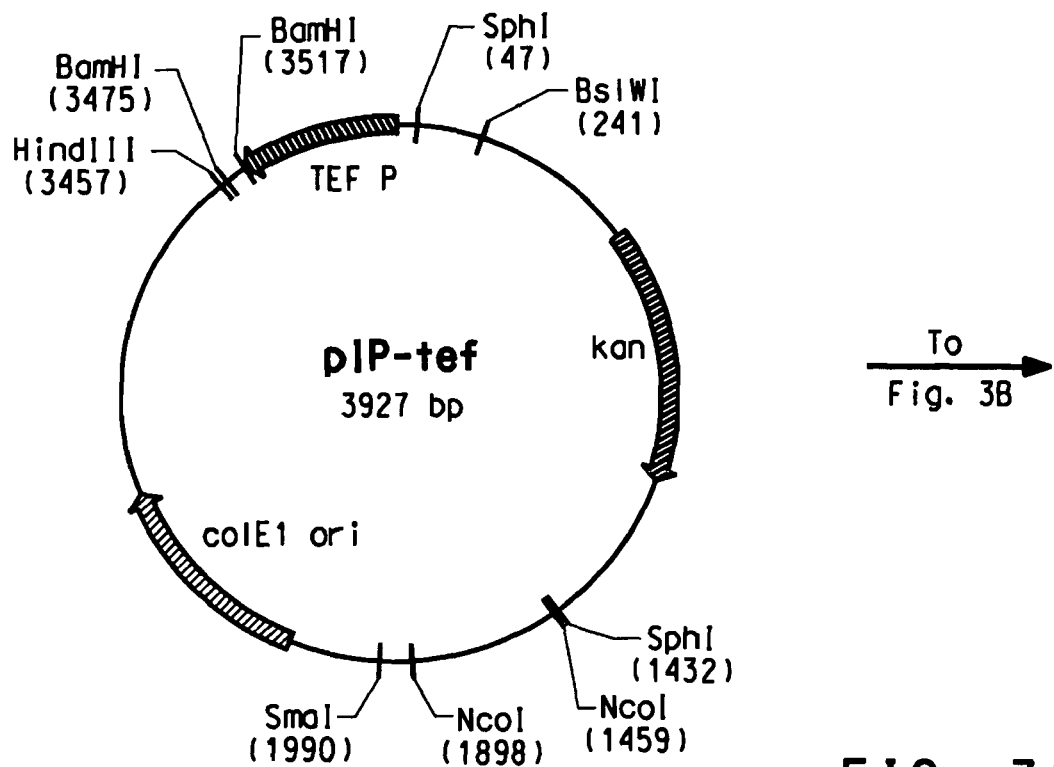
Figure 3B:
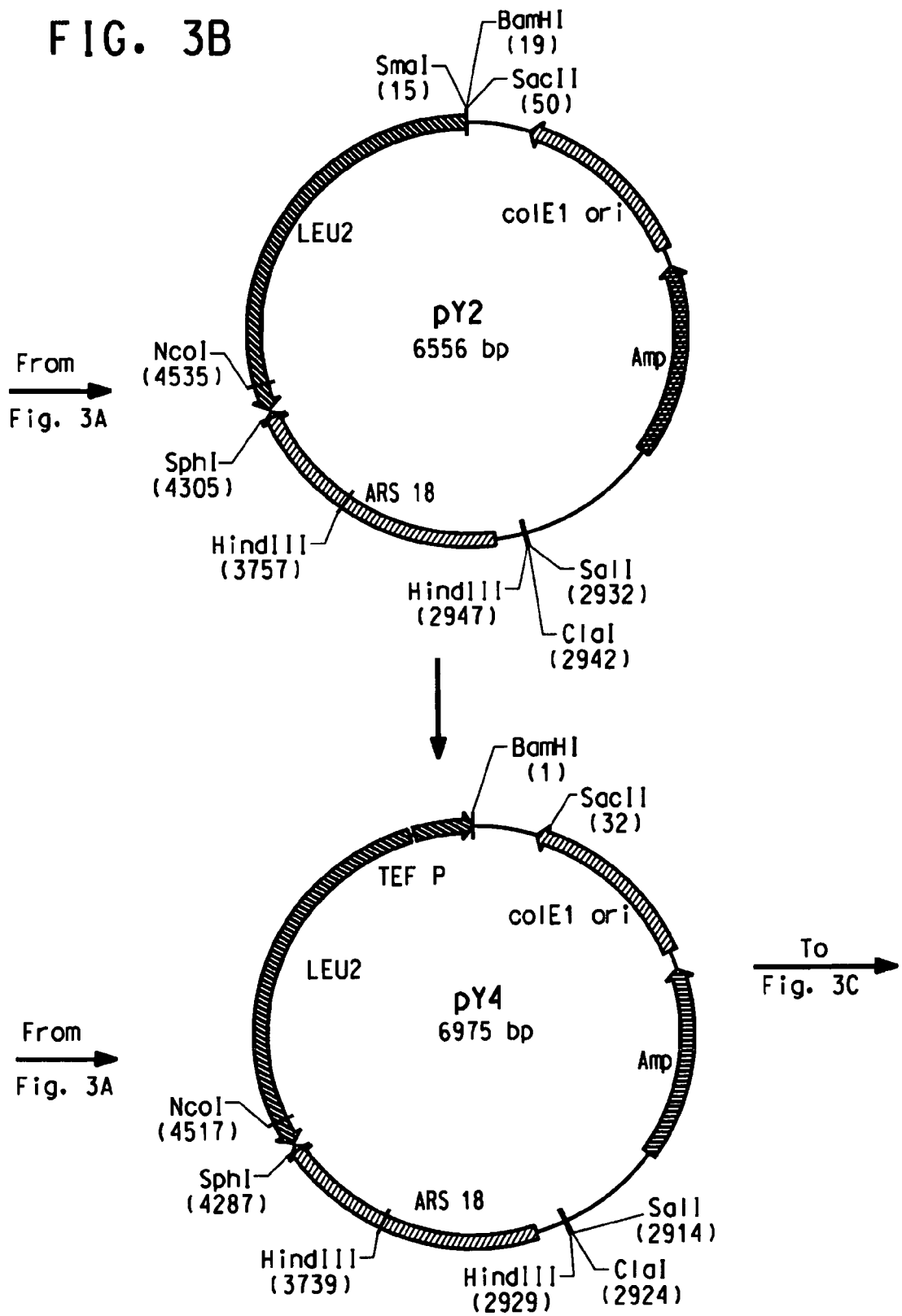
Figure 3C:
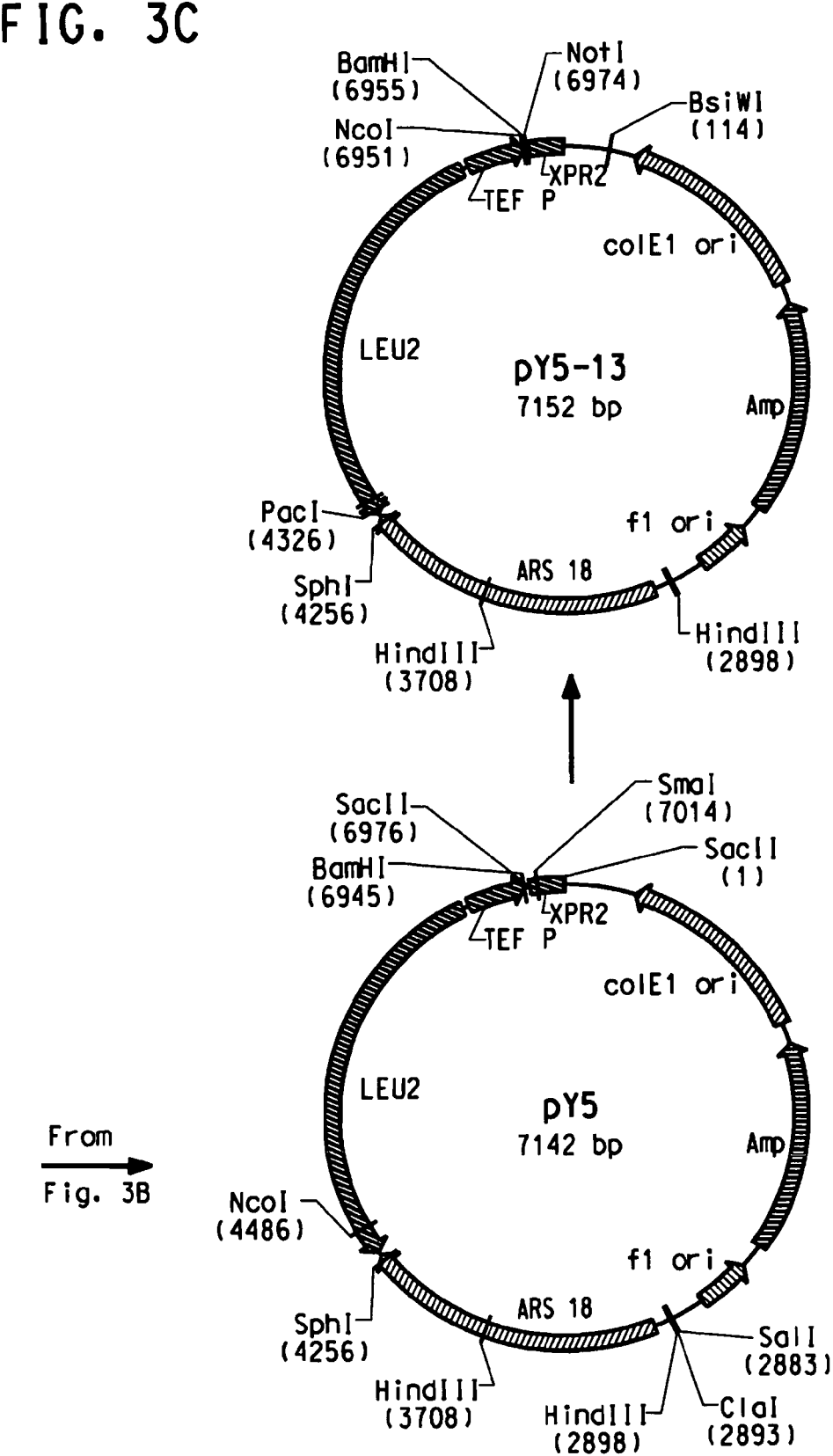

The term "ω-3/ω-6 fatty biosynthetic pathway" refers to genes encoding the enzymatic pathway as illustrated in FIG. 2, providing for the conversion of oleic acid through various intermediates to DHA.

The term "desaturase" refers to a polypeptide that can desaturate, i.e., introduce a double bond, in one or more fatty acids to produce a mono- or polyunsaturated fatty acid. Despite use of the omega-reference system throughout the specification in reference to specific fatty acids, it is more convenient to indicate the activity of a desaturase by counting from the carboxyl end of the substrate using the delta-system. Of particular interest herein are: Δ12 desaturases that desaturate a fatty acid between the $12^{th}$ and $13^{th}$ carbon atoms numbered from the carboxyl-terminal end of the molecule and that catalyze the conversion of oleic acid to LA; Δ15 desaturases that catalyze the conversion of LA to ALA; Δ17 desaturases that catalyze the conversion of ARA to EPA and/or DGLA to ETA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; Δ8 desaturases that catalyze the conversion of eicosadienoic acid (EDA; C20:2) to DGLA and/or eicosatrienoic acid (ETrA; C20:3) to ETA; and Δ9 desaturases that catalyze the conversion of palmitate to palmitoleic acid (16:1) and/or stearate to oleic acid (18:1).

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongases are the conversion of GLA to DGLA, STA to ETA, and EPA to DPA. Accordingly, elongases can have different specificities. For example, a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate. In like manner, a Δ9 elongase is able to catalyze the conversion of LA and ALA to eicosadienoic acid (EDA; C20:2) and eicosatrienoic acid (ETrA; C20:3), respectively.

The terms "conversion efficiency" and "percent substrate conversion" refer to the efficiency by which a particular enzyme (e.g., a desaturase or elongase) can convert substrate to product. The conversion efficiency is measured according to the following formula: ([product]/[substrate+product])*100, where 'product' includes the immediate product and all products in the pathway derived from it.

The term "oleaginous" refers to those organisms that have the ability to store their energy source in the form of TAGs (Weete, In: Fungal Lipid Biochemistry, $2^{nd}$ ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeasts that can accumulate at least 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon substrate" means a carbon source that a microorganism will metabolize to derive energy. Typical carbon substrates of the invention include, but are not limited to: monosaccharides, oligosaccharides, polysaccharides, alkanes, fatty acids, esters of fatty acids, monoglycerides, carbon dioxide, methanol, formaldehyde, formate and carbon-containing amines.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular yeast proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*. 5:151-153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized", as it refers to genes or coding regions of nucleic acid molecules, refers to modification of codons such that the altered codons reflect the typical codon usage of the host organism without altering the polypeptide for which the DNA codes.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "3'non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene(s) and having elements in addition to the foreign gene(s) that facilitate transformation of a particular host cell. "Expression cassette" refers to a specific vector containing a foreign gene(s) and having elements in addition to the foreign gene(s) that allow for enhanced expression of that gene in a foreign host.

The term "homologous recombination" refers to the exchange of DNA fragments between two DNA molecules (during cross over). The fragments that are exchanged are flanked by sites of identical nucleotide sequences between the two DNA molecules (i.e., "regions of homology"). The term "regions of homology" refer to stretches of nucleotide sequence on nucleic acid fragments that participate in homologous recombination that have homology to each other. Effective homologous recombination will take place where these regions of homology are at least about 10 bp in length where at least about 50 bp in length is preferred. Typically fragments that are intended for recombination contain at least two regions of homology where targeted gene disruption or replacement is desired.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Microbial Biosynthesis of Fatty Acids and Triacyglycerols

In general, lipid accumulation in oleaginous microorganisms is triggered in response to the overall carbon to nitrogen ratio present in the growth medium (FIG. 1). When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol, and subsequent cleavage of the citrate by ATP-citrate lyase to yield acetyl-CoA and oxaloacetate. Acetyl-CoA is the principle building block for de novo biosynthesis of fatty acids. Although any compound that can effectively be metabolized to acetyl-CoA can serve as a precursor of fatty acids, glucose is the primary source of carbon in this type of reaction (FIG. 1). Glucose is converted to pyruvate via glycolysis, and pyruvate is then transported into the mitochondria where it can be converted to acetyl-CoA by pyruvate dehydrogenase ("PD"). Since acetyl-CoA can not be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle, via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase ("ACC"). Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate. More specifically, FAS catalyzes a series of 7 reactions, which involve the following (Smith, S. FASEB J, 8(15):1248-59 (1994)):

1. Acetyl-CoA and malonyl-CoA are transferred to the acyl carrier peptide (ACP) of FAS. The acetyl group is then transferred to the malonyl group, forming β-ketobutyryl-ACP and releasing $CO_2$.
2. The β-ketobutyryl-ACP undergoes reduction (via β-ketoacyl reductase) and dehydration (via β-hydroxyacyl dehydratase) to form a trans-monounsaturated fatty acyl group.
3. The double bond is reduced by NADPH, yielding a saturated fatty-acyl group two carbons longer than the initial one. The butyryl-group's ability to condense with a new malonyl group and repeat the elongation process is then regenerated.
4. When the fatty acyl group becomes 16 carbons long, a thioesterase activity hydrolyses it, releasing free palmitate (16:0).

Whereas palmitate synthesis occurs in the cytosol, formation of longer chain saturated and unsaturated fatty acid derivates occur in both the mitochondria and endoplasmic reticulum (ER), wherein the ER is the dominant system. Specifically, palmitate (16:0) is the precursor of stearic (18:0), palmitoleic (16:1) and oleic (18:1) acids through the action of elongases and desaturases. For example, palmitate and stearate are converted to their unsaturated derivatives, palmitoleic (16:1) and oleic (18:1) acids, respectively, by the action of a Δ9 desaturase.

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and 4.) the addition of a third fatty acid by the action of a DAG acyltransferase (e.g., PDAT, DGAT2 or DGAT2) to form TAG (FIG. 1).

A wide spectrum of fatty acids can be incorporated into TAGs, including saturated and unsaturated fatty acids and short-chain and long-chain fatty acids. Some non-limiting examples of fatty acids that can be incorporated into TAGs by acyltransferases (e.g., DGAT2 or PDAT) include: capric (10:0), lauric (12:0), myristic (14:0), palmitic (16:0), palmitoleic (16:1), stearic (18:0), oleic (18:1), vaccenic (18:1), linoleic (18:2), eleostearic (18:3), γ-linolenic (18:3), α-linolenic (18:3), stearidonic (18:4), arachidic (20:0), eicosadienoic (20:2), dihomo-γ-linoleic (20:3), eicosatrienoic (20:3), arachidonic (20:4), eicosa-tetraenoic (20:4), eicosa-pentaenoic (20:5), behenic (22:0), docosa-pentaenoic (22:5), docosa-hexaenoic (22:6), lignoceric (24:0), nervonic (24:1), cerotic (26:0), and montanic (28:0) fatty acids. In preferred embodiments of the present invention, incorporation of PUFAs into TAG is most desirable.

Genes Encoding DGAT2

Historically, DGAT1 (responsible for the third acyl transferase reaction, wherein an acyl-CoA group is transferred from acyl-CoA to the sn-3 position of DAG to form TAG) was thought to be the only enzyme specifically involved in TAG synthesis. This enzyme was known to be homologous to acyl-CoA:cholesterol acyltransferases (ACATs); however, recent studies have identified a new family of DAG acyltransferase enzymes that are unrelated to the ACAT gene family. Thus, nomenclature now distinguishes between the DAG acyltransferase enzymes that are related to the ACAT gene family (DGAT1 family) versus those that are unrelated (DGAT2 family) (Lardizabal et al., *J. Biol. Chem.* 276(42): 38862-28869 (2001)). Members of the DGAT2 family appear to be present in all major phyla of eukaryotes (fungi, plants, animals, and basal eukaryotes).

Many genes encoding DGAT2 enzymes have been identified through genetic means and the DNA sequences of some of these genes are publicly available. For example, some non-limiting examples include the following GenBank Accession Numbers: NC_001147 (locus NP_014888; *Saccharomyces cerevisiae*); NM_012079 (human); NM_127503, AF051849 and AJ238008 (*Arabidopsis thaliana*); NM_026384, NM_010046 and AB057816 (mouse); AY093657 (pig); AB062762 (rat); AF221132 (*Caenorhabditis elegans*); AF391089 and AF391090 (*Mortierella ramanniana*); AF129003 (*Nicotiana tabacum*); and, AF251794 and AF164434 (*Brassica napus*). Additionally, the patent literature provides many additional DNA sequences of DGAT2 genes (and/or details concerning several of the genes above and their methods of isolation). See, for example: US 2003/124126 (Cases et al.); US 2003/115632, US2003/0028923 and US 2004/0107459 (Lardizabal et al.); and WO 2001/034814 (Banas et al.).

Despite disclosure of several complete and incomplete sequences encoding DGAT2 (supra), very few of these sequences have been shown to have DGAT2 activity. The exceptions include the work of: 1.) Bouvier-Nave, P. et al. (*Biochem. Soc. Trans.* 28(6):692-695 (2000)), wherein the DGAT2 of the nematode worm *Caenorhabditis elegans* was expressed in *Saccharomyces cerevisiae*, leading to an increase in TAG content and in microsomal oleyl-CoA:DAG acyltransferase activity; and, 2.) Lardizabal et al. (supra; see also US 2003/0028923 A1 and US 2004/0107459 A1), wherein two DGAT2s of the fungus *Mortierella ramanniana* were expressed in insect cells, leading to high levels of DGAT activity on membranes isolated from those cells. In addition to these demonstrations where oil biosynthesis was increased by over-expression of DGAT2, disruption of the genes encoding DGAT2 have also been shown to result in a decrease in the cellular TAG content (Oelkers et al. *J Biol. Chem.* 277(11): 8877-81 (2002); Sandager et al., *J Biol. Chem.* 277:6478-6482 (2002); Sorger and Daum. *J. Bacteriol.* 184:519-524 (2002)).

Genes Encoding PDAT

TAG synthesis can also occur in the absence of acyl-CoA, via the acyl-CoA-independent PDAT enzyme, as recently discovered by Dahlqvist et al. (*Proc. Nat. Acad. Sci.* (USA) 97:6487-6492 (2000)) and Oelkers et al. (*J. Biol. Chem.* 275: 15609-15612 (2000)). Specifically, PDAT removes an acyl group from the sn-2 position of a phosphotidylcholine substrate for transfer to the sn-3 position of DAG to produce TAG; and, although the function of PDAT is not as well characterized as DGAT2, PDAT has been postulated to play a major role in removing "unusual" fatty acids from phospholipids in some oilseed plants (Banas, A. et al., *Biochem. Soc. Trans.* 28(6):703-705 (2000)).

PDAT is structurally related to the lecithin:cholesterol acyltransferase (LCAT) family of proteins. Several genes encoding PDAT enzymes have been identified through genetic means and the DNA sequences of some of these genes are publicly available. For example, some non-limiting examples include the following GenBank Accession Numbers: P40345 (*Saccharomyces cerevisiae*); O94680 and NP_596330 (*Schizosaccharomyces pombe*); and, NP_190069 and AB006704 [gi:2351069] *Arabidopsis thaliana*). Additionally, the patent literature provides many additional DNA sequences of PDAT genes (and/or details concerning several of the genes above and their methods of isolation); see, for example, WO 2000/060095 (Dahlqvist et al.).

In a manner similar to DGAT2, over-expression of PDAT has been accomplished in *Saccharomyces cerevisiae* to increase oil biosynthesis. For example, over-expressing the *S. cerevisiae* LRO1 gene encoding PDAT resulted in an increased TAG content, confirming the involvement of this enzyme in TAG formation (Dahlqvist et al. *Proc. Nat. Acad. Sci.* (USA) 97:6487-6492 (2000); Oelkers et al., *J. Biol. Chem.* 275:15609-15612 (2000)). In contrast, deletion of the LRO1 gene was found to cause significant reduction of TAG synthesis (Oelkers et al., supra).

Biosynthesis of Omega-3 and Omega-6 Polyunsaturated Fatty Acids

The metabolic process that converts LA to GLA, DGLA and ARA (the ω-6 pathway) and ALA to STA, ETA, EPA, DPA and DHA (the ω-3 pathway) involves elongation of the carbon chain through the addition of two-carbon units and desaturation of the molecule through the addition of double bonds (FIG. 2). This requires a series of desaturation and elongation enzymes. Specifically, oleic acid is converted to LA (18:2), the first of the ω-6 fatty acids, by the action of a Δ12 desaturase. Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase. In like manner, linoleic acid (LA) is converted to ALA, the first of the ω-3 fatty acids, by the action of a Δ15 desaturase. Subsequent (ω-3 fatty acids are produced in a series of steps similar to that for the (ω-6 fatty acids. Specifically, 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

In alternate embodiments, a Δ9 elongase is able to catalyze the conversion of LA and ALA to eicosadienoic acid (EDA; C20:2) and eicosatrienoic acid (ETrA; C20:3), respectively. A Δ8 desaturase then converts these products to DGLA and ETA, respectively.

Many microorganisms, including algae, bacteria, molds, fungi and yeasts, can synthesize PUFAs and omega fatty acids in the ordinary course of cellular metabolism. Particularly well-studied are fungi including *Schizochytrium aggregatm*, species of the genus *Thraustochytrium* and *Mortierella alpina*. Additionally, many dinoflagellates (Dinophyceaae) naturally produce high concentrations of PUFAs. As such, a variety of desaturase and elongase genes involved in PUFA production have been identified through genetic means and the DNA sequences of some of these genes are publicly available (non-limiting examples are shown below in Table 2):

TABLE 2

Some Publicly Available Genes Involved In PUFA Production

| Genbank Accession No. | Description |
|---|---|
| AY131238 | *Argania spinosa* Δ6 desaturase |
| Y055118 | *Echium pitardii* var. *pitardii* Δ6 desaturase |
| AY055117 | *Echium gentianoides* Δ6 desaturase |
| AF296076 | *Mucor rouxii* Δ6 desaturase |
| AF007561 | *Borago officinalis* Δ6 desaturase |
| L11421 | *Synechocystis* sp. Δ6 desaturase |
| NM_031344 | *Rattus norvegicus* Δ6 fatty acid desaturase |
| AF465283, AF465281, AF110510 | *Mortierella alpina* Δ6 fatty acid desaturase |
| AF465282 | *Mortierella isabellina* Δ6 fatty acid desaturase |
| AF419296 | *Pythium irregulare* Δ6 fatty acid desaturase |
| AB052086 | *Mucor circinelloides* D6d mRNA for Δ6 fatty acid desaturase |
| AJ250735 | *Ceratodon purpureus* mRNA for Δ6 fatty acid desaturase |
| AF126799 | *Homo sapiens* Δ6 fatty acid desaturase |
| AF126798 | *Mus musculus* Δ6 fatty acid desaturase |
| AF199596, AF226273 | *Homo sapiens* Δ5 desaturase |
| AF320509 | *Rattus norvegicus* liver Δ5 desaturase |
| AB072976 | *Mus musculus* D5D mRNA for Δ5 desaturase |
| AF489588 | *Thraustochytrium* sp. ATCC21685 Δ5 fatty acid desaturase |
| AJ510244 | *Phytophthora megasperma* mRNA for Δ5 fatty acid desaturase |
| AF419297 | *Pythium irregulare* Δ5 fatty acid desaturase |
| AF07879 | *Caenorhabditis elegans* Δ5 fatty acid desaturase |
| AF067654 | *Mortierella alpina* Δ5 fatty acid desaturase |
| AB022097 | *Dictyostelium discoideum* mRNA for Δ5 fatty acid desaturase |
| AF489589.1 | *Thraustochytrium* sp. ATCC21685 Δ4 fatty acid desaturase |
| AAG36933 | *Emericella nidulans* oleate Δ12 desaturase |
| AF110509 | *Mortierella alpina* Δ12 fatty acid desaturase mRNA |
| AB020033 | *Mortierella alpina* mRNA for Δ12 fatty acid desaturase |
| AAL13300 | *Mortierella alpina* Δ12 fatty acid desaturase |
| AF417244 | *Mortierella alpina* ATCC 16266 Δ12 fatty acid desaturase gene |
| AF161219 | *Mucor rouxii* Δ12 desaturase mRNA |
| AY332747 | *Pavlova lutheri* Δ4 fatty acid desaturase (des1) mRNA |
| AAG36933 | *Emericella nidulans* oleate Δ12 desaturase |
| AF110509, AB020033 | *Mortierella alpina* Δ12 fatty acid desaturase mRNA |
| AAL13300 | *Mortierella alpina* Δ12 fatty acid desaturase |
| AF417244 | *Mortierella alpina* ATCC 16266 Δ12 fatty acid desaturase |

TABLE 2-continued

Some Publicly Available Genes Involved In PUFA Production

| Genbank Accession No. | Description |
|---|---|
| AF161219 | *Mucor rouxii* Δ12 desaturase mRNA |
| X86736 | *Spiruline platensis* Δ12 desaturase |
| AF240777 | *Caenorhabditis elegans* Δ12 desaturase |
| AB007640 | *Chlamydomonas reinhardtii* Δ12 desaturase |
| AB075526 | *Chlorella vulgaris* Δ12 desaturase |
| AP002063 | *Arabidopsis thaliana* microsomal Δ12 desaturase |
| NP_441622, BAA18302, BAA02924 | *Synechocystis* sp. PCC 6803 Δ15 desaturase |
| AAL36934 | *Perilla frutescens* Δ15 desaturase |
| AF338466 | *Acheta domesticus* Δ9 desaturase 3 mRNA |
| AF438199 | *Picea glauca* desaturase Δ9 (Des9) mRNA |
| E11368 | *Anabaena* Δ9 desaturase |
| E11367 | *Synechocystis* Δ9 desaturase |
| D83185 | *Pichia angusta* DNA for Δ9 fatty acid desaturase |
| U90417 | *Synechococcus vulcanus* Δ9 acyl-lipid fatty acid desaturase (desC) gene |
| AF085500 | *Mortierella alpina* Δ9 desaturase mRNA |
| AY504633 | *Emericella nidulans* Δ9 stearic acid desaturase (sdeB) gene |
| NM_069854 | *Caenorhabditis elegans* essential fatty acid desaturase, stearoyl-CoA desaturase (39.1 kD) (fat-6) complete mRNA |
| AF230693 | *Brassica oleracea* cultivar Rapid Cycling stearoyl-ACP desaturase (Δ9-BO-1) gene, exon sequence |
| AX464731 | *Mortierella alpina* elongase gene (also WO 02/08401) |
| NM_119617 | *Arabidopsis thaliana* fatty acid elongase 1 (FAE1) (At4g34520) mRNA |
| NM_134255 | *Mus musculus* ELOVL family member 5, elongation of long chain fatty acids (yeast) (Elovl5), mRNA |
| NM_134383 | *Rattus norvegicus* fatty acid elongase 2 (rELO2), mRNA |
| NM_134382 | *Rattus norvegicus* fatty acid elongase 1 (rELO1), mRNA |
| NM_068396, NM_068392, NM_070713, NM_068746, NM_064685 | *Caenorhabditis elegans* fatty acid ELOngation (elo-6), (elo-5), (elo-2), (elo-3), and (elo-9) mRNA |

Additionally, the patent literature provides many additional DNA sequences of genes (and/or details concerning several of the genes above and their methods of isolation) involved in PUFA production. See, for example: U.S. Pat. No. 5,968,809 (Δ6 desaturases); U.S. Pat. No. 5,972,664 and U.S. Pat. No. 6,075,183 (Δ5 desaturases); WO 91/13972 and U.S. Pat. No. 5,057,419 (Δ9 desaturases); WO 93/11245 (Δ15 desaturases); WO 94/11516, U.S. Pat. No. 5,443,974 and WO 03/099216 (Δ12 desaturases); WO 00/12720 and U.S. 2002/0139974A1 (elongases); U.S. 2003/0196217 A1 (Δ17 desaturase); WO 00/34439 (Δ8 desaturases); and, WO 02/090493 (Δ4 desaturases). Each of these patents and applications are herein incorporated by reference in their entirety.

Depending upon the host cell, the availability of substrate, and the desired end product(s), several desaturases and elongases are of interest for use in production of PUFAs. Considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) co-factors required by the polypeptide. The expressed polypeptide preferably has parameters compatible with the biochemical environment of its location in the host cell. For example, the polypeptide may have to compete for substrate with other enzymes in the host cell. Analyses of the KM and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired fatty acid substrate.

Sequence Identification of *Yarrowia lipolytica* DGAT2 and PDAT Acyltransferases Despite the availability of several genes encoding DGAT2 and PDAT (supra) which could be used for heterologous expression in oleaginous yeast (e.g., *Yarrowia lipolytica*), expression of a native enzyme is preferred over a heterologous (or "foreign") enzyme whenever possible. This preference occurs because: 1.) the native enzyme is optimized for interaction with other enzymes and proteins in the cell; and 2.) heterologous genes are unlikely to share the same codon preference in the host organism. Knowledge of the sequences of a host organism's native PDAT and DGAT2 genes also facilitates disruption of the homologous chromosomal genes by targeted disruption. And, as the present invention has shown, disruption of one or more of an organism's acyltransferases (e.g., PDAT, DGAT2), when at least one acyltransferase remains functional, can result in altered oil content.

Comparison of the PDAT nucleotide base (SEQ ID NO:45) and deduced amino acid (SEQ ID NO:46) sequences to some public databases reveals that the most similar known sequences are about 47.1% identical to the amino acid sequence of PDAT reported herein over a length of 648 amino acids using the Clustal W method of alignment (Higgins and Sharp, *CABIOS.* 5:151-153 (1989)). More preferred amino acid fragments are at least about 70%-80% identical to the sequences herein, where those sequences that are 85%-90% identical are particularly suitable and those sequences that are about 95% identical are most preferred. Similarly, preferred PDAT encoding nucleic acid sequences corresponding to the instant ORF are those encoding active proteins and which are at least about 70%-80% identical to the nucleic acid sequences encoding PDAT reported herein, where those sequences that are 85%-90% identical are particularly suitable and those sequences that are about 95% identical are most preferred.

Comparison of the DGAT2 nucleotide base (SEQ ID NO:30) and deduced amino acid (SEQ ID NO:79) sequences to some public databases reveals that the most similar known sequences are about 38.4% identical to the amino acid sequence of DGAT2 reported herein over a length of 355 amino acids using the Clustal W method of alignment (Higgins and Sharp, supra). More preferred amino acid fragments are at least about 70%-80% identical to the sequences herein, where those sequences that are 85%-90% identical are particularly suitable and those sequences that are about 95% identical are most preferred. Similarly, preferred DGAT2 encoding nucleic acid sequences corresponding to the instant ORF are those encoding active proteins and which are at least about 70%-80% identical to the nucleic acid sequences encoding DGAT2 reported herein, where those sequences that are 85%-90% identical are particularly suitable and those sequences that are about 95% identical are most preferred.

Isolation of Homologs

Each of the acyltransferase nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the acyltransferases described herein could be isolated directly by using all or a portion of the instant nucleic acid fragments as DNA hybridization probes to screen libraries from any desired yeast or fungus using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the instant acyltransferase sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, Nucl. Acids Res. 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can then be used to screen DNA expression libraries to isolate full-length DNA clones of interest (Lerner, R. A. Adv. Immunol. 36:1 (1984); Maniatis, supra).

Gene Optimization for Improved Heterologous Expression

It may be desirable to modify the expression of particular acyltransferases and/or PUFA biosynthetic pathway enzymes to achieve optimal conversion efficiency of each, according to the specific TAG composition of interest. As such, a variety of techniques can be utilized to improve/optimize the expression of a polypeptide of interest in an alternative host. Two such techniques include codon-optimization and mutagenesis of the gene.

Codon Optimization

For the purposes of the present invention, it may be desirable to modify a portion of the codons encoding polypeptides having acyltransferase activity, for example, to enhance the expression of genes encoding those polypeptides in an alternate host (i.e., an oleaginous yeast other than Yarrowia lipolytica). In general, host-preferred codons can be determined within a particular host species of interest by examining codon usage in proteins (preferably those expressed in the largest amount) and determining which codons are used with highest frequency. Thus, the coding sequence for a polypeptide having acyltransferase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

Mutagenesis

Methods for synthesizing sequences and bringing sequences together are well established in the literature. For example, in vitro mutagenesis and selection, site-directed mutagenesis, error prone PCR (Melnikov et al., Nucleic Acids Research, 27(4):1056-1062 (Feb. 15, 1999)), "gene shuffling" or other means can be employed to obtain mutations of naturally occurring acyltransferase genes. This would permit production of a polypeptide having acyltransferase activity in vivo with more desirable physical and kinetic parameters for function in the host cell (e.g., a longer half-life or a higher rate of synthesis of TAGs from fatty acids).

If desired, the regions of an acyltransferase polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of an acyltransferase polypeptide important for activity. A mutated construct is expressed, and the ability of the resulting altered protein to function as an acyltransferase is assayed. Such structure-function analysis can determine which regions may be deleted, which regions tolerate insertions, and which point mutations allow the mutant protein to function in substantially the same way as the native acyltransferase.

All such mutant proteins and nucleotide sequences encoding them that are derived from the acyltransferase genes described herein are within the scope of the present invention.

Microbial Production of Fatty Acids and Triacyglycerols

Microbial production of fatty acids and TAGs has several advantages over purification from natural sources such as fish or plants. For example:

1.) Many microbes are known with greatly simplified oil compositions compared with those of higher organisms, making purification of desired components easier;
2.) Microbial production is not subject to fluctuations caused by external variables, such as weather and food supply;
3.) Microbially produced oil is substantially free of contamination by environmental pollutants; and,
4.) Microbial oil production can be manipulated by controlling culture conditions, notably by providing particular substrates for microbially expressed enzymes, or by addition of compounds or genetic engineering approaches to suppress undesired biochemical pathways.

With respect to the production of ω-3 and/or ω-6 fatty acids in particular, and TAGs containing those PUFAs, additional advantages are incurred since microbes can provide fatty acids in particular forms that may have specific uses; and, recombinant microbes provide the ability to alter the naturally occurring microbial fatty acid profile by providing new biosynthetic pathways in the host or by suppressing undesired pathways, thereby increasing levels of desired PUFAs, or conjugated forms thereof, and decreasing levels of undesired PUFAs.

Thus, knowledge of the sequences of the present acyltransferase genes will be useful for manipulating fatty acid biosynthesis and accumulation in oleaginous yeasts, and particularly, in *Yarrowia lipolytica*. This may require metabolic engineering directly within the fatty acid or TAG biosynthetic pathways or additional manipulation of pathways that contribute carbon to the fatty acid biosynthetic pathway. Methods useful for manipulating biochemical pathways are well known to those skilled in the art.

Metabolic Engineering to Up-Regulate Genes and Biosynthetic Pathways Affecting Fatty Acid Synthesis and Oil Accumulation in Oleaginous Yeast It is expected that introduction of chimeric genes encoding the acyltransferases described herein, under the control of the appropriate promoters, will result in increased transfer of fatty acids to storage TAGs. As such, the present invention encompasses a method for increasing the TAG content in an oleaginous yeast comprising expressing at least one acyltransferase enzyme of the present invention in a transformed oleaginous yeast host cell producing a fatty acid, such that the fatty acid is transferred to the TAG pool.

Additional copies of acyltransferase genes may be introduced into the host to increase the transfer of fatty acids to the TAG fraction. Expression of the genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of heterologous genes is to increase the translational efficiency of the encoded mRNAs by replacement of codons in the native gene with those for optimal gene expression in the selected host microorganism.

In one specific embodiment, the present invention encompasses a method of increasing the ω-3 and/or ω-6 fatty acid content of TAGs in an oleaginous yeast, since it is possible to introduce an expression cassette encoding each of the enzymes necessary for ω-3 and/or ω-6 fatty acid biosynthesis into the organism (since naturally produced PUFAs in these organisms are limited to 18:2 (i.e., LA), and less commonly 18:3 (i.e., ALA) fatty acids). Thus, the method comprises:

a) providing a transformed oleaginous yeast host cell (possessing at least one gene encoding at least one enzyme of the ω-3/ω-6 fatty acid biosynthetic pathway and at least one acyltransferase enzyme of the present invention);
b) growing the yeast cells of step (a) in the presence of a fermentable carbon substrate, whereby the gene(s) of the ω-3/ω-6 fatty acid biosynthetic pathway and the acyltransferase(s) are expressed, whereby a ω-3 and/or ω-6 fatty acid is produced, and whereby the ω-3 and/or ω-6 fatty acid is transferred to TAGs.

A variety of PUFA products can be produced (prior to their transfer to TAGs), depending on the fatty acid substrate and the particular genes of the ω-3/ω-6 fatty acid biosynthetic pathway that are transformed into the host cell. As such, production of the desired fatty acid product can occur directly (wherein the fatty acid substrate is converted directly into the desired fatty acid product without any intermediate steps or pathway intermediates) or indirectly (wherein multiple genes encoding the PUFA biosynthetic pathway may be used in combination, such that a series of reactions occur to produce a desired PUFA). Specifically, for example, it may be desirable to transform an oleaginous yeast with an expression cassette comprising a Δ12 desaturase, Δ6 desaturase, a high-affinity elongase, a Δ5 desaturase and a Δ17 desaturase for the overproduction of EPA. As is well known to one skilled in the art, various other combinations of the following enzymatic activities may be useful to express in a host in conjunction with the acyltransferases described herein: a Δ15 desaturase, a Δ4 desaturase, a Δ5 desaturase, a Δ6 desaturase, a Δ17 desaturase, a Δ9 desaturase, a Δ8 desaturase and/or an elongase (see FIG. 2). The particular genes included within a particular expression cassette will depend on the host cell (and its PUFA profile and/or desaturase profile), the availability of substrate and the desired end product(s).

Thus, within the context of the present invention, it may be useful to modulate the expression of the TAG biosynthetic pathway by any one of the methods described above. For example, the present invention provides genes encoding key enzymes in the fatty acid biosynthetic pathway leading to the storage of TAGs. These genes encode the PDAT and DGAT2 enzymes. It will be particularly useful to modify the expression levels of these genes in oleaginous yeasts to maximize production and accumulation of TAGs using various means for metabolic engineering of the host organism. In preferred embodiments, modification of the expression levels for these genes in combination with expression of ω-3/ω-6 biosynthetic genes can be utilized to maximize production and accumulation of preferred PUFAs in the TAG pool.

Metabolic Engineering to Down-Regulate Undesirable Genes and Biosynthetic Pathways Affecting Fatty Acid Synthesis and Oil Accumulation in Oleaginous Yeast In some embodiments, it may be useful to disrupt or inactivate a host organism's native acyltransferase(s), based on the complete sequences described herein, the complement of those complete sequences, substantial portions of those sequences, codon-optimized desaturases derived therefrom, and those sequences that are substantially homologous thereto. For example, the targeted disruption of the DGAT2 acyltransferase, PDAT acyltransferase, and DGAT2 and PDAT acyltransferases (as a double knockout) described herein in *Yarrowia lipolytica* produced mutant strains that each had different reduced levels of oil production (Example 5).

For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al., *J. Bacteriol.* 171:4617-4622 (1989); Balbas et al., *Gene* 136:211-213 (1993); Gueldener et al., *Nucleic Acids Res.* 24:2519-2524 (1996); and Smith et al., *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of anti-sense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed. (1989) Sinauer Associates: Sunderland, Mass.; or Deshpande, Mukund V., *Appl. Biochem. Biotechnol.*, 36:227 (1992).

Another non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example:

1.) The Primer Island Transposition Kit, available from Perkin Elmer Applied Biosystems, Branchburg, N.J., based upon the yeast Ty1 element;
2.) The Genome Priming System, available from New England Biolabs, Beverly, Mass., based upon the bacterial transposon Tn7; and 3.) the EZ::TN Transposon Insertion Systems, available from Epicentre Technologies, Madison, Wis., based upon the Tn5 bacterial transposable element].

Thus, within the context of the present invention, it may be useful to disrupt one of the acyltransferase genes of the invention. For example, it may be necessary to disrupt genes and pathways that diminish the existing fatty acid pool and/or that hydrolyze TAGs to regulate (and/or maximize) TAG accumulation.

Expression Systems, Cassettes and Vectors

The genes and gene products of the instant sequences described herein may be produced in microbial host cells, particularly in the cells of oleaginous yeasts (e.g., *Yarrowia lipolytica*). Expression in recombinant microbial hosts may be useful for the transfer of various fatty acids to TAGs.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of the instant ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (see U.S. Patent Application No. 60/482,263, incorporated herein by reference), phosphoglycerate mutase (see U.S. Patent Application No. 60/482,263, incorporated herein by reference), fructose-bisphosphate aldolase (see U.S. Patent Application No. 60/519,971, incorporated herein by reference), phosphoglucose-isomerase, phosphoglycerate kinase, etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the acyltransferase enzymes.

Preferred Microbial Hosts for Recombinant Expression of Acyltransferases

Host cells for expression of the instant genes and nucleic acid fragments may include microbial hosts that grow on a variety of feedstocks, including simple or complex carbohydrates, organic acids and alcohols and/or hydrocarbons over a wide range of temperature and pH values. Although the genes described in the instant invention have been isolated for expression in an oleaginous yeast, and in particular *Yarrowia lipolytica*, it is contemplated that because transcription, translation and the protein biosynthetic apparatus is highly conserved, any bacteria, yeast, algae and/or filamentous fungus will be a suitable host for expression of the present nucleic acid fragments.

Preferred microbial hosts are oleaginous organisms, such as oleaginous yeasts. These oleaginous organisms are naturally capable of oil synthesis and accumulation, wherein the total oil content can comprise greater than about 25% of the cellular dry weight, more preferably greater than about 30% of the cellular dry weight and most preferably greater than about 40% of the cellular dry weight. Additionally, there is basis for the use of these organisms for the production of PFUA's as seen in co-pending U.S. application Ser. No. 10/840,579, herein incorporated entirely by reference.

Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982, ATCC #90812 and/or LGAM S(7)1 (Papanikolaou S., and Aggelis G., *Bioresour. Technol.* 82(1): 43-9 (2002)).

Transformation of Microbial Hosts

Once the DNA encoding a polypeptide suitable for expression in an oleaginous yeast has been obtained, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell. More specific teachings applicable for oleaginous yeasts (i.e., *Yarrowia lipolytica*) include U.S. Pat. Nos. 4,880,741 and 5,071,764 and Chen, D. C. et al. (*Appl Microbiol Biotechnol.* 48(2):232-235-(1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin, hygromycin and the amino glycoside G418 are of interest, as well as ability to grow on media lacking uracil or leucine.

Following transformation, substrates suitable for the gene products of the instant sequences (and optionally other PUFA enzymes that are expressed within the host cell), may be produced by the host either naturally or transgenically, or they may be provided exogenously.

Fermentation Processes for Triacylglycerol Biosynthesis and Accumulation

The transformed microbial host cell is grown under conditions that optimize activity of fatty acid biosynthetic genes and acyltransferase genes. This leads to production of the greatest and the most economical yield of fatty acids, which can in turn be transferred to TAGs for storage. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon substrate may include one-carbon substrates (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea, glutamate). In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for fatty acid production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of fatty acids and TAGs in oleaginous yeast cells requires a two-stage process, since the metabolic state must be "balanced" between growth and synthesis/storage of fats. Thus, most preferably, a two-stage fermentation process is necessary for the production of oils in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of TAGs.

Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

It is contemplated that a variety of fermentation process designs may be applied, where commercial production of fatty acids and TAGs using the instant genes is desired. For example, commercial production of TAGs containing PUFAs from a recombinant microbial host may be produced by a batch, fed-batch or continuous fermentation process.

A batch fermentation process is a closed system wherein the media composition is set at the beginning of the process and not subject to further additions beyond those required for maintenance of pH and oxygen level during the process. Thus, at the beginning of the culturing process the media is inoculated with the desired organism and growth or metabolic activity is permitted to occur without adding additional substrates (i.e., carbon and nitrogen sources) to the medium. In batch processes the metabolite and biomass compositions of the system change constantly up to the time the culture is terminated. In a typical batch process, cells moderate through a static lag phase to a high-growth log phase and finally to a stationary phase, wherein the growth rate is diminished or halted. Left untreated, cells in the stationary phase will eventually die. A variation of the standard batch process is the fed-batch process, wherein the substrate is continually added to the fermentor over the course of the fermentation process. A fed-batch process is also suitable in the present invention. Fed-batch processes are useful when catabolite repression is apt to inhibit the metabolism of the cells or where it is desirable to have limited amounts of substrate in the media at any one time. Measurement of the substrate concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), herein incorporated by reference.

Commercial production of fatty acids using the instant genes may also be accomplished by a continuous fermentation process wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Purification of Fatty Acids

Fatty acids, including PUFAs, may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of fatty acids, including PUFAs, may include extraction with organic solvents, sonication, supercritical fluid extraction (e.g., using carbon dioxide), saponification and physical means such as presses, or combinations thereof. Of particular interest is extraction with methanol and chloroform in the presence of water (E. G. Bligh & W. J. Dyer, *Can. J. Biochem. Physiol.* 37:911-917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation, iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

DESCRIPTION OF PREFERRED EMBODIMENTS

The ultimate goal of the work described herein is the development of an oleaginous yeast that accumulates TAGs enriched in ω-3 and/or ω-6 PUFAs. Toward this end, acyltransferases must be identified that function efficiently in oleaginous yeasts, to enable synthesis and high accumulation of preferred TAGs in these hosts. Specifically, modification of the expression levels of these acyltransferases will enable increased transfer of fatty acids (and particularly, PUFAs) to TAGs. Thus, identification of efficient acyltransferases is necessary for the manipulation of the amount of ω-3/ω-6 PUFAs incorporated into the TAG fraction produced in host cells.

In the present invention, Applicants have isolated and cloned genes from *Yarrowia lipolytica* that encode PDAT and DGAT2. Confirmation of these genes' activity was provided based upon lower oil content (total fatty acids as a % of dry cell weight) in *Yarrowia* strains wherein disruption of the native PDAT, DGAT2, or PDAT and DGAT2 had occurred by targeted gene replacement through homologous recombination (Example 5). Additionally, over-expression of the PDAT of the invention in a PDAT/DGAT2 knockout strain of *Saccharomyces cerevisiae* lead to increased oil content (total fatty acids as a % of dry cell weight).

The Applicants conclude that these acyltransferase genes encoding PDAT and DGAT2 are useful for expression in various microbial hosts, and particularly for over-expression in oleaginous yeasts (e.g., the native host *Yarrowia lipolytica*). Additional benefits may result, since expression of the acyltransferases can also be put under the control of strong constitutive or regulated promoters that do not have the regulatory constraints of the native gene.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

*E. coli* TOP10 cells and *E. coli* Electromax DH10B cells were obtained from Invitrogen (Carlsbad, Calif.). Max Efficiency competent cells of *E. coli* DH5α were obtained from GIBCO/BRL (Gaithersburg, Md.). *E. coli* (XL1-Blue) competent cells were purchased from the Stratagene Company (San Diego, Calif.). *E. coli* strains were typically grown at 37° C. on Luria Bertani (LB) plates. General molecular cloning was performed according to standard methods (Sambrook et al., supra). Oligonucleotides were synthesized by Sigma-Genosys (Spring, Tex.). PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR, Inc., (Madison, Wis.).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "pmole" mean micromole(s), "g" means gram(s), "µg" means microgram(s), "ng" means nanogram(s), "U" means unit(s), "bp" means base pair(s) and "kB" means kilobase(s).

Cultivation of *Yarrowia lipolytica*

*Yarrowia lipolytica* strains ATCC #76982 and ATCC #90812 were purchased from the American Type Culture Collection (Rockville, Md.). *Y. lipolytica* strains were usually grown at 28° C. on YPD agar (1% yeast extract, 2% bactopeptone, 2% glucose, 2% agar). For selection of transformants, minimal medium (0.17% yeast nitrogen base (DIFCO Laboratories, Detroit, Mich.) without ammonium sulfate or amino acids, 2% glucose, 0.1% proline, pH 6.1) was used. Supplements of adenine, leucine, lysine and/or uracil were added as appropriate to a final concentration of 0.01%.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

Construction of Plasmids Suitable for Gene Expression in *Yarrowia lipolytica*

The present Example describes the construction of plasmids pY5, pY5-13, pY5-20 and pLV5.

Construction of Plasmid pY5

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in *Yarrowia lipolytica*, as diagrammed in FIG. 3. First, the partially-digested 3598 bp EcoRI fragment containing the ARS18 sequence and LEU2 gene of pINA532 was subcloned into the EcoRI site of pBluescript (Strategene, San Diego, Calif.) to generate pY2. The TEF promoter (Muller S., et al., *Yeast*, 14:1267-1283 (1998)) was amplified from *Y. lipolytica* genomic DNA by PCR using TEF5' (SEQ ID NO:1) and TEF3' (SEQ ID NO:2) as primers. PCR amplification was carried out in a 50 µl total volume containing: 100 ng *Yarrowia* genomic DNA, PCR buffer containing 10 mM KCl, 10 mM $(NH_4)_2SO_4$, 20 mM Tris-HCl (pH 8.75), 2 mM $MgSO_4$, 0.1% Triton X-100, 100 µg/mL BSA (final concentration), 200 µM each deoxyribonucleotide triphosphate, 10 pmole of each primer and 1 µl of PfuTurbo DNA polymerase (Stratagene). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator was amplified by PCR using pINA532 as template and XPR5' (SEQ ID NO:3) and XPR3' (SEQ ID NO:4) as primers. The PCR amplification was carried out in a 50 µl total volume, using the components and conditions described above. The 179 bp PCR product was digested with SacII and then ligated into the SacII site of pY4 to generate pY5. Thus, pY5 (shown in FIG. 3) is useful as a *Yarrowia-E. coli* shuttle plasmid containing:
1.) a *Yarrowia* autonomous replication sequence (ARS18);
2.) a ColE1 plasmid origin of replication;
3.) an ampicillin-resistance gene (Amp$^R$), for selection in *E. coli*;
4.) a *Yarrowia* LEU2 gene (E.C. 1.1.1.85, encoding isopropylmalate isomerase), for selection in *Yarrowia*;
5.) the translation elongation promoter (TEF), for expression of heterologous genes in *Yarrowia*; and
6.) the extracellular protease gene terminator (XPR2) for transcriptional termination of heterologous gene expression in *Yarrowia*.

Construction of Plasmid pY5-13 pY5-13 (FIG. 3) was constructed as a derivative of pY5 to facilitate subcloning and heterologous gene expression in *Yarrowia lipolytica*. Specifically, pY5-13 was constructed by 6 rounds of site-directed mutagenesis using pY5 as template. Both SalI and ClaI sites were eliminated from pY5 by site-directed mutagenesis using oligonucleotides YL5 and YL6 (SEQ ID NOs:5 and 6) to generate pY5-5. A SalI site was introduced into pY5-5 between the LEU2 gene and the TEF promoter by site-directed mutagenesis using oligonucleotides YL9 and YL10 (SEQ ID NOs:7 and 8) to generate pY5-6. A PacI site was introduced into pY5-6 between the LEU2 gene and ARS18 using oligonucleotides YL7 and YL8 (SEQ ID NOs:9 and 10) to generate pY5-8. A NcoI site was introduced into pY5-8 around the translation start codon of the TEF promoter using oligonucleotides YL3 and YL4 (SEQ ID NOs:11 and 12) to generate pY5-9. The NcoI site inside the LEU2 gene of pY5-9 was eliminated using YL1 and YL2 oligonucleotides (SEQ ID NOs:13 and 14) to generate pY5-12. Finally, a BsiWI site was introduced into pY5-12 between the ColEI and XPR2 region using oligonucleotides YL61 and YL62 (SEQ ID NOs:15 and 16) to generate pY5-13.

Construction of Plasmids pY5-20 and pLV5

Plasmid pY5-20 is a derivative of pY5. It was constructed by inserting a Not I fragment containing a chimeric hygromycin resistance gene into the Not I site of pY5. Specifically, the *E. coli* hygromycin resistance gene (SEQ ID NO:17; "HPT"; Kaster, K. R., et al., *Nucleic Acids Res.* 11:6895-6911 (1983)) was PCR amplified for expression. The chimeric gene had the hygromycin resistance ORF under the control of the *Y. lipolytica* TEF promoter.

Plasmid pLV5 is a derivative of pY5-20. It was constructed by replacing the hygromycin resistant gene with the *Yarrowia* Ura3 gene. A 1.7 kB DNA fragment (SEQ ID NO:19) containing the *Yarrowia* Ura3 gene was PCR amplified using oligonucleotides KU5 and KU3 (SEQ ID NOs:21 and 22) as primers and *Yarrowia* genomic DNA as template.

Example 2

Cloning of a Partial *Yarrowia lipolytica* Acyl-CoA:Diacylglycerol Acyltransferase (DGAT2) Gene and Disruption of the Endogenous DGAT2 Gene The present Example describes the use of degenerate PCR primers to isolate a partial coding sequence of the *Yarrowia lipolytica* DGAT2 and the use of the partial sequence to disrupt the native gene in *Y. lipolytica*.

Cloning of a Partial Putative DGAT2 Sequence from *Yarrowia lipolytica* by PCR Using Degenerate PCR Primers and Chromosome Walking Genomic DNA was isolated from *Y. lipolytica* (ATCC #76982) using a DNeasy Tissue Kit (Qiagen, Catalog #69504) and resuspended in kit buffer AE at a DNA concentration of 0.5 µg/µl. PCR amplifications were performed using the genomic DNA as template and several sets of degenerate primers designed to encode conserved amino acid sequences among different known DGAT2s (i.e., GenBank Accession Nos. NC_001147 [*Saccharomyces cerevisiae*] and AF391089 and AF391090 [*Mortierella ramanniana*]). The best results were obtained with degenerate primers P7 and P8, as shown in the Table below.

TABLE 3

Degenerate Primers Used For Amplification Of A Partial Putative DGAT2

| Primer Set | Description | Degenerate Nucleotide Sequence | Corresponding Amino Acid Sequence |
|---|---|---|---|
| P7 | (32) 29-mers | 5'-AACTACATCTTCGGCTAY CAYCCNCAYGG-3' (SEQ ID NO: 23) | NYIFGYHPHG (SEQ ID NO: 24) |
| P8 | (48) 29-mers | 5'-AGGGACTCGGAGGCGC CGCCNCANACDAT-3' (SEQ ID NO: 25) | complementary to IVVGGASESL (SEQ ID NO: 26) |

[Note:
Abbreviations are standard for nucleotides and proteins. The nucleic acid degeneracy code used is as follows: Y = C/T; D = A/G/T; and N = A/C/G/T.]

The PCR was carried out in a RoboCycler Gradient 40 PCR machine (Stratagene) using the manufacturer's recommendations and Accuprime Taq polymerase (Invitrogen). Amplification was carried out as 25 follows: initial denaturation at 95° C. for 1 min, followed by 30 cycles of denaturation at 95° C. for 30 sec, annealing at 55° C. for 1 min, and elongation at 72° C. for 1 min. A final elongation cycle at 72° C. for 10 min was carried out, followed by reaction termination at 4° C.

The expected PCR product (ca. 264 bp) was detected by 4% NuSieve (FMC) agarose gel electrophoresis, isolated, purified, cloned into the TOPO® cloning vector (Invitrogen), and sequenced. The resultant sequence (contained within SEQ ID NO:30) had homology to known DGAT2s, based on BLAST program analysis (Basic Local Alignment Search Tool; Altschul, S. F., et al., *J. Mol. Biol.* 215:403-410 (1993).

Using the 264 bp fragment as an initiation point, a 673 bp fragment was obtained by chromosome walking using the TOPO® Walker Kit (Invitrogen, Catalog #K8000-01). The chromosome walking was carried out in 6 steps, as described briefly below:
1.) Genomic DNA (5 μg) was digested with restriction enzymes Pst I or Sac I, leaving a 3' overhang;
2.) Digested DNA was treated with 0.1 U calf intestinal alkaline phosphatase to dephosphorylate DNA;
3.) Primer extension was performed, using the DGAT2 specific primer P80 (SEQ ID NO:27) and Taq polymerase;
4.) TOPO® Linker (1 μl) was added and the reaction was incubated at 37° C. for 5 min to ligate TOPO® Linker to the DNA;
5.) PCR was performed using the DGAT2 gene specific primer, P81 (SEQ ID NO:28) and LinkAmp primer 1 (SEQ ID NO:29); and
6.) The newly amplified fragment was sequenced with primer P81 and LinkAmp primer 1.

The sequence of the 673 bp fragment obtained by chromosome walking also showed homology to known DGAT2 sequences.

Targeted Disruption of the *Yarrowia lipolytica* DGAT2 Gene

Targeted disruption of the DGAT2 gene in *Y. lipolytica* ATCC #90812 and ATCC #76982 was carried out by homologous recombination-mediated replacement of the endogenous DGAT2 gene with a targeting cassette designated as plasmid pY21 DGAT2. pY21 DGAT2 was derived from plasmid pY20 (Example 1). Specifically, pY21 DGAT2 was created by inserting a 570 bp Hind III/Eco RI fragment into similarly linearized pY20. The 570 bp DNA fragment contained (in 5' to 3' orientation): 3' homologous sequence from position +1090 to +1464 (of the coding sequence (ORF) in SEQ ID NO:30), a Bgl II restriction site and 5' homologous sequence from position +906 to +1089 (of the coding sequence (ORF) shown in SEQ ID NO:30). The fragment was prepared by PCR amplification of 3' and 5' sequences from the 673 bp DGAT2 PCR product obtained by chromosome walking using two pairs of PCR primers, P95 and P96 (SEQ ID NOs:32 and 33), and P97 and P98 (SEQ ID NOs:34 and 35), respectively.

pY21 DGAT2 was linearized by Bgl II restriction digestion and transformed into mid-log phase *Y. lipolytica* ATCC #90812 and ATCC #76982 cells by the lithium acetate method according to the method of Chen, D. C. et al. (*Appl Microbiol Biotechnol.* 48(2):232-235-(1997)). Briefly, *Y. lipolytica* ATCC #90821 and *Y. lipolytica* ATCC #76982 were streaked onto YPD plates and grown at 30° C. for approximately 18 hr. Several large loopfuls of cells were scraped from the plates and resuspended in 1 mL of transformation buffer containing:
  2.25 mL of 50% PEG, average MW 3350;
  0.125 mL of 2 M Li acetate, pH 6.0;
  0.125 mL of 2 M DTT; and
  50 μg sheared salmon sperm DNA.

About 500 ng of plasmid DNA were incubated in 100 μl of resuspended cells and maintained at 39° C. for 1 hr with vortex mixing at 15 min intervals. The cells were plated onto YPD hygromycin selection plates and maintained at 30° C. for 2 to 3 days.

Four *Y. lipolytica* ATCC #76982 hygromycin-resistant colonies and fourteen *Y. lipolytica* ATCC #90812 hygromycin-resistant colonies were isolated and screened for targeted disruption by PCR. One set of PCR primers (P115 [SEQ ID NO:36] and P116 [SEQ ID NO:37]) was designed to amplify a specific junction fragment following homologous recombination. Another pair of PCR primers (P115 and P112 [SEQ ID NO:38]) was designed to detect the native gene. All (4 of 4) of the hygromycin-resistant colonies of ATCC #76982 strains were positive for the junction fragment and negative for the native fragment; and, 2 of the 14 hygromycin-resistant colonies of ATCC #90812 strains were positive for the junction fragment and negative for the native fragment. Thus, targeted integration was confirmed in these 6 strains. Disruption of the gene was further confirmed by GC analysis of total lipids of one of the disrupted strains, designated as "S-D" (see Example 5).

Example 3

Cloning of a Partial *Yarrowia lipolytica* Phospholipid:Diacylglycerol Acyltransferase (PDAT) Gene and Disruption of the Endogenous PDAT Gene The present Example describes the use of degenerate PCR primers to isolate a partial coding sequence of *Y. lipolytica* PDAT and the use of the partial sequence to disrupt the native gene in *Y. lipolytica*.

Cloning of a Partial Putative PDAT Sequence from *Yarrowia lipolytica* by PCR Using Degenerate PCR Primers and Chromosome Walking Genomic DNA was isolated from *Y. lipolytica* (ATCC #76982) using a DNeasy Tissue Kit (Qiagen, Catalog #69504) and resuspended in kit buffer AE at a DNA concentration of 0.5 μg/μl. PCR amplifications were performed using genomic DNA as the template and several pairs of degenerate primers encoding conserved amino acid sequences in different known PDATs (GenBank Accession Nos. NP 190069 and AB006704 [(gi:2351069*Arabidopsis thaliana*], and NP_596330 *[Schizosaccharomyces pombe]*; and the *Saccharomyces cerevisiae* Lro 1 gene [Dahlqvist et al., *Proc. Natl. Acad. Sci. USA* 97:6487 (2000)]). The best results were obtained with degenerate primers P26 and P27, as shown in the Table below.

TABLE 4

Degenerate Primers Used For Amplification Of A Partial Putative PDAT

| Primer Set | Description | Degenerate Nucleotide Sequence | Corresponding Amino Acid Sequence |
| --- | --- | --- | --- |
| P26 | (32) 29-mers | 5'-ATGCTGGACAAGGAGACCGGNCTNGAYCC-3' (SEQ ID NO: 39) | MLDKETGLDP (SEQ ID NO: 40) |
| P27 | (16) 33-mers | 5'-CCAGATGACGTCGCCGCCCTTGGGNARCATNGA-3' (SEQ ID NO: 41) | complementary to SMLPKGGEVIW (SEQ ID NO: 42) |

[Note:
Abbreviations are standard for nucleotides and proteins. The nucleic acid degeneracy code used is as follows: R = A/G; Y = C/T; and N = A/C/G/T.]

The PCR was carried out in a RoboCycler Gradient 40 PCR machine (Stratagene), using the amplification conditions described in Example 2. The expected PCR product (ca. 600 bp) was detected by 4% NuSieve (FMC) agarose gel electrophoresis, isolated, purified, cloned into the TOPO® cloning vector (Invitrogen) and sequenced. The resultant sequence (contained within SEQ ID NO:45) had homology to known PDATs, based on BLAST program analysis (Basic Local Alignment Search Tool; Altschul, S. F., et al., *J. Mol. Biol.* 215:403-410 (1993).

Targeted Disruption of *Yarrowia lipolytica* PDAT Gene

Following the sequencing of this ca. 600 bp partial coding region for PDAT, a larger DNA fragment encoding this sequence was discovered in the public *Y. lipolytica* database of the "Yeast project Genolevures" (Center for Bioinformatics, LaBRI, Talence Cedex, France. This allowed isolation of a 1008 bp genomic DNA fragment comprising a portion of the PDAT gene from *Y. lipolytica* ATCC #90812 using PCR primers P39 and P42 (SEQ ID NOs:43 and 44).

Targeted disruption of the PDAT gene in *Y. lipolytica* ATCC #90812 was carried out by homologous recombination-mediated replacement of the endogenous PDAT gene with a targeting cassette designated as pLV13. pLV13 was derived from plasmid pLV5 (Example 1). Specifically, pLV13 was created by inserting a 992 bp Bam HI/Eco RI fragment into similarly linearized pLV5. The 992 bp DNA fragment contained (in 5' to 3' orientation): 3' homologous sequence from position +877 to +1371 (of the coding sequence (ORF) in SEQ ID NO:45), a Bgl II restriction site and 5' homologous sequence from position +390 to +876 (of the coding sequence (ORF) in SEQ ID NO:45). The fragment was prepared by PCR amplification of 3' and 5' sequences from the 1008 bp PCR product described above, using PCR primers P39 and P41 (SEQ ID NOs:43 and 47) and P40 and P42 (SEQ ID NOs:48 and 44), respectively.

pLV13 was linearized by Bgl II restriction digestion and was transformed into mid-log phase *Y. lipolytica* ATCC #90812 cells by the lithium acetate method (Example 2). The cells were plated onto Bio101 DOB/CSM-Ura selection plates and maintained at 30° C. for 2 to 3 days.

Ten *Y. lipolytica* ATCC #90812 colonies were isolated and screened for targeted disruption by PCR. One set of PCR primers (P51 [SEQ ID NO:49] and P52 [SEQ ID NO:50]) was designed to amplify a targeting cassette. Another set of PCR primers (P37 [SEQ ID NO:51] and P38 [SEQ ID NO:52]) was designed to detect the native gene. Ten of the ten strains were positive for the junction fragment and 3 of the 10 strains were negative for native fragment, thus confirming successful targeted integration in these 3 strains. Disruption of the gene was further confirmed by GC analysis of total lipids in one of the disrupted strains, designated as "S—P" (see Example 5).

Example 4

Construction of a *Yarrowia lipolytica* Double Knockout Strain Containing Disruptions in Both PDAT and DGAT2 Genes The present Example describes the creation of a double knockout strain that was disrupted in both PDAT and DGAT2 genes.

Specifically, the *Y. lipolytica* ATCC#90812 hygromycin-resistant "S-D" mutant (containing the DGAT2 disruption from Example 2) was transformed with plasmid pLV13 (from Example 3) and transformants were screened by PCR, as described in Example 3. Two of twelve transformants were confirmed to be disrupted in both the DGAT2 and PDAT genes. Disruption of the gene was further confirmed by GC analysis of total lipids in one of the disrupted strains, designated as "S-D-P" (see Example 5).

Example 5

Determination of Tag Content in Mutant and Wildtype *Yarrowia lipolytica* Strains (ATCC #90812)

Single colonies of wildtype and mutant *Y. lipolytica* (ATCC #90812) containing disruptions in either the PDAT (from Example 3), DGAT2 (from Example 2) or PDAT and DGAT2 (from Example 4) genes were separately grown according to two different culture conditions, as described below:

Growth Condition 1: Cells were grown in 3 mL minimal media (formulation/L: 20 g glucose, 1.7 g yeast nitrogen base, 1 g L-proline, 0.1 g L-adenine, 0.1 g L-lysine, pH 6.1) at 30° C. to an $OD_{600}$~1.0. The cells were harvested, washed in distilled water, speed vacuum dried and subjected to GC analysis of the lipids following thin layer chromatography (TLC) (infra).

Growth Condition 2: Cells were grown in a 50 mL culture using conditions that induce oleaginy. Specifically, one loopful of cells from plates were inoculated into 3 mL YPD medium and grown overnight on a shaker (300 rpm) at 30° C. The cells were harvested and washed once in 0.9% NaCl and resuspended in 50 mL of high glucose medium [formulation/L: 7 g $KH_2PO_4$, 2 g $K_2HPO_4$, 2 g $MgSO_4.7H_2O$, 80 g glucose, 0.1 g leucine, 0.1 g Uracil, and 0.1 g L-lysine, pH 5.0]. Cells were then grown on a shaker as above for 48 hrs. Cells were washed in water and the cell pellet was lophilized. Twenty (20) mg of dry cell weight was used for total fatty acid by GC analysis and the oil fraction following TLC (infra) and GC analysis.

Thin Layer Chromatography

The methodology used for TLC is described below in the following five steps:

1) The internal standard of 15:0 fatty acid (10 µl of 10 mg/mL) was added to 2 to 3 mg dry cell mass, followed by extraction of the total lipid using a methanol/chloroform method.
2) Extracted lipid (50 µl) was blotted across a light pencil line drawn approximately 1 inch from the bottom of a 5×20 cm silica gel 60 plate, using 25-50 µl micropipettes.
3) The TLC plate was then dried under $N_2$ and was inserted into a tank containing about ~100 mL 80:20:1 hexane:ethyl ether:acetic acid solvent.
4) After separation of bands, a vapor of iodine was blown over one side of the plate to identify the bands. This permitted samples on the other side of the plate to be scraped using a razor blade for further analysis.
5) Basic transesterification of the scraped samples and GC analysis was performed, as described in the General Methods.

Results from GC Analysis

GC results are shown below in Tables 5 and 6. Cultures are described as the "S" strain (wildtype), "S—P" (PDAT knockout), "S-D" (DGAT2 knockout), and "S—P-D" (PDAT and DGAT2 knockout). Abbreviations utilized are: WT=wildtype; TFAs=total fatty acids; dcw=dry cell weight; and, % WT=% relative to the wild type ("S" strain).

TABLE 5

Lipid Content In *Yarrowia* ATCC #90812 Strains Disrupted In PDAT, DGAT2 Or Both, Grown In Minimal Media

| Culture | Fraction | TFAs | |
|---|---|---|---|
| | | % dcw | % WT |
| S strain (WT) | total | 12 | 100 |
| | TAG | 15 | 100 |
| | phospholipid | 5 | |
| S-P | total | 11 | 89 |
| | TAG | 14 | 98 |
| | phospholipid | 5 | |

TABLE 5-continued

Lipid Content In *Yarrowia* ATCC #90812 Strains Disrupted
In PDAT, DGAT2 Or Both, Grown In Minimal Media

|  |  | TFAs | |
|---|---|---|---|
| Culture | Fraction | % dcw | % WT |
| S-D | total | 10 | 81 |
|  | TAG | 10 | 66 |
|  | phospholipid | 4 |  |
| S-P-D | total | 8 | 64 |
|  | TAG | 7 | 50 |
|  | phospholipid | 3 |  |

TABLE 6

Lipid Content In *Yarrowia* ATCC #90812 Strains Disrupted
In PDAT, DGAT2 Or Both, Grown Under Oleaginous Conditions

|  | dcw, | Lipid | TFAs | |
|---|---|---|---|---|
| Culture | mg | fraction | µg | % dcw | % WT |
| S strain (WT) | 32.0 | Total | 797 | 15.9 | 100 |
| S-D | 37.5 | Total | 329 | 6.4 | 40 |
| S-P | 28.8 | Total | 318 | 6.0 | 38 |
| S-P-D | 31.2 | Total | 228 | 4.3 | 27 |
| S strain (WT) | 32.0 | TAG | 697 | 13.9 | 100 |
| S-D | 37.5 | TAG | 227 | 4.4 | 32 |
| S-P | 28.8 | TAG | 212 | 4.0 | 29 |
| S-P-D | 31.2 | TAG | 122 | 2.3 | 17 |

The results shown above indicated that the disrupted strains showed lower oil content (TFAs % dcw) as compared to the wild type strain. And, the results shown in Tables 5 and 6 confirmed that the *Y. lipolytica* genes encoding both DGAT2 and PDAT contribute to oil biosynthesis in the native organism, with DGAT2 acting as the major contributor to oil biosynthesis during oleaginy. Surprisingly, however, the results also suggest the existence of additional *Yarrowia* gene(s) involved in oil biosynthesis.

Example 6

Cloning of Full-Length *Yarrowia lipolytica* DGAT2 and PDAT Genes

The present Example describes the recovery of the genomic sequences flanking the disrupted DGAT2 and PDAT genes by plasmid rescue, using the sequence in the rescued plasmid to PCR the intact ORF of the native gene. The full-length genes and their deduced amino acid sequences are compared to other fungal DGAT2 and PDAT sequences, respectively.

Plasmid Rescue of *Yarrowia lipolytica* DGAT2 and PDAT Genes

Since the acyltransferase genes were disrupted by the insertion of the entire pY21DGAT2 and pLV13 vectors that each contained an *E. coli* ampicillin-resistant gene and *E. coli* ori, it was possible to rescue the flanking PDAT and DGAT2 sequences in *E. coli*. For this, genomic DNA of *Y. lipolytica* strain "S-D" (carrying the disrupted DGAT2 gene; Example 2) and *Y. lipolytica* strain "S—P" (carrying the disrupted PDAT gene; Example 3) was isolated using the DNeasy Tissue Kit. Specifically, 10 µg of the genomic DNA was digested with 50 U of the following restriction enzymes in a reaction volume of 200 µl: for DGAT2—Age/and Nhe I; for PDAT—Kpn I, Pac I and Sac I. Digested DNA was extracted with phenol:chloroform and resuspended in 40 µl deionized water.

The digested DNA (10 µl) was self-ligated in a 200 µl ligation mixture containing 3 U T4 DNA ligase. Each ligation reaction was carried out at 16° C. for 12 hrs. The ligated DNA was extracted with phenol:chloroform and resuspended in 40 µl deionized water. Finally, 1 µl of the resuspended ligated DNA was used to transform *E. coli* by electroporation and plated on LB containing ampicillin (Ap). Ap-resistant transformants were isolated and analyzed for the presence of plasmids. The following insert sizes were found in the recovered or rescued plasmids (Tables 7 and 8):

TABLE 7

Insert Sizes Of Recovered DGAT2 Plasmids, According
To Restriction Enzyme

| Enzyme | plasmid insert size (kB) |
|---|---|
| AgeI | 2.3 |
| NheI | 9.5 |

TABLE 8

Insert Sizes Of Recovered PDAT Plasmids, According
To Restriction Enzyme

| Enzyme | plasmid insert size (kB) |
|---|---|
| kpn I | 6.9 |
| Sac I | 5.4 |
| Sph I | 7.0 |

Sequencing of the DGAT2 rescued plasmids was initiated with sequencing primers P79 (SEQ ID NO:53) and P95 (SEQ ID NO:32). In contrast, sequencing of the PDAT plasmids was initiated with sequencing primers P84 (SEQ ID NO:54) and P85 (SEQ ID NO:55).

Based on the sequencing results, a full-length gene encoding the *Y. lipolytica* DGAT2 gene was assembled (2119 bp; SEQ ID NO:30). Specifically, the sequence encoded an open reading frame (ORF) of 1545 bases (nucleotides +291 to +1835 of SEQ ID NO:30), while the deduced amino acid sequence was 514 residues in length (SEQ ID NO:31). Since this ORF has an initiation codon ('ATG') at position 1, as well as at positions 56 and 160, it contains at least two additional nested (smaller) ORFs. Specifically, one ORF is 1380 bases long (nucleotides +456 to +1835 of SEQ ID NO:30), with a deduced amino acid sequence of 459 residues (SEQ ID NO:78); another ORF is 1068 bases long (nucleotides +768 to +1835 of SEQ ID NO:30) with a deduced amino acid sequence of 355 residues (SEQ ID NO:79), encoded by SEQ ID NO:86.

The ORF encoded by SEQ ID NO:86 has a high degree of similarity to other known DGAT enzymes and because disruption in SEQ ID NO:86 eliminated DGAT function of the native gene, the polypeptide of SEQ ID NO:79 has been identified as clearly having DGAT functionality. For example, the *Yarrowia lipolytica* DGAT2 that is 355 residues in length (i.e., SEQ ID NO:79) is only 16 amino acids shorter than the *Saccharomyces cerevisiae* protein, 7 amino acids shorter than the *Mortierella ramanniana* type 2A protein and 2 amino acids shorter than the *M. ramanniana* type 2B protein (infra). Despite this hypothesis, however, it may be useful to test the contribution of all of the three ORFs encoded by SEQ ID NOs:31, 78 and 79 for expression of the *Yarrowia* DGAT2 protein.

A comparison of SEQ ID NO:79 (i.e., the deduced amino acid sequence of the 355 residues; *Y. lipolytica* DGAT2

("Yl")) was made with the known fungal DGAT2s shown in Table 9 below, using the ClustalW (Slow/Accurate, Gonnet) program of the DNASTAR software package (Madison, Wis.).

TABLE 9

Description of Known Fungal DGAT2s

| Organism | Abbreviation | Reference |
|---|---|---|
| Saccharomyces cerevisiae DGA1 gene [Locus NP_014888] | Sc | GenBank Accession No. NC_001147 |
| Mortierella ramanniana DGAT2 type 2A | MrA | GenBank Accession No. AF391089 |
| Mortierella ramanniana DGAT2 type 2B | MrB | GenBank Accession No. AF391090 |

This comparison revealed the Pair Distances shown as percent similarity in FIG. 4A. Thus, comparison of the deduced amino acid sequences of other fungal homologs to the *Y. lipolytica* DGAT2 described herein as SEQ ID NO:79 revealed less than 38.4% amino acid identity.

Following sequencing and analysis of the DGAT2 proteins described above, a *Yarrowia lipolytica* DGAT2 protein sequence was published as part of the Genolevures project (sponsored by the Center for Bioinformatics, LaBRI, bâtiment A30, Université Bordeaux 1, 351, cours de la Libération, 33405 Talence Cedex, France. Specifically, the sequence disclosed therein was identified as ORF YALI-CDS2240.1, encoding 514 amino acids, and the protein was reported to share some similarities with tr|Q08650 *Saccharomyces cerevisiae* YOR245C DGA1 acyl-CoA:diacylglycerol acyltransferase.

In a manner similar to that used to deduce the full-length sequence of DGAT2, a full-length gene encoding the *Y. lipolytica* PDAT gene was assembled (2326 bp; SEQ ID NO:45) based on sequencing results. Specifically, the sequence encoded an open reading frame of 1944 bases (nucleotides +274 to +2217 of SEQ ID NO:45), while the deduced amino acid sequence was 648 residues in length (SEQ ID NO:46). A comparison of the deduced amino acid sequence of the *Y. lipolytica* PDAT ("Yl") was made with other known fungal PDATs (as shown in Table 10) using the analysis methods described above.

TABLE 10

Description of Known or Putative Fungal PDATs

| Organism | Abbreviation | Reference |
|---|---|---|
| Saccharomyces cerevisiae Lro 1 gene | Sc | Dahlqvist et al., Proc. Natl. Acad. Sci. USA 97: 6487 (2000) |
| Arabidopsis thaliana "At3g44830" gene (lecithin:cholesterol acyltransferase family protein/LACT family protein) | At2 | GenBank Accession No. NP 190069 [gi: 15230521] |
| Arabidopsis thaliana | At1 | GenBank Accession No. AB006704 [gi: 2351069] |
| Schizosaccharomyces pombe "SPBC776.14" gene | Sp | GenBank Accession No. NP_596330 [gi: 19113122] |

The results of this comparison are shown as Pair Distances in FIG. 4B. The results demonstrated that the *Y. lipolytica* PDAT possessed less than 47.1% amino acid identity with the other PDAT homologs.

Following sequencing and analysis of the PDAT protein described above, the *Yarrowia lipolytica* PDAT protein sequence was published as part of the Genolevures project (supra). The PDAT sequence disclosed therein was identified as ORF YALI-CDS1359.1, encoding 648 amino acids, and the protein was reported to share some similarities to sp|P40345 *Saccharomyces cerevisiae* YNR008w LRO1, a lecithin cholesterol acyltransferase-like gene which mediates diacylglycerol esterification.

Example 7

Functional Expression of *Yarrowia lipolytica* PDAT in *Saccharomyces cerevisiae*

The present Example describes the expression of the *Yarrowia lipolytica* gene (SEQ ID NO:45) encoding PDAT in a wildtype and DGAT2/PDAT knockout strain of *Saccharomyces cerevisiae*.

*Saccharomyces cerevisiae* Strains

The following two *Saccharomyces cerevisiae* strains were obtained from Open Biosystems (Huntsville, Ala.)

BY4741 WT (MATa, his3 Δ1, leu2Δ0, met15Δ0, and ura3Δ0); and,

BY4741 dga1 (MATa, his3Δ1, leu2Δ0, met15Δ0, and ura3Δ0), dga1 (comprising a mutant DGAT2 gene).

Haploid strain BY4741 dga1/lro1 was derived from strain BY4741 dga1 by disrupting the Lro1 gene encoding PDAT according to the methodology recommended by Open Biosytem, as described below.

First, a *S. cerevisiae* LRO 1 targeting cassette was made by PCR amplifying the *S. cerevisiae* LEU2 gene from plasmid pJJ250 (Jones, J. S, and I. Prakash, *Yeast* 6:363-366 (1990)). This was accomplished using the following primer pair:

UP 161 (SEQ ID NO:84), an 81-mer comprised of 45 bp of 5' untranslated region of the LRO 1 gene at the primer's 5' end, followed by 36 bp of the 5' end of the LEU2 gene; and, LP 162 (SEQ ID NO:85), an 81-mer comprised of 45 bp of 3' untranslated region of the LRO 1 gene at the primer's 5' end, followed by 36 bp of the 3' end of the LEU2 gene.

The expected 1901 bp PCR product was purified following agarose gel electrophoresis and transformed into strain BY4741 dga1 by the standard lithium acetate method (*Current Protocols in Molecular Biology*, P13.7.1). Transformants were selected on DOB-Leu plates (formulation/L: 43.7 g DOBA [BIO 101® Systems, Catalog #4026-012; Krackeler Scientific, Inc., Albany, N.Y.] and 0.69 g CSM-Leu [BIO 101® Systems, Catalog #4510-512; Krackeler Scientific, Inc.]). After 3 days, more than 100 transformant colonies were visible; six of these colonies were selected for PCR analysis. The LRO 1 knockout was confirmed in all 6 colonies, thus yielding a double knockout of *S. cerevisiae*, identified herein as strain BY4741 dga1/lro1.

Synthesis of Plasmid pScGPD-YlPDAT (Comprising a GPD::PDAT::ADH1 Chimeric Gene)

The *S. cerevisiae* GPD (TDH3 gene, encoding glyceraldehyde-3-phosphate dehydrogenase) promoter was amplified using primers GPD-1 (SEQ ID NO:80) and GPD-2 (SEQ ID NO:81), using standard conditions. The 653 bp PCR product was cloned into pGEM-T (Promega, Madison, Wis.). The resulting plasmid, pGPD-GEM, was cut with Sac II and Spe I. The 673 bp fragment containing the GPD promoter was isolated and cloned into the *S. cerevisiae* vector pRS426 digested with Sac II and Spe I, to form plasmid pGPD426

[pRS426 is a yeast autonomously replicating vector that carries the URA gene (Christianson T. W., et al., *Gene* 110:119-122 (1992))].

The *S. cerevisiae* ADH1 (alcohol dehydrogenase gene) terminator region was amplified using primers ADHT-1 (SEQ ID NO:82) and ADHT-2 (SEQ ID NO:83). The 330 bp PCR product was cut with Xho I and Kpn I, and cloned into pGPD426 between Xho I and Kpn I, resulting in formation of plasmid pGPD426N.

Plasmid pGPD426N was cut with Nco I and Not I and then a Nco I-Not I fragment carrying the *Yarrowia* PDAT ORF was cloned into it. Thus, the resultant plasmid pScGPD-YlPDAT contained the *Yarrowia lipolytica* PDAT ORF under the control of the *Saccharomyces cerevisiae* GPD promoter (i.e., a GPD::PDAT::ADH1 chimeric gene).

Transformation and Expression of the *Yarrowia lipolytica* PDAT in *Saccharomyces cerevisiae*

Saccharomyces cerevisiae strain BY4741 dga1/lro1 was transformed by the standard lithium acetate method (supra) with either pGPD426N (the "control") or with yeast plasmid pScGPD-YlPDAT (comprising GOD::PDAT::ADH1). Positive transformants (i.e., URA prototrophs) were picked and streaked onto Ura dropout plates (i.e., DOB-Ura plates (formulation/L: 43.7 g DOBA [BIO 101® Systems, Catalog #4026-012; Krackeler Scientific, Inc., Albany, N.Y.] and 0.69 g CSM-Leu [BIO 101® Systems, Catalog #4511-212; Krackeler Scientific, Inc.])) and pre-cultivated for 1-2 days. A loop of cells was picked and inoculated into 3 mL Ura dropout medium and cultivated overnight at 30° C. The preculture was transferred to 40 mL medium and cells were grown for 52 hr prior to being harvested, washed in water, and lyophilized. The dry cell weight ("dcw") was determined and dry cell mass was analyzed by direct base transesterification.

TABLE 11

Lipid Content In *Saccharomyces cerevisiae* Strains Disrupted In PDAT And DGAT2

| Strain | Plasmid | mg of dcw used for GC | TFA mg | TFA % dcw |
|---|---|---|---|---|
| BY4741 dga1/lro1 | pGPD426N (control) | 8.3 | 67 | 0.8 |
| BY4741 dga1/lro1 | pScGPD-YlPDAT | 9.4 | 154 | 1.6 |

Total fatty acids, measured as a percent of the dry cell weight (column 5, "TFA % dcw") was doubled in the pScGPD-YlPDAT transformant as compared to that in the control (comprising the vector alone). Since *Saccharomyces cerevisiae* is not an oleaginous organism, this difference in the amount of total fatty acids produced is significant. These results confirmed that the enzyme encoded by SEQ ID NO:45 corresponds to a functional *Yarrowia lipolytica* PDAT enzyme.

Example 8

Isolation Of The *Yarrowia* Glyceraldehyde Phosphate Dehydrogenase (GPD) Promoter Region The present Example describes the identification of the promoter region (SEQ ID NO:56) of the *Yarrowia lipolytica* gene encoding glyceraldehyde phosphate dehydrogenase, by use of primers derived from conserved regions of other GPD sequences.

A comparison of the various protein sequences encoding GPD genes from *Saccharomyces cerevisiae* (GenBank Accession No. CAA24607; SEQ ID NO:57), *Schizosaccharomyces pombe* (GenBank Accession No. NP_595236; SEQ ID NO:58), *Aspergillus oryzae* (GenBank Accession No. AAK08065; SEQ ID NO:59), *Paralichthys olivaceus* (GenBank Accession No. BAA88638; SEQ ID NO:60), *Xenopus laevis* (GenBank Accession No. P51469; SEQ ID NO:61) and *Gallus gallus* (GenBank Accession No. DECHG3; SEQ ID NO:62) showed that there were several stretches of conserved amino acid sequence between the 6 different organisms (FIGS. 5A and 5B). Thus, two degenerated oligonucleotides (shown below), corresponding to the conserved 'KYDSTHG' (SEQ ID NO:63) and 'TGAAKAV' (SEQ ID NO:64) amino acid sequences, respectively, were designed and used to amplify a portion of the coding region of GPD from *Y. lipolytica*:

```
Degenerated oligonucleotide YL193:
                                    (SEQ ID NO: 65)
AAGTACGAYTCBACYCAYGG Degenerated oligonucleotide YL194:
                                    (SEQ ID NO: 66)
ACRGCCTTRGCRGCDCCRGT
```
[Note:
The nucleic acid degeneracy code used for SEQ ID NOs: 65 and 66 was as follows: R = A/G; Y = C/T; B = C/G/T; and D = A/G/T.]

Based on the full-length sequences of the GPD sequences of FIGS. 5A and 5B, it was hypothesized that the *Yarrowia lipolytica* GPD gene amplified as described above would be missing ~50 amino acids from its N-terminus and about ~115 amino acids from its C-terminus.

The PCR amplification was carried out in a 50 μl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer, 50 ng genomic DNA of *Y. lipolytica* (ATCC #76982) and 1 μl of Taq DNA polymerase (Epicentre Technologies). The thermocycler conditions were set for 35 cycles at 95° C. for 1 min, 56° C. for 30 sec and 72° C. for 1 min, followed by a final extension at 72° C. for 10 min.

The PCR products were purified using a Qiagen PCR purification kit (Valencia, Calif.), and then further purified following gel electrophoresis in 1% (w/v) agarose. Subsequently, the PCR products were cloned into the pGEM-T-easy vector (Promega, Madison, Wis.). The ligated DNA was used to transform cells of *E. coli* DH5α and transformants were selected on LB agar containing ampicillin (100 μg/mL). Analysis of the plasmid DNA from one transformant confirmed the presence of a plasmid of the expected size, which was designated as "pT-GPD".

Sequence analyses showed that pT-GPD contained a 507 bp fragment (SEQ ID NO:67). Identity of this sequence was determined by conducting BLAST (Basic Local Alignment Search Tool; Altschul, S. F., et al., *J. Mol. Biol.* 215:403-410 (1993); searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). The DNA sequence was translated in all reading frames and compared for similarity to all publicly available protein sequences contained in the "nr" database, using the BLASTX algorithm (Gish, W. and States, D. J. *Nature Genetics* 3:266-272 (1993)) provided by the NCBI. The results of the BLAST comparison summarizing the sequence to which SEQ ID NO:67 has the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. The 507 bp of pT-GPD was found to encode 169 amino acids (SEQ ID NO:68). This amino acid fragment had 77% identity and 84% similarity with the GPD protein sequence of fission yeast (GenBank Accession No. NP_595236), with an expectation value of 6e-68. The *Yarrowia* sequence possessed the 'KYDSTHG' (SEQ ID NO:63) and 'TGAAKAV' (SEQ ID NO:64) amino acid sequences (corresponding to the degenerate primers used to amplify the fragment) at its N- and C-termini.

To isolate the GPD promoter regions, a genome-walking technique (TOPO® Walker Kit, Invitrogen) was utilized, as described in Example 2. Briefly, genomic DNA of *Y. lipolytica* was digested with KpnI, SacI, SphI or PacI, and dephosphorylated with Calf Intestinal Alkaline Phosphatase (CIP). Primer extension reactions were then carried out using primer YL206 (SEQ ID NO:69). The primer extended products were linked with TOPO® Linker and then used as template in PCR reactions with LinkAmp Primer1 (SEQ ID NO:29) and primer YL207 (SEQ ID NO:70). The newly amplified product was subjected to a second PCR reaction using the LinkAmp primer 2 (SEQ ID NO:77) and YL208 (SEQ ID NO:71) primers.

The PCR products comprising the 5' upstream region of the GPD gene were purified using a Qiagen PCR purification kit, followed by gel electrophoresis in 1% (w/v) agarose. Products were then cloned into the pGEM-T-easy vector (Promega, Madison, Wis.). The ligated DNA was used to transform *E. coli* DH5α and transformants were selected on LB agar containing ampicillin (100 µg/mL).

Analysis of the plasmid DNA from one transformant comprising the 5' upstream region of the GPD gene confirmed the presence of the expected plasmid, designated pT-GPDP. Sequence analyses showed that pT-GPDP contained a fragment of 1848 bp (SEQ ID NO:72), which included 1525 bp of 5' upstream sequence from the nucleotide 'A' (designated as +1) of the translation initiation codon 'ATG' of the GPD gene. The nucleotide region between the −968 position and the ATG translation initiation site of the GPD gene was determined to contain the putative promoter region ("GPDPro", provided as SEQ ID NO:56).

Example 9

(Prophetic)

Expression of *Yarrowia lipolytica* PDAT and DGAT2 ORFs Under the Control of a *Yarrowia* Promoter The present Example describes the over-expression of the PDAT and DGAT2 ORFs in chimeric genes under the control of a *Yarrowia lipolytica* promoter in a wild type *Yarrowia* strain.

Expression of *Y. lipolytica* DGAT2 in *Yarrowia lipolytica* The ORF of *Y. lipolytica* DGAT2, i.e., SEQ ID NO:86 which encodes the protein of 355 amino acid residues provided herein as SEQ ID NO:79, was PCR-amplified using upper primer P145 (SEQ ID NO:73) and lower primer P146 (SEQ ID NO:74) from the genomic DNA of *Y. lipolytica* ATCC #90812. The expected 1071 bp fragment was isolated, purified, digested with Nco I and Not I and cloned into Nco I-Not I cut pY5-13 vector (described in Example 1), such that the gene was under the control of the *Y. lipolytica* TEF promoter. Correct transformants were confirmed by miniprep analysis and the resultant plasmid was designated as pY27-DGAT2.

Plasmids pY5-13 (the "control") and pY27-DGAT2 will be transformed into *Y. lipolytica* ATCC #90812 wild-type (WT) and DGAT2-disrupted ATCC #90812 ("S-D") strains and selected on BIO 101 Systems DOB/CSM-Leu plates (Krackeler Scientific, Inc., Albany, N.Y.). Single colonies of transformants will be grown up and GC analyzed, as described in the General Methods.

Expression of *Y. lipolytica* PDAT in *Yarrowia lipolytica*

The ORF of *Y. lipolytica* PDAT was PCR-amplified using primers YPDAT5 (SEQ ID NO:75) and YPDAT3 (SEQ ID NO:76) and genomic DNA from *Y. lipolytica* ATCC #90812 as the template. The expected 1947 bp fragment was isolated, purified, digested with Not I and cloned into Not I cut vector pY5-22GPD under the control of the *Yarrowia* GPD promoter. Vector pY5-22GPD is similar to pY5-13 (Example 1), having an *E. coli* Ap$^R$ gene, *E. coli* ori and *Yarrowia* ARS sequence. Correct transformants were confirmed by analysis of plasmid DNA and the resultant plasmid was designated as pY27-PDAT.

Plasmids pY5-22GPD (the "control") and pY27-PDAT will be transformed into *Y. lipolytica* ATCC #90812 wild-type (WT) and PDAT-disrupted ATCC #90812 ("S—P") strains and selected on BIO 101® Systems DOB/CSM-Leu plates. Single colonies of transformants will be grown up and GC analyzed, as described in the General Methods.

Expected Results

Since both PDAT and DGAT2 enzymes are involved in oil biosynthesis, their over-expression is expected to result in increased oil content under conditions when these enzymes are limiting. This is supported by results that demonstrated disruption of DGAT2, PDAT and both genes in combination resulted in lower oil content.

What is claimed is:

1. An isolated nucleic acid molecule encoding a phospholipid:diacylglycerol acyltransferase enzyme, selected from the group consisting of:
   (a) an isolated nucleic acid molecule encoding the amino acid sequence as set forth in SEQ ID NO:46;
   (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS;
   (c) an isolated nucleic acid molecule that is completely complementary to (a) or (b); and, (d) an isolated nucleic acid molecule comprising a first nucleotide sequence encoding a phospholipid:diacylglycerol acyltransferase enzyme of at least 648 amino acids that has at least 95% identity based on the Clustal W method of alignment when compared to a polypeptide having the sequence as set forth in SEQ ID NO:46 or a second nucleotide sequence comprising the complement of the first nucleotide sequence.

2. The isolated nucleic acid molecule of claim 1 having the nucleotide sequence as set forth in SEQ ID NO 45.

3. A chimeric gene comprising the isolated nucleic acid molecule of claim 1 operably linked to suitable regulatory sequences.

4. A transformed host cell comprising the chimeric gene of claim 3.

5. The transformed host cell of claim 4, selected from the group consisting of algae, bacteria, molds, fungi and yeasts.

6. The transformed host cell of claim 5, wherein the yeast is an oleaginous yeast.

7. The transformed host cell of claim 6, wherein the oleaginous yeast cell is selected from the group consisting of *Yarrowia*, *Candida*, *Rhodotorula*, *Rhodosporidium*, *Cryptococcus*, *Trichosporon* and *Lipomyces*.

8. The transformed host cell of claim 7, wherein the host cell is *Yarrowia lipolytica*.

9. A method of increasing triacylglycerol content in a transformed host cell comprising:
   (a) providing a transformed host cell comprising:
      (i) at least one gene encoding an acyltransferase enzyme having the amino acid sequence as set forth in SEQ ID NO:46 under the control of suitable regulatory sequences; and
      (ii) a source of fatty acids;
   (b) growing the cell of step (a) under conditions whereby the at least one gene encoding an acyltransferase enzyme is expressed, resulting in the transfer of the fatty acids to triacylglycerol; and
   (c) optionally recovering the triacylglycerol of step (b).

10. The method according to claim 9, wherein growing the cell of step (a) under conditions whereby the genes of (i) and (ii) are expressed results in the production of at least one ω-3 or ω-6 fatty acid and its transfer to triacylglycerol.

11. The method according to claim 10, wherein the at least one gene encoding at least one enzyme of the ω-3/ω-6 fatty acid biosynthetic pathway is selected from the group consisting of desaturases and elongases.

12. The method according to claim 11, wherein the desaturase is selected from the group consisting of: Δ9 desaturase, Δ12 desaturase, Δ6 desaturase, Δ5 desaturase, Δ17 desaturase, Δ8 desaturase, Δ15 desaturase and Δ4 desaturase.

13. The method according to claim 9, wherein the host cell is selected from the group consisting of algae, bacteria, molds, fungi and yeasts.

14. The method according to claim 13, wherein the host cell is an oleaginous yeast.

15. The method according to claim 14 wherein the oleaginous yeast is a member of a genus selected from the group of consisting of *Yarrowia*, *Candida*, *Rhodotorula*, *Rhodosporidium*, *Cryptococcus*, *Trichosporon* and *Lipomyces*.

16. The method according to claim 15, wherein the oleaginous yeast is *Yarrowia lipolytica*.

17. The method according to claim 9 wherein the fatty acid is selected from the group consisting of: stearate, oleic acid, linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid, eicosadienoic acid and eicosatrienoic acid.

* * * * *